United States Patent
Grueneberg et al.

(10) Patent No.: US 9,963,452 B2
(45) Date of Patent: May 8, 2018

(54) METHODS, COMPOUNDS, AND COMPOSITIONS FOR INHIBITION OF ROS

(71) Applicants: Dorre A. Grueneberg, Newton, MA (US); Ori Kalid, Pardes-Hanna (IL); Jun Xian, Sharon, MA (US); Sharanappa B. Rajur, Andover, MA (US); Hwa-Ok Kim, Lexington, MA (US); Venugopal Rao Neelagiri, Acton, MA (US); Paresh Salgaonkar, Medford, MA (US); Divakaramenon Sethumadhavan, Waltham, MA (US); Chaeho Moon, Burlington, MA (US); Madhavi Neelagiri, Acton, MA (US)

(72) Inventors: Dorre A. Grueneberg, Newton, MA (US); Ori Kalid, Pardes-Hanna (IL); Jun Xian, Sharon, MA (US); Sharanappa B. Rajur, Andover, MA (US); Hwa-Ok Kim, Lexington, MA (US); Venugopal Rao Neelagiri, Acton, MA (US); Paresh Salgaonkar, Medford, MA (US); Divakaramenon Sethumadhavan, Waltham, MA (US); Chaeho Moon, Burlington, MA (US); Madhavi Neelagiri, Acton, MA (US)

(73) Assignee: AUGUSTA PHARMACEUTICALS INC., Newton, MA (US)

(*) Notice: Subject to any disclaimer, the term of this patent is extended or adjusted under 35 U.S.C. 154(b) by 0 days. days.

(21) Appl. No.: 14/775,825

(22) PCT Filed: Mar. 13, 2014

(86) PCT No.: PCT/IB2014/059733
§ 371 (c)(1),
(2) Date: Sep. 14, 2015

(87) PCT Pub. No.: WO2014/141129
PCT Pub. Date: Sep. 18, 2014

(65) Prior Publication Data
US 2016/0031890 A1    Feb. 4, 2016

Related U.S. Application Data

(60) Provisional application No. 61/781,126, filed on Mar. 14, 2013.

(51) Int. Cl.
*A61K 31/505* (2006.01)
*A61K 31/53* (2006.01)
(Continued)

(52) U.S. Cl.
CPC .......... *C07D 487/04* (2013.01); *A61K 31/194* (2013.01); *A61K 31/404* (2013.01);
(Continued)

(58) Field of Classification Search
CPC .................................................... A61K 31/506
(Continued)

(56) References Cited

U.S. PATENT DOCUMENTS

| 2007/0098816 | A1* | 5/2007 | Nakanishi | A61K 45/06 424/649 |
| 2009/0076037 | A1* | 3/2009 | Connolly | C07D 498/04 514/262.1 |

FOREIGN PATENT DOCUMENTS

| WO | 2010141738 A2 | 3/2011 |
| WO | 2012016133 A2 | 2/2012 |

OTHER PUBLICATIONS

Cozalbes et al. "Development and Experimental Validation of a Docking Stragtegy for the Generation of Kinase-Targeting Libraries," J. Med. Chem. 2008, vol. 51, pp. 3124-3132.*
(Continued)

*Primary Examiner* — Shengjun Wang
(74) *Attorney, Agent, or Firm* — Gearhart Law LLC

(57) ABSTRACT

The present invention relates to a method using some novel compounds and compositions for the inhibition of ROS
(Continued)

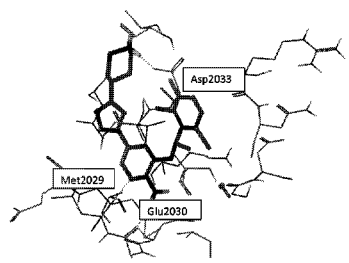

Crizotinib docked into a structural model of the ROS ATP binding site. Dashed yellow lines represent hydrogen bonds. The amino pyridine core forms hydrogen bonds with backbone atoms of the hinge residues Met2029 and Glu2030, while the piperidine group forms a salt bridge with Asp2033.

tyrosine kinase. In particular, the present invention covers a method to treat abnormal cell growth, such as cancer, with ROS 10 inhibitors and compositions having ROS inhibitors. An illustrative compound of the invention is shown below Formula (I).

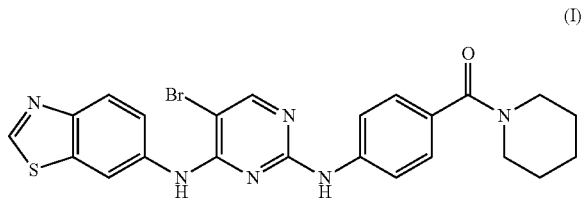

32 Claims, 3 Drawing Sheets

(51) Int. Cl.
| | |
|---|---|
| C07D 487/04 | (2006.01) |
| A61K 45/06 | (2006.01) |
| A61K 31/404 | (2006.01) |
| A61K 31/4375 | (2006.01) |
| A61K 31/454 | (2006.01) |
| A61K 31/497 | (2006.01) |
| A61K 31/506 | (2006.01) |
| A61K 31/519 | (2006.01) |
| A61K 31/551 | (2006.01) |
| C07D 209/08 | (2006.01) |
| C07D 243/14 | (2006.01) |
| C07D 401/14 | (2006.01) |
| C07D 403/12 | (2006.01) |
| C07D 409/14 | (2006.01) |
| C07D 417/12 | (2006.01) |
| C07D 417/14 | (2006.01) |
| C07D 471/04 | (2006.01) |
| A61K 31/194 | (2006.01) |
| A61K 31/437 | (2006.01) |
| A61K 31/452 | (2006.01) |
| A61K 31/4545 | (2006.01) |

(52) U.S. Cl.
CPC ........ *A61K 31/437* (2013.01); *A61K 31/4375* (2013.01); *A61K 31/452* (2013.01); *A61K 31/454* (2013.01); *A61K 31/4545* (2013.01); *A61K 31/497* (2013.01); *A61K 31/506* (2013.01); *A61K 31/519* (2013.01); *A61K 31/53* (2013.01); *A61K 31/551* (2013.01); *A61K 45/06* (2013.01); *C07D 209/08* (2013.01); *C07D 243/14* (2013.01); *C07D 401/14* (2013.01); *C07D 403/12* (2013.01); *C07D 409/14* (2013.01); *C07D 417/12* (2013.01); *C07D 417/14* (2013.01); *C07D 471/04* (2013.01)

(58) Field of Classification Search
USPC .......................................... 514/272
See application file for complete search history.

(56) References Cited

OTHER PUBLICATIONS

PCT/IB2014/059733 International Preliminary Report on Patentability, dated Sep. 15, 2015, 7 pages.
PCT/IB2014/059733 International Search Report / written Opinion, dated Dec. 19, 2014, 13 pages.
RN 1032394-06-1 (entered STN: Jul. 2, 2008), Chemical abstracts services (online), STN International, Columbus, Ohio, US.
El-Gendy et al., "Marine bacteria. XXXVI. Essramycin: A first triazolopyrimidine antibiotic isolated from nature", J. of Antibiotics (2008), 61 (3), 149-157.
I. El-Deeb, et al. ROSReceptorTyrosine Kinase:ANew PotentialTarget forAnticancer Drugs, Medicinal Research Reviews, vol. 31 (2011) pp. 794-818.
T. Gu, et al. Survey of Tyrosine Kinase Signaling Reveals ROS Kinase Fusions in Human Cholangiocarcinoma, PLoS ONE online publication available on www.plosone.org since Jan. 1, 2011 vol. 6 /Issue 1.
J. Cui, et al. Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK), J. Med. Chem., Pre-publication / Just Accepted manuscript (Downloaded from http://pubs.acs.org on Aug. 4, 2011).
K. Milkiewicz and G. Ott, Inhibitors of anaplastic lymphoma kinase: a patent review, Expert Opin. Ther. Patents [Early Online] accessed on Nov. 5, 2010.
E. Kwak, et al., Anaplastic Lymphoma Kinase Inhibition in Non-Small-Cell Lung Cancer, The New England Journal of Medicine, vol. 363 (2010), pp. 1693-1703.

* cited by examiner

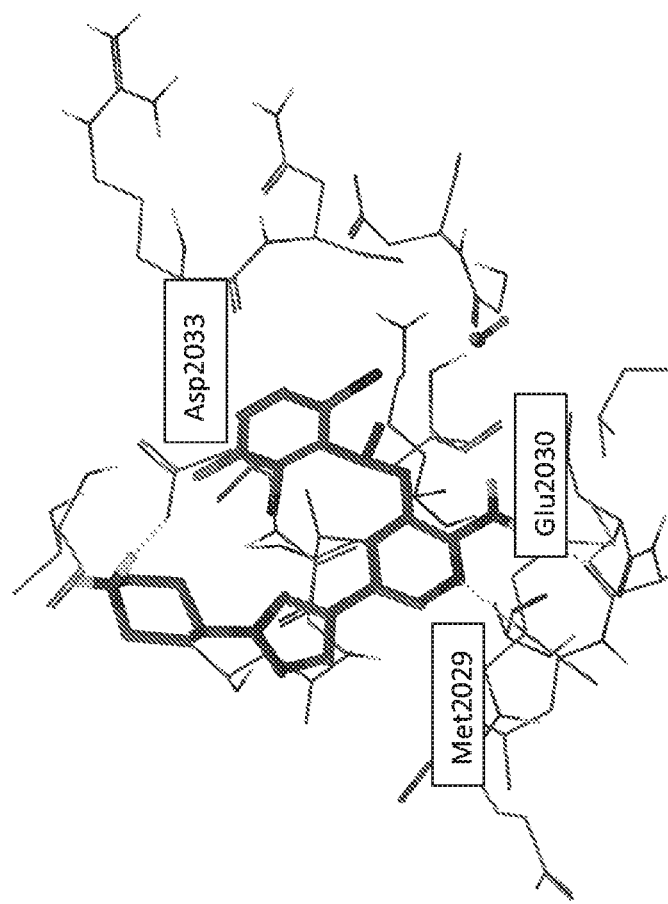
Figure 1: Crizotinib docked into a structural model of the ROS ATP binding site. Dashed yellow lines represent hydrogen bonds. The amino pyridine core forms hydrogen bonds with backbone atoms of the hinge residues Met2029 and Glu2030, while the piperidine group forms a salt bridge with Asp2033.

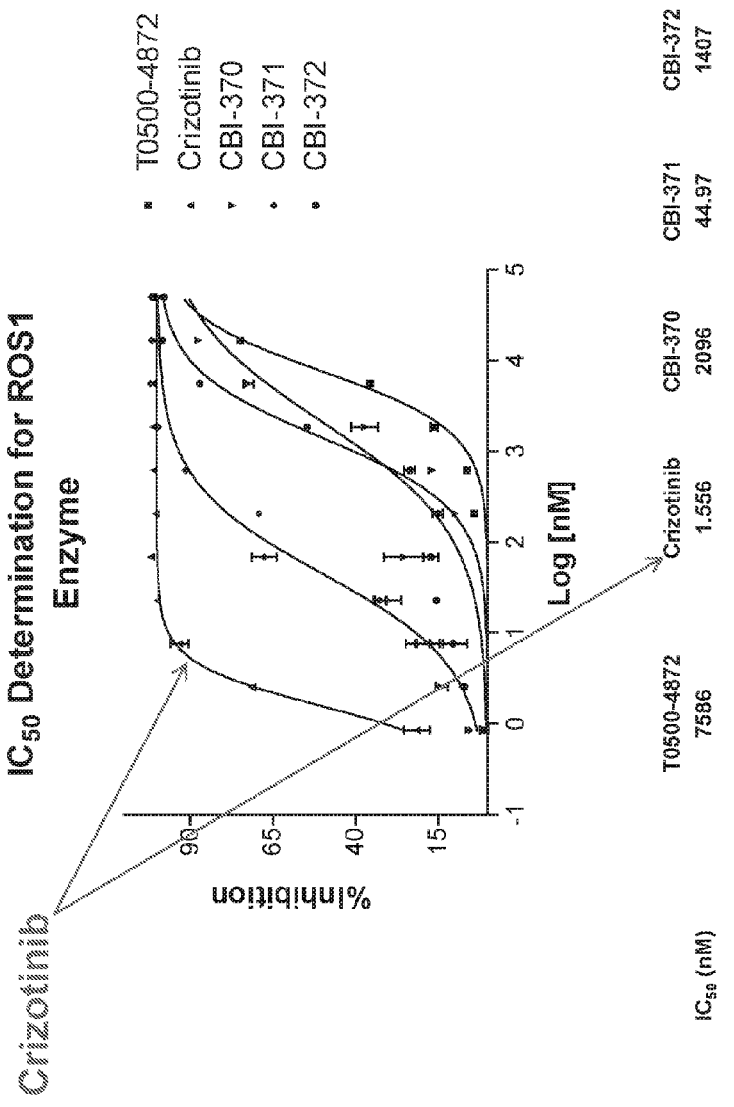
Figure 2: A subset of small molecules that inhibited the *in vitro* catalytic activity of ROS, employing a substrate phosphorylation assay purchased from Cisbio. The concentration of Crizotinib producing a 50% inhibition of ROS kinase activity (i.e., $IC_{50}$) was 1.556 nM.

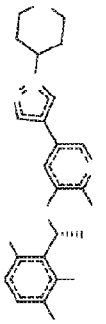
Figure 3: Crizotinib inhibition of ROS as judged by two approaches: 1) inhibition of enzymatic activity *in vitro*; and 2) growth inhibition of one cervical cancer cell line (HeLa) and four glioblastoma cells lines (U138, U118, LN18 and U87). U138 and U118 have been documented to express aberrant ROS (FIG-ROS fusion).

METHODS, COMPOUNDS, AND COMPOSITIONS FOR INHIBITION OF ROS

CLAIM OF PRIORITY

This application claims priority of the U.S. provisional patent application No. 61/781,126 filed on Mar. 14, 2013, the contents of which are fully incorporated herein by reference.

FIELD OF THE INVENTION

The present invention relates to methods to treating abnormal cell growth. In particular, the present invention related to treating cancer using compounds and compositions for inhibition of ROS receptor tyrosine kinase ("ROS").

BACKGROUND OF THE INVENTION

Receptor tyrosine kinases play important roles in mediating the signal transduction and cellular communication process. Among the 58 receptor tyrosine kinases, only two are considered "orphan" kinases because their ligands have not been identified. ROS is one of the "orphan" tyrosine kinases.

Extensive research has been conducted to study the expression, effects, and localization of both ROS encoding genes and the various forms of ROS peptides. Several studies indicate that ROS are involved in the oncogenesis and tumor progression of various cancers. For example, overexpression of ROS cDNA and RNA was observed in surgical specimens in a significant proportion of glioblastoma samples. In addition, a large scale survey study revealed that in non-small cell lung cancer (NSCLC) tumors, ROS protein was highly expressed and the down stream effectors of ROS, such as insulin receptor substrate 2 (IRS-2), are highly phosphorylated, suggesting elevated ROS activities. Moreover, ROS up-regulation has been shown in gastric cancer model animals, liver cancer model animals, fibroadenoma tumor samples, colon adenocarcinoma cell lines, and a rat hepatoma cell line, indicating possibly extensive involvement of ROS in cancer development.

Aside from general over-expression, the ROS gene has also been shown to be rearranged in the form of fusion proteins in cancer-related samples. One key example is the "FIG-ROS" fusion in glioblastoma cells. Fused in Glioblastoma (FIG) is a gene that encodes a protein that peripherally associates with Giogi apparatus. The FIG-ROS kinase is encoded by 7 FIG-derived exons and 9 ROS-derived exons, a potent oncogene, capable of initiating malignant transformation in vitro when localized to the Golgi apparatus and activating growth signaling pathways. FIG-ROS is highly expressed in two glioblastoma cell lines (U-118MG and U-138 MG), suggesting that FIG-ROS is present in the primary tumors that established the two cell lines. Moreover, in a mouse model system, the FIG-ROS fusion cooperates with the loss of CDKN2A to produce glioblastoma. The involvement of CDKN2A is not surprising, given its classification as one of the most frequently deleted genes in glioblastoma. All these studies support the conclusion that ROS plays an important role in mediating cancer development.

In addition to the probable role in tumor formation and progression, ROS has been shown be involved in other illnesses such as cardiovascular diseases and male infertility. For example, a number of studies have correlated between the ROS gene and incidence of different cardiovascular diseases, such as myocardial infarction and hypertension. Similarly, male homozygous ROS knockout mice are infertile, with likely abnormal sperm development. These studies suggest that ROS may play important roles in diseases other than cancers.

Significant efforts have been focusing on generating ROS inhibitors that may help to provide a treatment cancer and other related diseases. A number of inhibitors, such as Staurosporine, AST-487 and PP 2 have been reported to inhibit ROS kinase activities. Among these, Staurosporine has shown a high potency with $IC_{50}$ of 0.9 nM. These inhibitors, however, are highly unselective and their prospects of clinical application are probably minimum.

Following the finding of the non-specific ROS inhibitors, further studies discovered a new hit pyrazole derivative—KIST301072—that inhibits 94% of the ROS kinase activities at a concentration of 10 uM, while blocking less than 30% of the activities of other kinases at the same level. A dose response study showed that KIST301072 has an $IC_{50}$ of about 199 nM. In addition, a structurally related compound, KIST301080 has been shown to inhibit ROS kinase activity with an $IC_{50}$ of 209 nM. New studies will address the potential clinical applications of KIST301072 and KIST301080 in treating cancer, cardiovascular diseases, and infertility.

The current invention introduces a new set of compounds that selectively inhibits ROS kinase activities. These compounds may have significant pharmaceutical implications in the treatment of cancer, cardiovascular diseases, and infertility.

SUMMARY OF THE INVENTION

One aspect of this invention is the provision of a method to reduce the speed of, stop, or reverse progression of abnormal cell growth in a mammal, comprising
  administering to the mammal a composition comprising therapeutically effective amount of a compound of formula I:

$$Ar^1-(CH_2)_n-(X)_m-Ar^2 \qquad \text{I}$$

or a pharmaceutically acceptable salt thereof,
wherein
$Ar^1$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O;
n is 0, 1, 2, or 3;

X is N, N(O), S, S(O), S(O)$_2$, O, or C(O);
m is 0 or 1;
Ar$^2$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O.

One aspect of this invention is the provision of a method to reduce the speed of, stop, or reverse progression of abnormal cell growth in a mammal, comprising
administering to the mammal a composition comprising therapeutically effective amount of a compound of formula II:

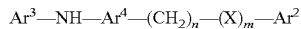

Ar$^3$—NH—Ar$^4$—(CH$_2$)$_n$—(X)$_m$—Ar$^2$     II wherein
n is 0 or 1; and
X is N;
m is 0 or 1;
Ar$^2$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)— alkyl, —NH—C(O)-aryl and heteroaryl, with the proviso that no two adjacent ring heteroatoms on a ring are both S or both O;
Ar$^3$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)— alkyl, —NH—C(O)-aryl and heteroaryl, with the proviso that no two adjacent ring heteroatoms on a ring are both S or both O; and
Ar$^4$ is aryl, heteroaryl, arylalkyl or heteroarylalkyl, wherein the heteroatom of each of said heteroaryl and heteroaryl independently numbers 1, 2 or 3, and is independently selected from N, S or O, Another aspect of the current invention is to provide a method to inhibit ROS kinase activities using the compounds of Formula I and II.

Another aspect of the current invention is to provide a method to treat abnormal cell growth with the compounds of Formula I and II.

Another aspect of the current invention is to provide a method to treat cancer with the compounds of Formula I and II.

Yet another aspect of the current invention is to provide a method to treat abnormal cell growth with the compounds of Formula I, through the inhibition of ROS tyrosine kinase activities.

Yet another aspect of the current invention is to provide a method to treat cancer with the compounds of Formula I, through the inhibition of ROS tyrosine kinase activities.

Another aspect of this invention is the provision of methods of treating a disease via the inhibition of ROS in a subject (e.g., a human) in need thereof by administering to the subject an effective amount of the compound or the pharmaceutical formulation of the compounds of Formula I and II.

Another preferred embodiment is a pharmaceutical formulation comprising a pharmaceutically acceptable compound of Formula I and II, which provides, upon administration to a human, a decrease in tumor burden and/or metastases. The pharmaceutical formulation can be administered by oral means or other suitable means.

Yet another embodiment is a method of treating abnormal cell growth in a subject (e.g., a human) in need thereof by administering to the subject an effective amount of the compound or the pharmaceutical formulation of the Formula I and II.

Yet another embodiment is a method of treating cancer in a subject (e.g., a human) in need thereof by administering to the subject an effective amount of the compound or the pharmaceutical formulation of the Formula I and II.

Yet another embodiment is a method of treating glioblastoma in a subject (e.g., a human) in need thereof by administering to the subject an effective amount of the compound or the pharmaceutical formulation of the Formula I and II.

Yet another embodiment is a method of treating cholangiocarcinoma in a subject (e.g., a human) in need thereof by administering to the subject an effective amount of the compound or the pharmaceutical formulation of the Formula I and II.

Yet another embodiment is a method of treating non small cell lung cancer (NSCLC) in a subject (e.g., a human) in need thereof by administering to the subject an effective amount of the compound or the pharmaceutical formulation of the Formula I and II.

Yet another embodiment is a method of treating ovarian cancer in a subject (e.g., a human) in need thereof by administering to the subject an effective amount of the compound or the pharmaceutical formulation of the Formula I and II, wherein the cancer is mediated by ROS or a fusion gene between ROS and another sequence.

Yet another embodiment is a method of treating ovarian cancer in a subject (e.g., a human) in need thereof by administering to the subject an effective amount of the compound or the pharmaceutical formulation of the Formula I and II.

Yet another embodiment is a method of treating colon cancer in a subject (e.g., a human) in need thereof by administering to the subject an effective amount of the compound or the pharmaceutical formulation of the Formula I and II.

Yet another embodiment is a method of treating breast cancer in a subject (e.g., a human) in need thereof by administering to a subject (e.g., a human) in need thereof by administering to the subject an effective amount of the compound or the pharmaceutical formulation of the Formula I and II.

Yet another embodiment is a method of treating leukemia in a subject (e.g., a human) in need thereof by administering to the subject an effective amount of the compound or the pharmaceutical formulation of the Formula I and II.

Yet another embodiment is a method of treating cardiovascular disease in a subject (e.g., a human) in need thereof by administering to the subject an effective amount of the compound or the pharmaceutical formulation of the Formula I and II.

Yet another embodiment is a method of treating male infertility in a subject (e.g., a human) in need thereof by administering to the subject an effective amount of the compound or the pharmaceutical formulation of the Formula I and II.

Yet another embodiment is a method of treating cancer, before or after surgical resection and/or radiation therapy, in a subject (e.g., a human) in need thereof by administering to the subject an effective amount of the compound or the pharmaceutical formulation of the Formula I and II, including adjunctive therapy to treat nausea, with or without dexamethasone.

Yet another embodiment is a method of treating cancer, before or after surgical resection and or radiation therapy, in a subject (e.g., a human) in need thereof by administering to the subject an effective amount of the compound or the pharmaceutical formulation of the Formula I and II, including adjunctive therapy with one or more additional therapeutic agents, or their pharmaceutically acceptable salts thereof. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™. (4-[2-[4-[(11R)-3,10-dibromo-8-chloro-6,11-dihydro-5H-benzo[5,-6]cyclohepta[1,2-b]pyridin-11-yl-]-1-piperidinyl]-2-oxoehtyl]-1-piperidine-carboxamide, or SCH 66336), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGFR kinase inhibitors), antibodies to EGFR (e.g., C225), GLEEVEC® (C-abl kinase inhibitor from Novartis Pharmaceuticals, East Hanover, N.J.); interferons such as, for example, Intron® (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN®. from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-$HT_3$ receptor inhibitor (e.g., dolansetron, granisetron, ondansetron) with or without dexamethasone.

If formulated as a fixed dose, such combination products employ the compounds of this invention within the dosage range described herein (or as known to those skilled in the art) and the other pharmaceutically active agent or treatment within its dosage range. For example, the CDC2 inhibitor olomucine has been found to act synergistically with known cytotoxic agents in inducing apoptosis (J. Cell Sci., (1995) 108, 2897). The compounds of the invention may also be administered sequentially with known anticancer or cytotoxic agents when a combination formulation is inappropriate. In any combination treatment, the invention is not limited in the sequence of administration; compounds of the Formulas may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the Formula I and II.

Yet another embodiment is a method of preparing a pharmaceutical formulation of the Formula I and II by mixing at least one pharmaceutically acceptable compound of Formula I and II, and, optionally, one or more pharmaceutically acceptable additives or excipients.

For preparing pharmaceutical compositions from the compounds of Formula I and II, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of Formula I and II may also be deliverable transdermally. The transdermal compositions can take the form of creams, lotions, aerosols and/or emulsions and can be included in a transdermal patch of the matrix or reservoir type as are conventional in the art for this purpose.

The compounds of Formula I and II may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

DEFINITIONS

As used above, and throughout this disclosure, the following terms, unless otherwise indicated, shall be understood to have the following meanings. If a definition is missing, convention definition as known to one skilled in the art controls.

"Patient" includes both human and animals.

"Mammal" means humans and other mammalian animals.

The term "inhibitor" refers to a molecule such as a compound, a drug, an enzyme activator or a hormone that blocks or otherwise interferes with a particular biologic activity.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation. Thus, the expression "effective amount" generally refers to the quantity for which the active substance has therapeutic effects. In the present case the active substance is the inhibitor of the ROS kinase activities.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl" group includes an unbranched or branched hydrocarbon chain having one or more double bonds therein. The double bond of an alkenyl group can be unconjugated or conjugated to another unsaturated group. Illustrative alkenyl groups include, but are not limited to, $(C_2-C_8)$alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

As used herein, "alkynyl" group includes an unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "hydroxy" means an OH group;

The term alkyl hydroxy or hydroxyalkyl means an alkyl group as defined above, where the alkyl group has an OH group disposed thereon.

The term "alkoxy" as used herein includes —O-(alkyl), wherein alkyl is defined above.

The term "aminoalkyl" as used herein means a group having one or more nitrogen atoms and one or more alkyl groups as defined above on the nitrogen.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl moiety as defined herein linked via an alkyl moiety (defined above) to a parent core. Non-limiting examples of suitable heteroaryls include 2-pyridinylmethyl, quinolinylmethyl and the like.

"Heterocyclylalkyl" means a heterocyclyl moiety as defined herein linked via an alkyl moiety (defined above) to a parent core. Non-limiting examples of suitable heterocyclylalkyls include piperidinylmethyl, piperazinylmethyl and the like.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "deuterium" as used herein means a stable isotope of hydrogen having odd numbers of protons and neutrons.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom.

The term "(amino)alkoxy" as used herein means a substituent having at least one amino group and at least one alkoxy group.

The term "aryloxy" as used herein means a substituent of the form Ar—O— where Ar is an aryl group as defined herein.

The term "methylenedioxy" as used herein means a functional group with the structural formula —O—CH$_2$—O— which is connected to the molecule by two chemical bonds via the oxygens.

As used herein, "alkoxyalkyl" means -(alkyl)-O-(alkyl), wherein each "alkyl" is independently an alkyl group defined above.

The term "(alkoxyalkyl)amino" as used herein means a substituent having at least one alkoxyalkyl group as defined above and at least one amino group as defined above.

As used herein, the term "aryl" refers to a monocyclic, or fused polycyclic, aromatic carbocycle (ring structure having ring atoms that are all carbon) having from 3 to 24 ring atoms per ring. Illustrative examples of aryl groups include, but are not limited to, the following moieties:

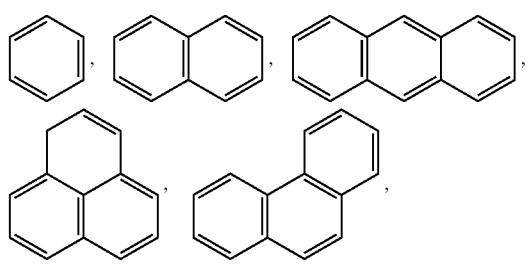

and the like.

Illustrative Substituted Aryls Include:
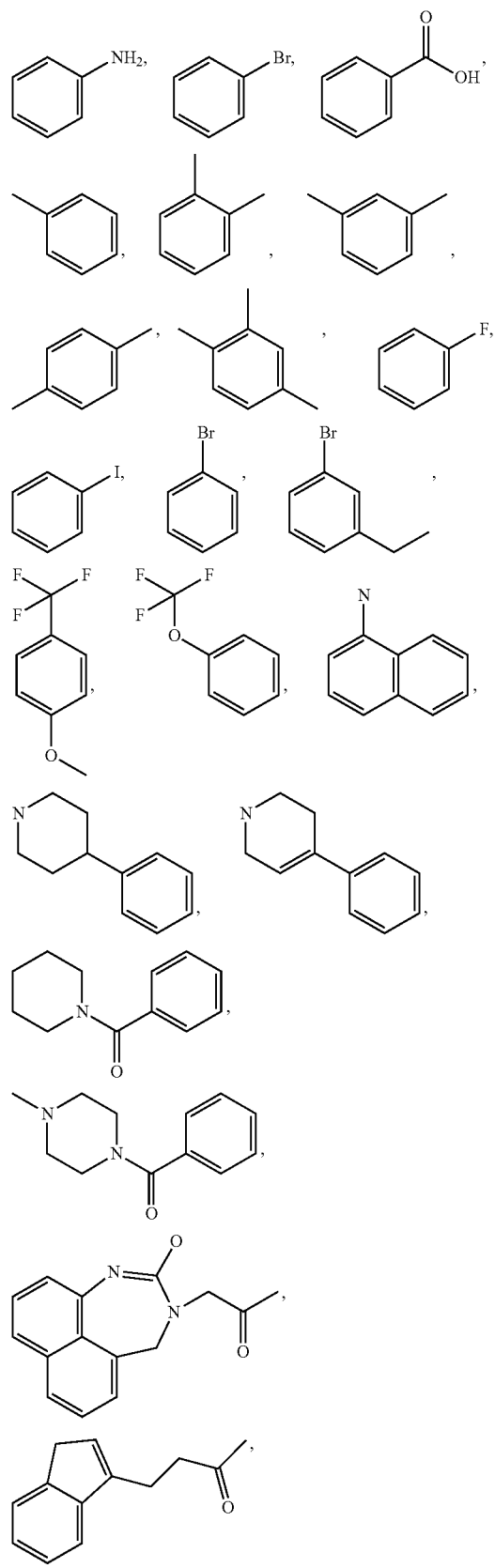
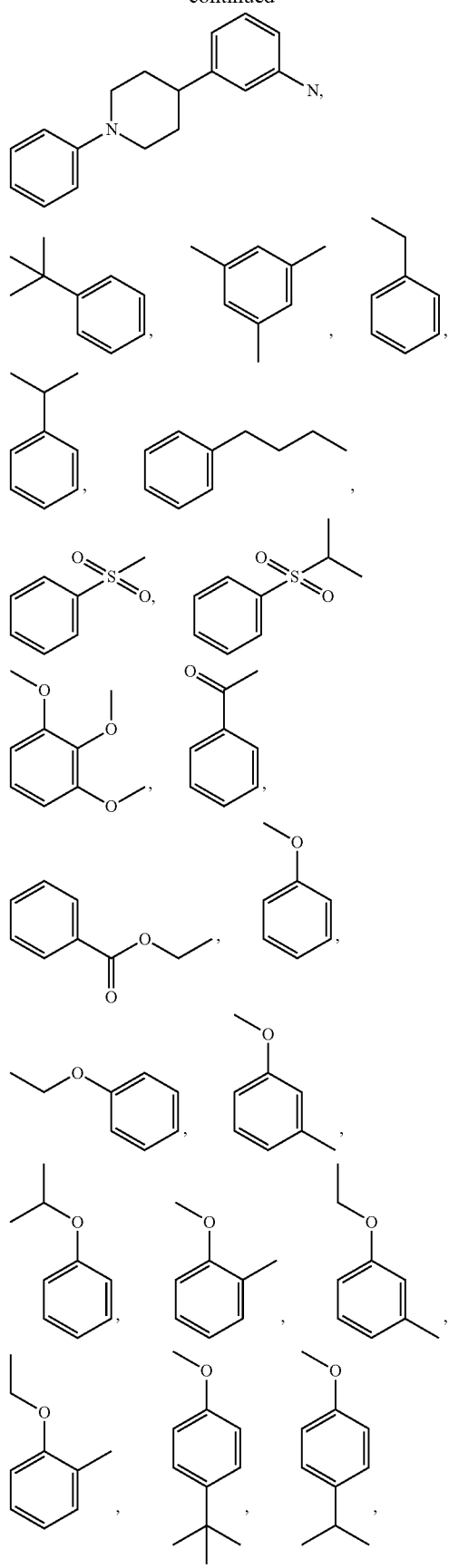

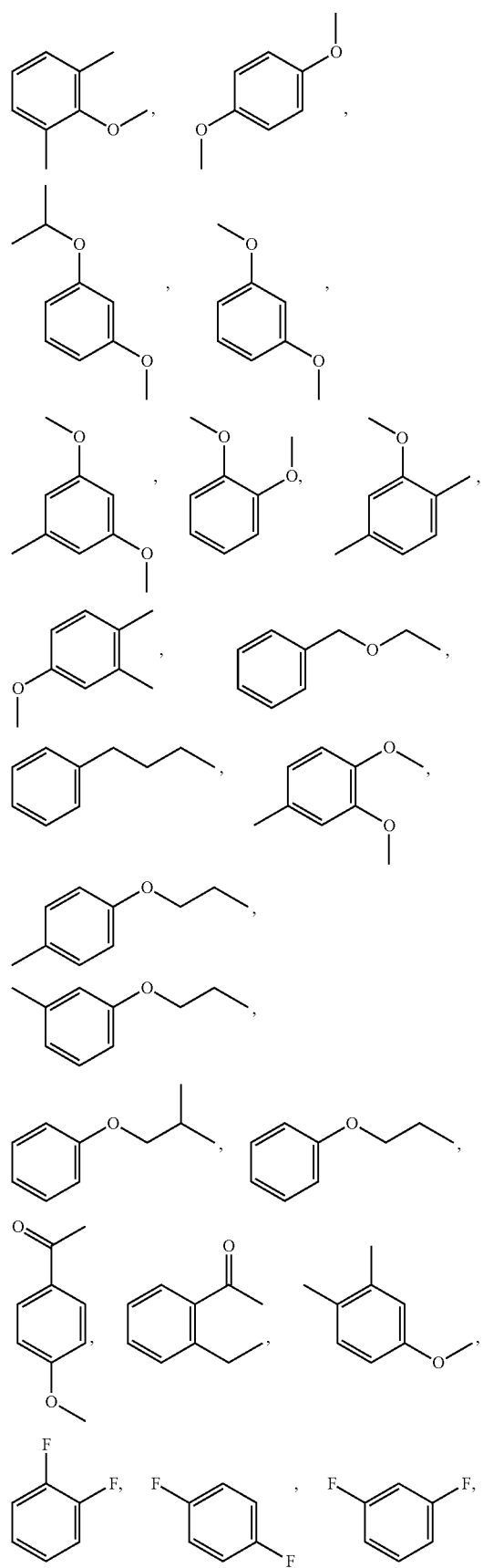
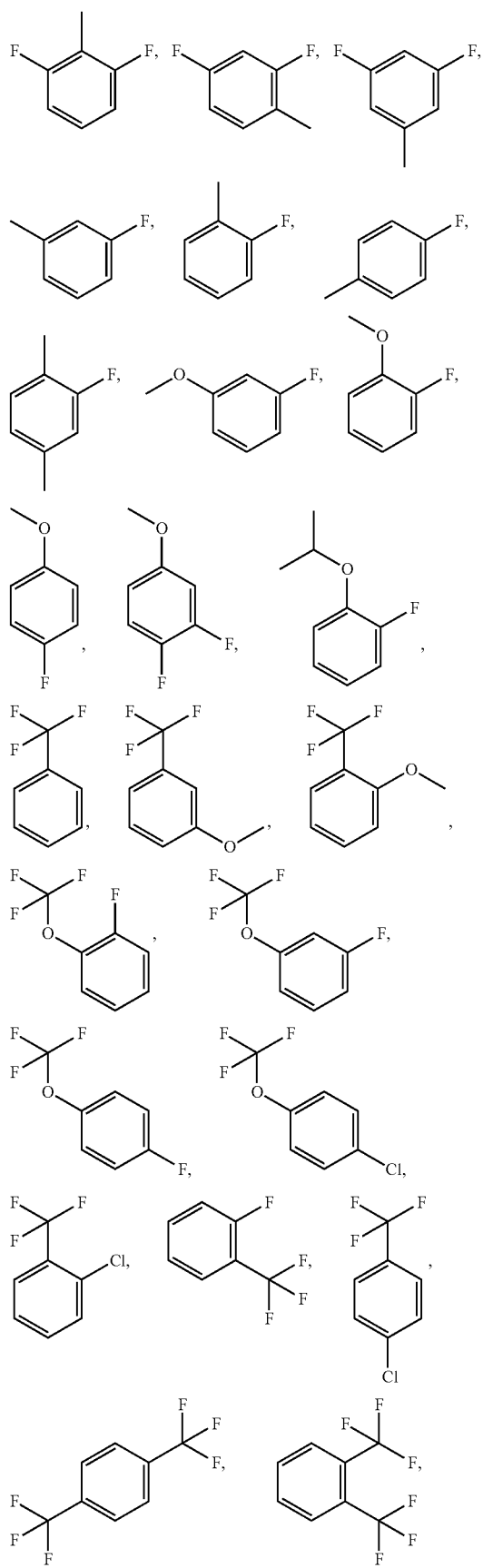

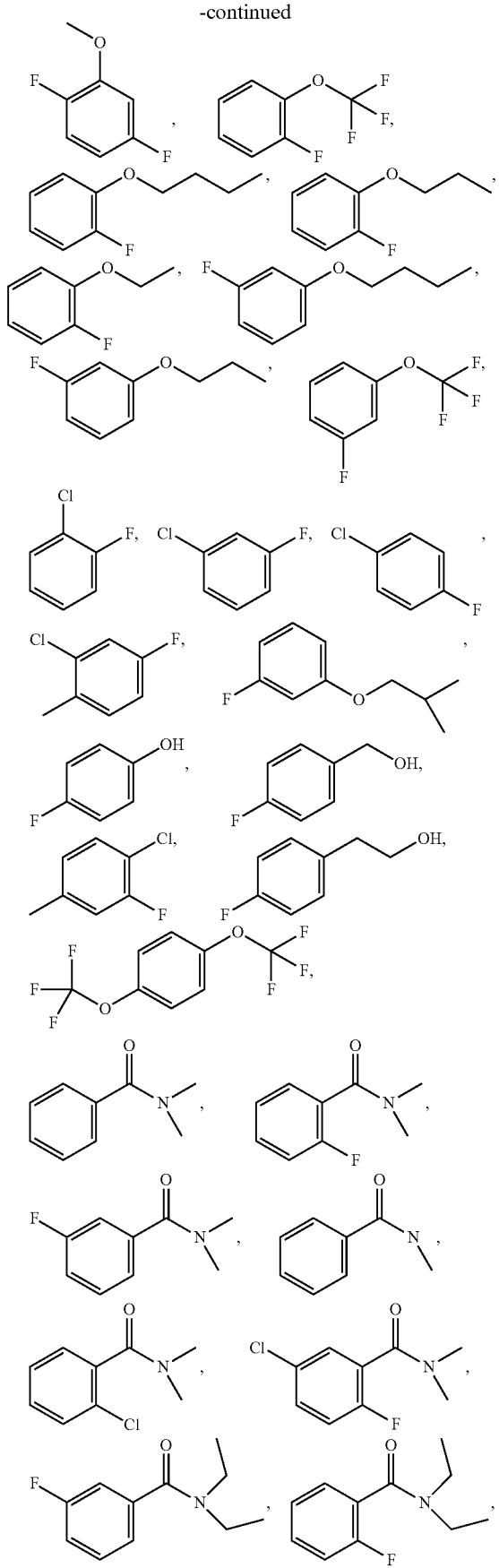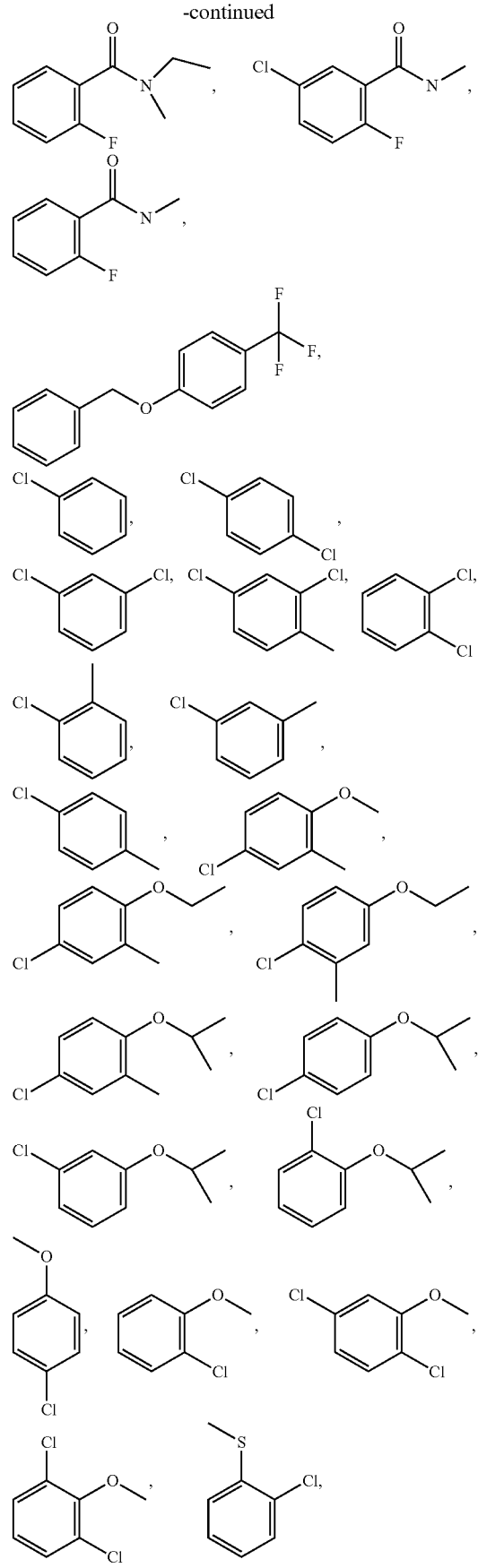

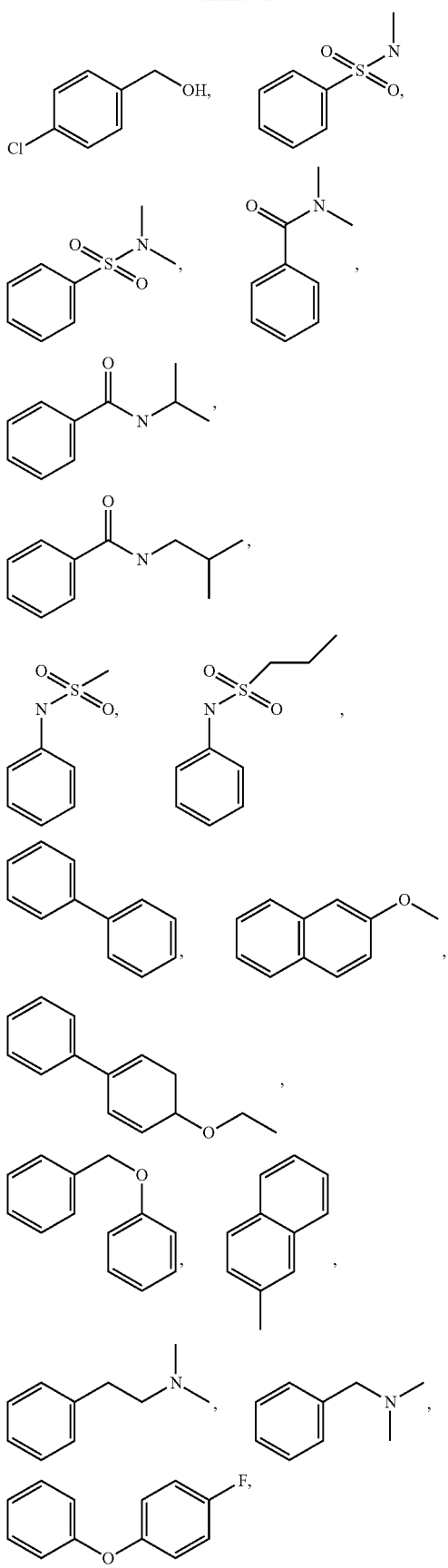

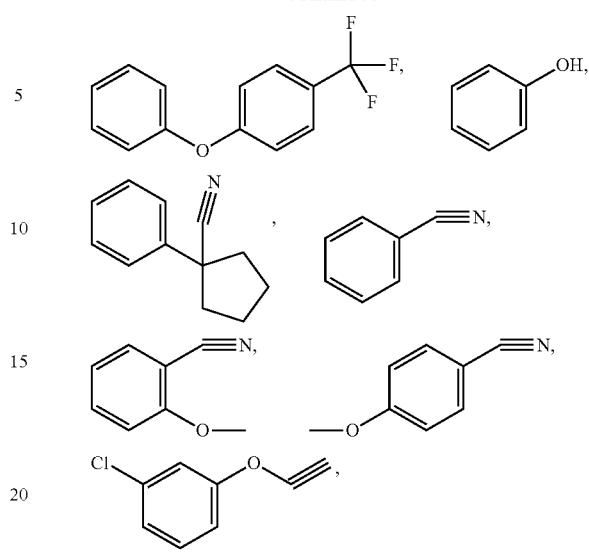

and the like.

As used herein, the term "heteroaryl" refers to a monocyclic, or fused polycyclic, aromatic heterocycle (ring structure having ring atoms selected from carbon atoms as well as nitrogen, oxygen, and sulfur heteroatoms) having from 3 to 24 ring atoms per ring. Illustrative examples of heteroaryl and substituted heteroaryl groups include, but are not limited to the following moieties:

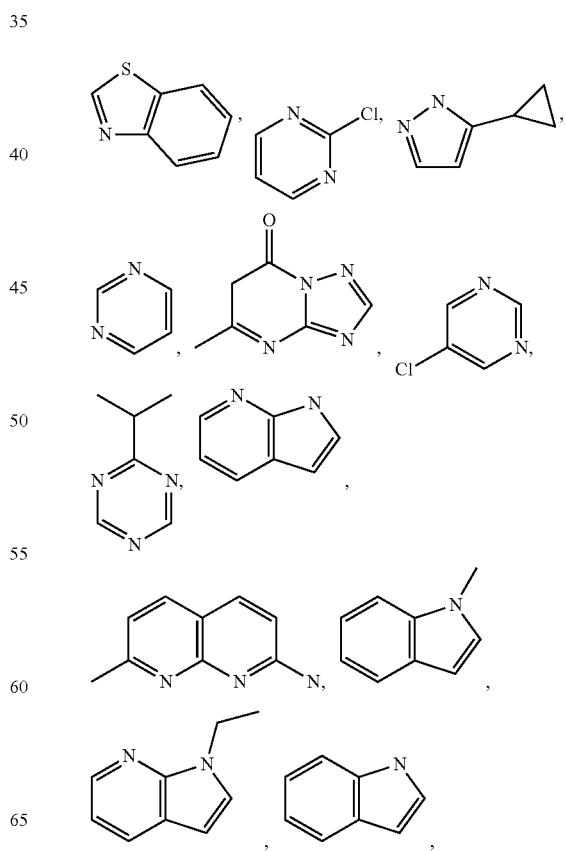

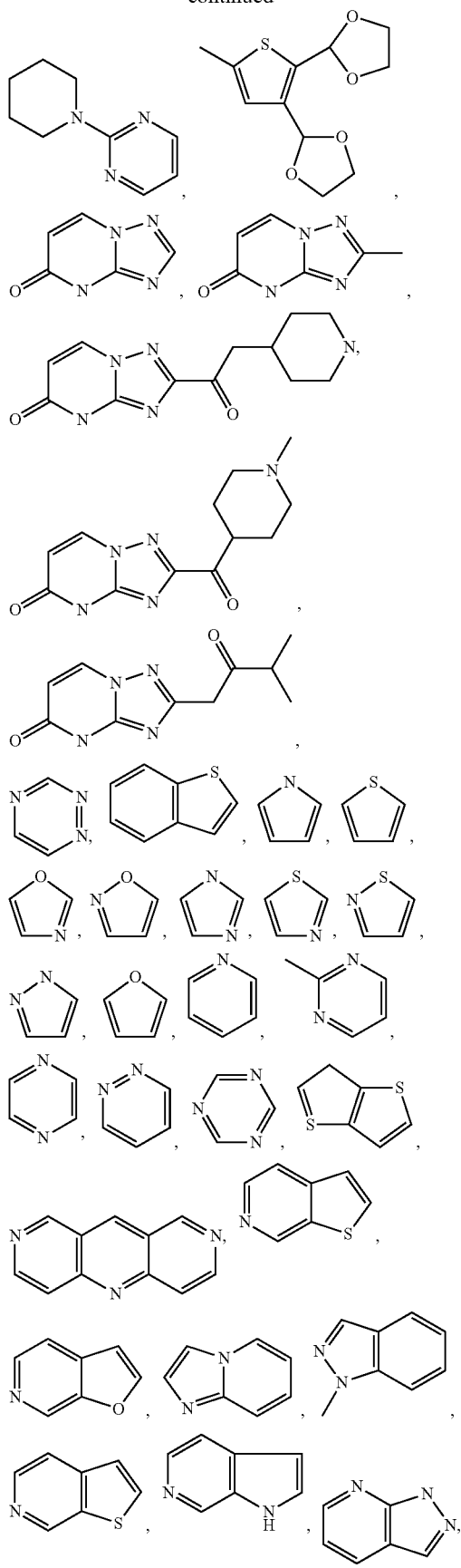
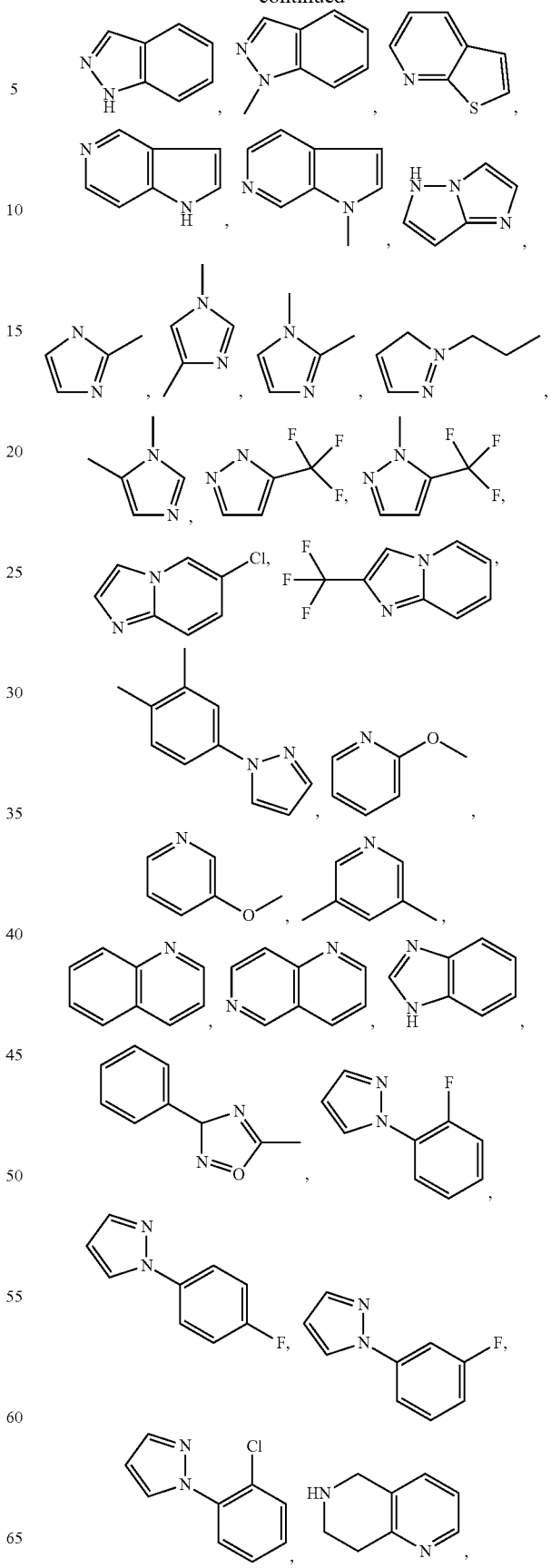

-continued
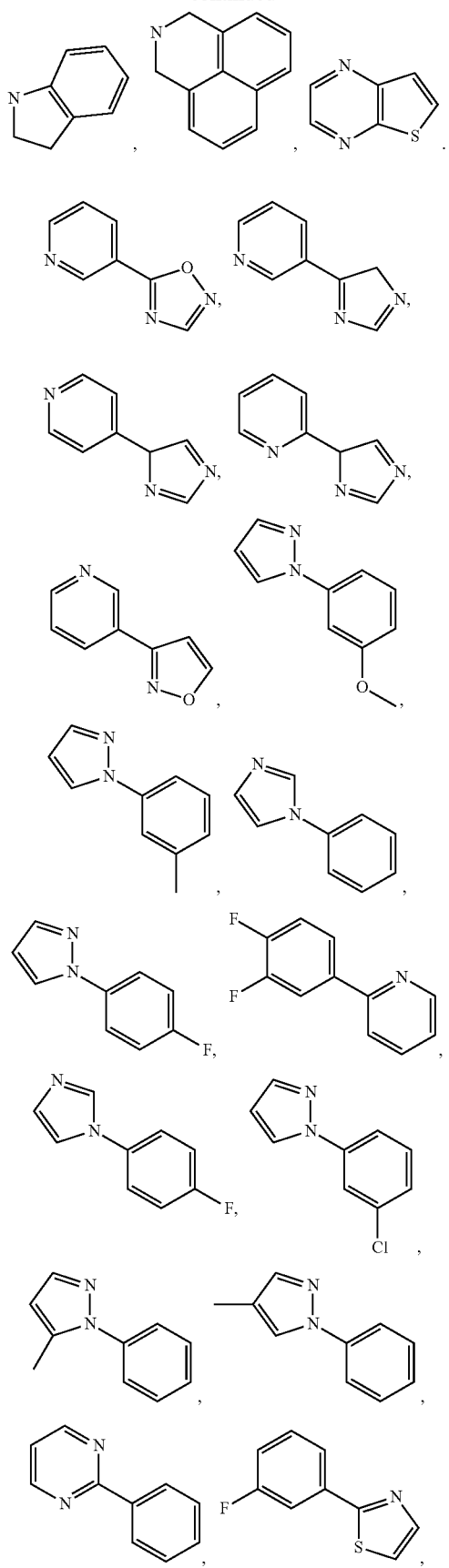
-continued
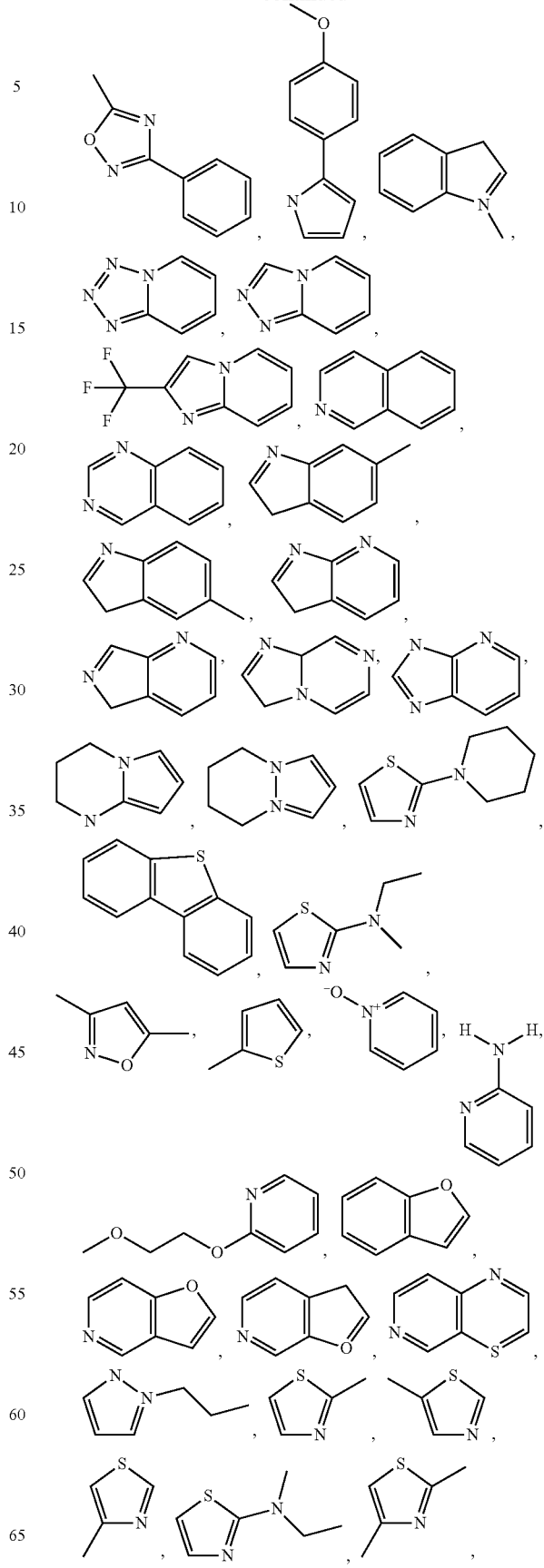

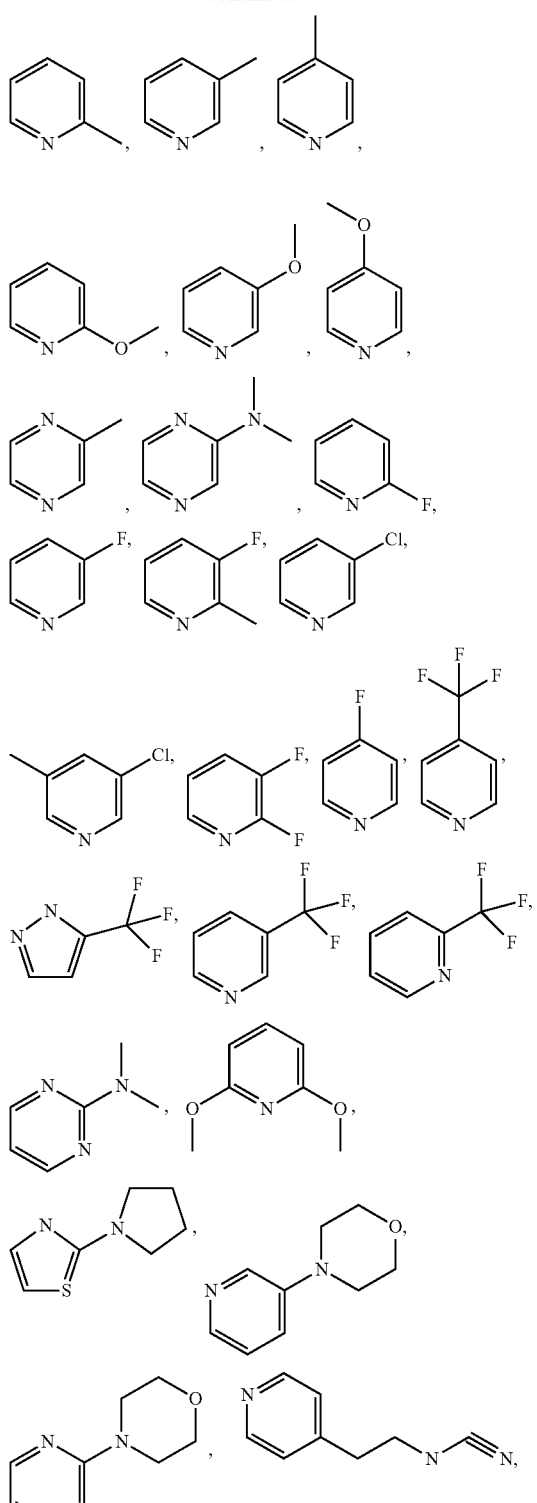

and the like.

As used herein, the term "cycloalkyl" refers to a saturated or partially saturated, monocyclic or fused or spiro polycyclic, carbocycle having from 3 to 24 ring atoms per ring. Illustrative examples of cycloalkyl groups include, but are not limited to, the following moieties:

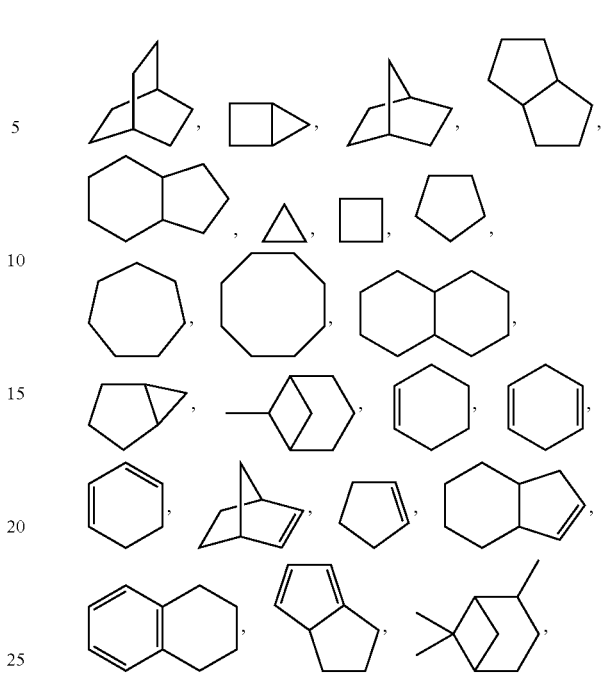

and the like.

As used herein, the term "heterocycloalkyl" refers to a monocyclic, or fused or spiro, polycyclic, ring structure that is saturated or partially saturated and has from 3 to 24 ring atoms per ring selected from C atoms and N, O, and S heteroatoms. Illustrative examples of heterocycloalkyl and substituted heterocycloalkyl groups include, but are not limited to:

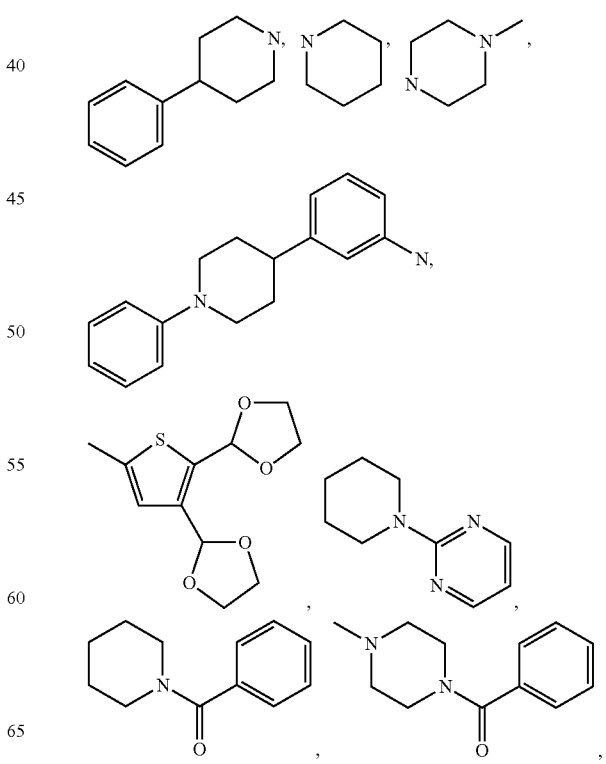

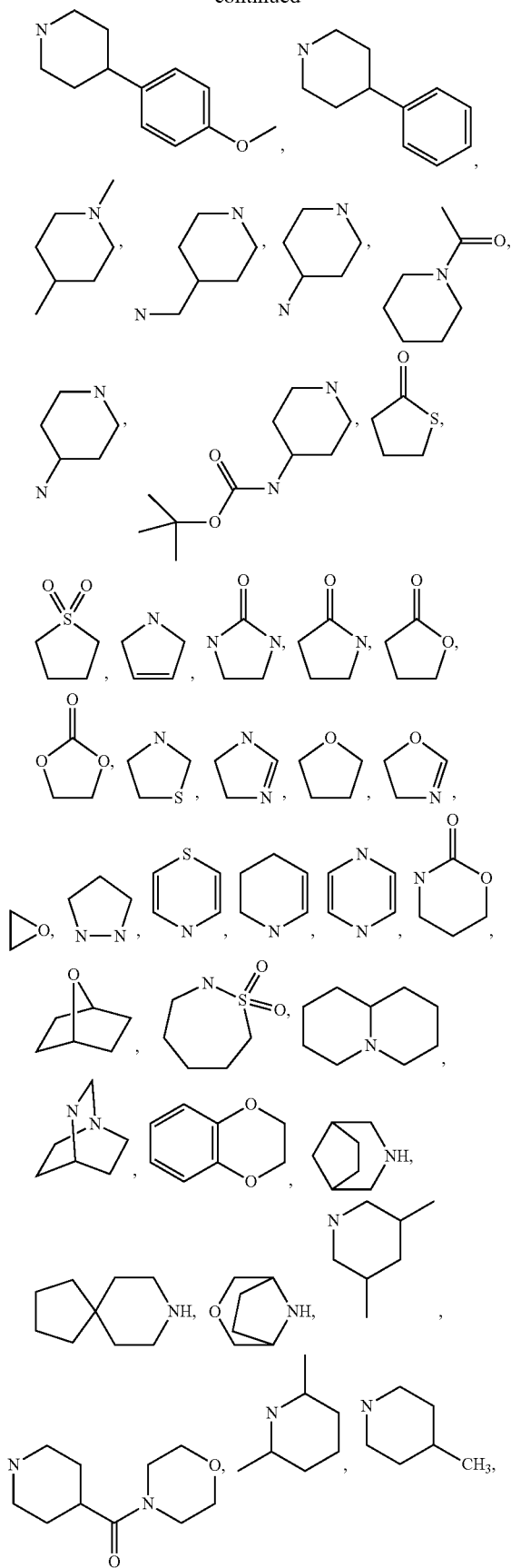
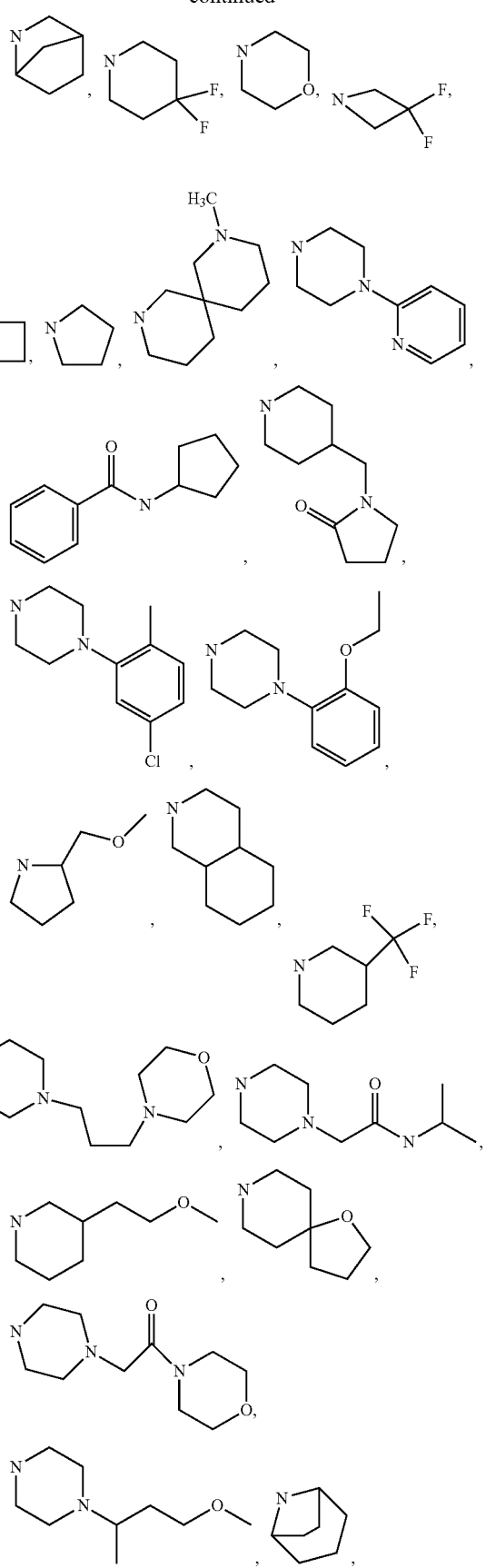

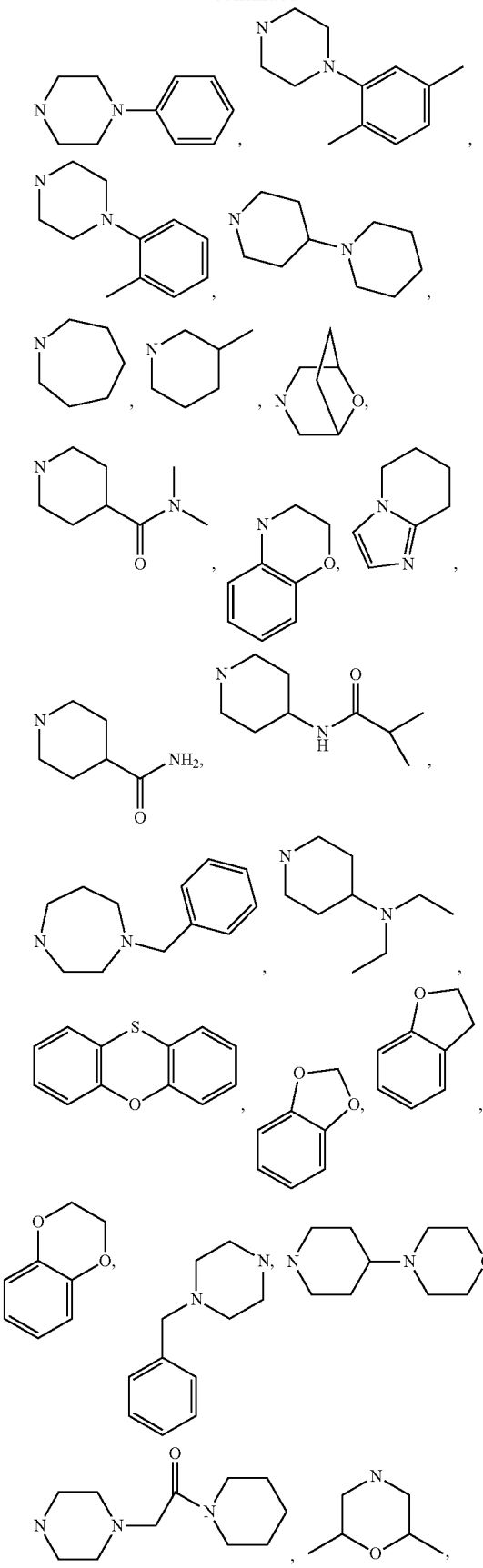
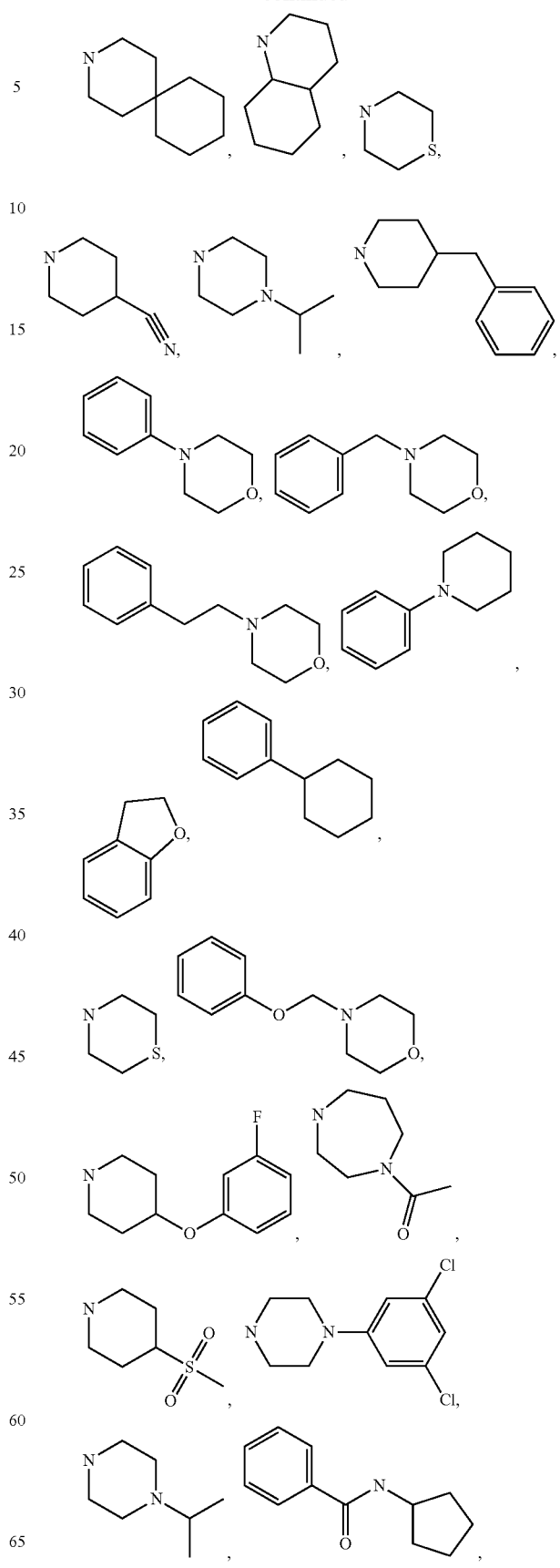

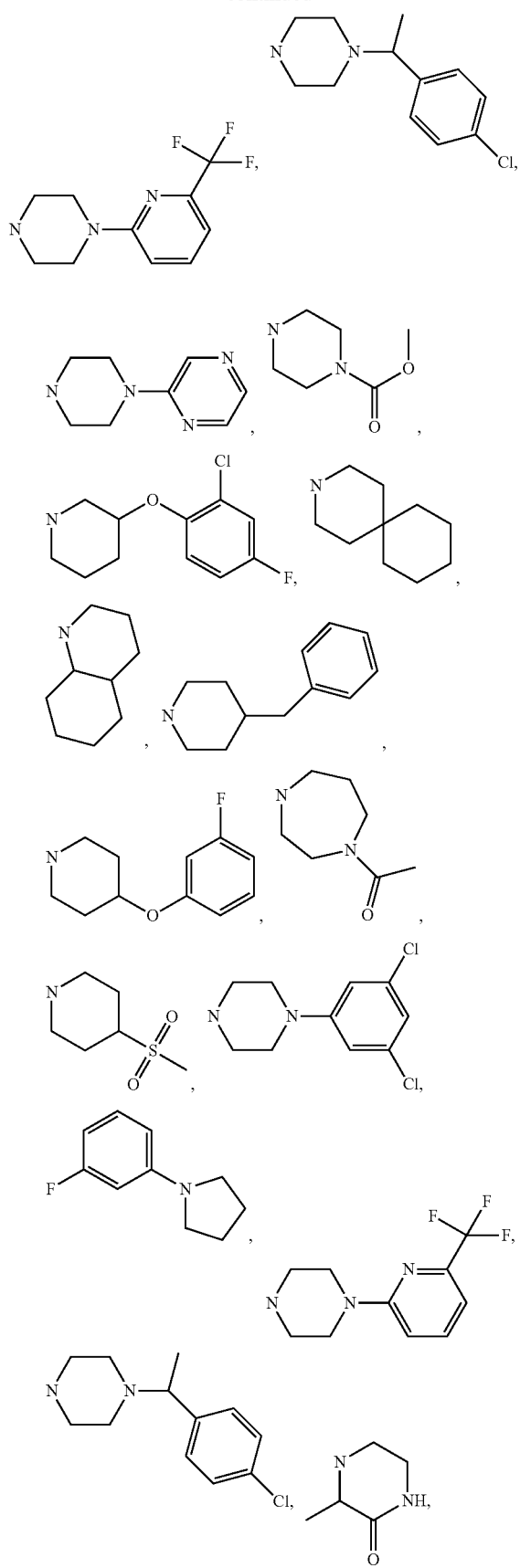
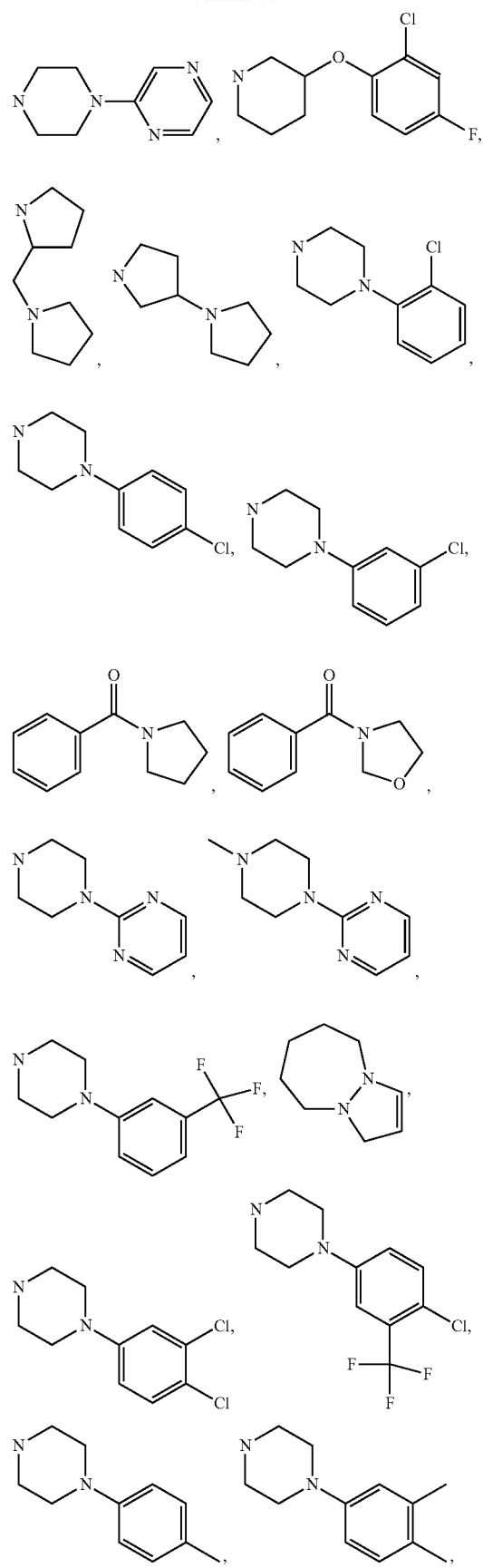

-continued

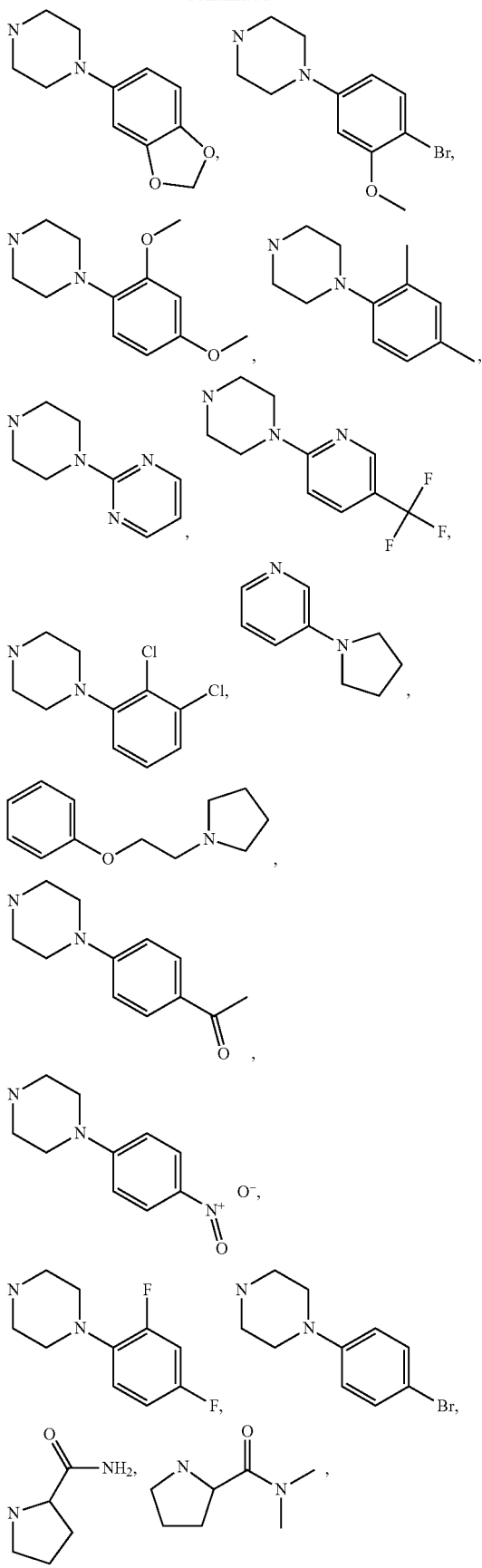

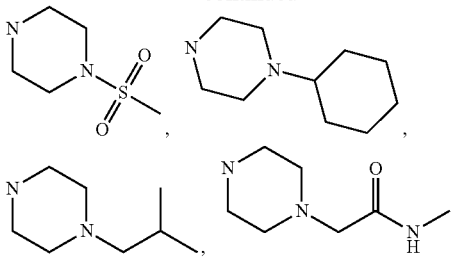

and the like.

Numerical ranges, as used herein, are intended to include sequential whole numbers. For example, a range expressed as "from 0 to 4" would include 0, 1, 2, 3 and 4.

As used herein, the term "substituted" means that the specified group or moiety bears one or more suitable substituents.

As used herein, the term "unsubstituted" means that the specified group bears no substituents.

As used herein, the term "optionally substituted" means that the specified group is unsubstituted or substituted by one or more substituents.

When a multifunctional moiety is shown, the point of attachment to the core is indicated by a line. For e.g. (cycloalkyloxy)alkyl- refers to alkyl being the point of attachment to the core while cycloalkyl is attached to alkyl via the oxy group.

The expression "adjunctive chemotherapeutic agent" generally refers to agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin. Other such adjunctive chemotherapeutic agents include those which inhibit nausea associated with administration of the chemotherapeutic agents, such as a 5-$HT_3$ receptor inhibitor (e.g., dolansetron, granisetron, or ondansetron), with or without dexamethasone.

The terms "chemotherapeutic agent" and "antineoplastic agent" generally refer to agents that treat, prevent, cure, heal, alleviate, relieve, alter, remedy, ameliorate, improve, or affect malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, cisplatin, carboplatin, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinvlastin, vincristine, and any combination of any of the foregoing. Additional such agents are described later.

It must be noted that, as used in the specification and the appended claims, the singular forms "a," "an" and "the" include plural referents unless the context clearly dictates otherwise.

When used as a therapeutic agent the inhibitors of the ROS kinase activities described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Such pharmaceutical excipients include, for example, the following: Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in dosage forms of the present invention.

The compounds of Formulas I and II can form salts which are also within the scope of this invention. Reference to a compound of the Formula herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66 (1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I and II, and salts, solvates, esters and prodrugs thereof, may exist in their tautomeric form (for example, as an amide or imino ether). All such tautomeric forms are contemplated herein as part of the present invention.

The compounds of Formula I and II may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I or II incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

Benefits of the present invention include oral administration of an optimal amount of a ROS inhibitor.

Benefits of the present invention include intravenous administration of an optimal amount of a ROS inhibitor.

Benefits of the present invention include intraperitoneal administration of an optimal amount of a ROS inhibitor.

Benefits of the present invention include intramural administration of an optimal amount of a ROS inhibitor.

Benefits of the present invention include intramuscular administration of an optimal amount of a ROS inhibitor.

Benefits of the present invention include subcutaneous administration of an optimal amount of a ROS inhibitor.

Benefits of the present invention include intra-tumor administration of an optimal amount of a ROS inhibitor.

Benefits of the present invention include intrathecal administration of an optimal amount of a ROS inhibitor.

Benefits of the present invention include subdural administration of an optimal amount of a ROS inhibitor.

Benefits of the present invention include periorbital administration of an optimal amount of a ROS inhibitor.

Based on these results, the present invention has important implications for the design of novel treatment strategies for patients with cancer, including leukemias and solid tumors such as glioblastoma, cholangiocarcinoma, and cell lung cancer (NSCLC), cardiovascular diseases, male infertility, inflammatory diseases, osteoporosis, atherosclerosis; irritable bowel syndrome and other conditions disclosed herein or that are known to those skilled in the art.

BRIEF DESCRIPTION OF THE DRAWINGS

FIG. 1: Xalkori/Crizotinib docked into a structural model of the ROS ATP binding site. Dashed yellow lines represent hydrogen bonds. The amino pyridine core forms hydrogen bonds with backbone atoms of the hinge residues Met2029 and Glu2030, while the piperidine group forms a salt bridge with Asp2033.

FIG. 2: A subset of small molecules that inhibited the in vitro catalytic activity of ROS, employing a substrate phosphorylation assay purchased from Cisbio. All compounds were evaluated for kinase inhibition using a high throughput screening platform for phospho-detection of kinase activity, employing a biotinylated peptide substrate and a specific anti-phospho peptide antibody. A 12 point dose response curve was generated to accurately assess $IC_{50}$ values. The concentration of Crizotimb producing a 50% inhibition of ROS kinase activity (i.e., $IC_{50}$) was 1.556 nM.

FIG. 3: Potency, selectivity and growth inhibitory effects of Xalkori in in vitro kinase and cell-based assays. Crizotinib inhibition as judged by three approaches: 1) inhibition of ROS enzymatic activity in vitro; 2) inhibition of a second unrelated receptor tyrosine kinase EGFR; and 3) growth inhibition of one cervical cancer cell line (HeLa) and four glioblastoma cells lines (U138, U118, LN18 and U87). U138 and U118 have been documented to express aberrant ROS (FIG-ROS fusion). The cell-based assay conditions measure cell proliferation/survival by Alamar blue staining.

DESCRIPTION OF THE PREFERRED EMBODIMENTS

An aspect of the present invention concerns a method to reduce the speed of, stop, or reverse the progression of abnormal cell growth using the a composition comprising therapeutically effective amount of a compound disclosed herein.

An aspect of the present invention concerns compounds disclosed herein.

An aspect of the present invention concerns a method to reduce the speed of, stop, or reverse the progression of abnormal cell growth using inhibitors of the ROS tyrosine kinase.

An aspect of the present invention concerns compounds which are or can be inhibitors of the ROS tyrosine kinase.

An aspect of the present invention concerns the use of an inhibitor of ROS kinase activities for the preparation of a medicament used in the treatment, prevention, inhibition or elimination of tumors resulted from abnormal cell growth in a mammal.

An aspect of the present invention concerns the use of an inhibitor of ROS kinase activities for the preparation of a medicament used in the treatment, prevention, inhibition or elimination of cancer.

An aspect of the present invention concerns the use of an inhibitor of ROS kinase activities for the preparation of a medicament used in the treatment, prevention, inhibition or elimination of cancer, where the cancer is selected from glioblastoma, cholangiocarcinoma, leukemia, lymphoma, ovarian cancer, breast cancer, uterine cancer, colon cancer, cervical cancer, lung cancer, non small cell lung cancer (NSCLC), prostate cancer, skin cancer, CNS cancer, bladder cancer, pancreatic cancer and Hodgkin's disease.

The present invention also describes one or more methods of synthesizing the compounds disclosed by the present invention.

The invention also describes one or more uses of the compounds of the present invention.

The invention also describes one or more uses of the compounds of the present invention with an adjunctive agent such as use with TNF, GCSF, or other chemotherapeutic agents.

The invention also describes one or more uses of the pharmaceutical compositions of the present invention.

An aspect of the present invention concerns the use as an inhibitor of ROS kinase activities for the preparation of a medicament used in the treatment of cardiovascular diseases.

An aspect of the present invention concerns the use as an inhibitor of ROS kinase activities for the preparation of a medicament used in the treatment of male infertility.

An aspect of the present invention concerns the use as an inhibitor of ROS kinase activities for the preparation of a medicament used in the treatment of disease or a condition caused by an elevated level of ROS or expression of the fusion protein FIG-ROS.

Such disease or condition is one or more selected from the group consisting of cancer, ovarian cancer, breast cancer, uterine cancer, colon cancer, cervical cancer, glioblastoma, cholangiocarcinoma, lung cancer, non small cell lung cancer (NSCLC), prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system (CNS).

The inventive compounds of the present invention can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, incorporated by reference herein.

More specifically, the compounds of the present invention can be useful in the treatment of a variety of cancers, including (but not limited to) the following: tumors of the central and peripheral nervous system, including glioblastoma, astrocytoma, neuroblastoma, glioma and schwannomas; carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; including cholangiocarcinoma, hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting ROS kinase activities in an animal, said method comprising administering to said animal a pharmaceutically acceptable amount of a compound of the invention to an animal in need thereof.

A further aspect of the invention is a pharmaceutical formulation comprising a compound of the invention.

Another embodiment of the invention comprises a pharmaceutical formulation of the invention, wherein the pharmaceutical formulation, upon administration to a human, results in a decrease in tumor burden.

Still another embodiment of the invention is a pharmaceutical formulation, further comprising one or more of an antineoplastic agent, a chemotherapeutic agent, or an adjunctive chemotherapeutic agent.

The pharmaceutical formulations of the invention may further comprise a therapeutic effective amount of an adjunctive chemotherapeutic agent.

The adjunctive chemotherapeutic agent may be an agent that modifies blood cell growth and maturation. Non-limiting examples of adjunctive chemotherapeutic agent are filgrastim, pegfilgrastim and erythropoietin.

The invention is also directed to a method of treating or preventing a disorder associated with excessive rate of growth of cells in a mammal comprising administering to the mammal an effective amount of the pharmaceutical formulation of the invention. Non-limiting examples of disorder include cancer or metastasis from malignant tumors.

Another aspect of the invention is a method of inhibiting tumor cell growth and rate of division in a mammal with cancer, or other disorder associated with abnormally dividing cells comprising administering to the mammal an effective amount of the pharmaceutical formulation of this invention.

Another embodiment of the invention is a method of treating bone pain due to excessive growth of a tumor or metastasis to bone in a mammal in need thereof comprising administering to the mammal an effective amount of the pharmaceutical formulation of this invention.

Still another embodiment of the invention is a method for administering a ROS-inhibitor-containing compound to a mammal in need thereof comprising administering to the mammal the pharmaceutical formulation of the invention. In one embodiment, the mammal is a human.

A further embodiment of the invention is a method of preparing a pharmaceutical formulation comprising mixing at least one pharmaceutically acceptable compound of Formula I and II, and, optionally, one or more pharmaceutically acceptable excipients or additives.

The invention is also directed to methods of synthesizing compounds of the present invention.

The present invention relates to inhibiting the ROS tyrosine kinase using particular molecules and pharmaceutically acceptable salts or isomers thereof.

The invention is directed to a method of inhibiting ROS using compounds as described herein and pharmaceutically acceptable salts or isomers thereof, and pharmaceutical compositions comprising one or more compounds as described herein and pharmaceutically acceptable salts or isomers thereof.

The invention is also directed to a method to reduce the speed of, stop, or reverse the progression of abnormal cell growth in mammals using compounds as described herein and pharmaceutically acceptable salts or isomers thereof, and pharmaceutical compositions comprising one or more compounds as described herein and pharmaceutically acceptable salts or isomers thereof.

One aspect of this invention is the provision of a method to reduce the speed of, stop, or reverse the progression of abnormal cell growth with compositions, kits, and antidotes for the ROS pathway in mammals having a compound of the formula I:

$$Ar^1—(CH_2)_m—(X)_m—Ar^2 \qquad I$$

wherein
Ar$^1$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O;
n is 0, 1, 2, or 3;
X is N, N(O), S, S(O), S(O)$_2$, O, or C(O);
m is 0 or 1;
Ar$^2$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O.

and pharmaceutically acceptable salts, solvates, esters, prodrugs or isomers thereof.

In the compounds of Formula I, the various moieties are independently selected.

The following embodiments are directed to a method using a compound of Formula I, as presented herein and further defined. For any moieties that are not specifically defined, the previous definitions control. Further, the moieties aryl, heteroaryl, and heterocycloalkyl in these embodiments can be independently unsubstituted or optionally substituted or optionally fused as described earlier.

An embodiment of the invention is the provision of a method using a compound of Formula I, where the various moieties are independently selected, Ar$^1$ is aryl, and n, m, z, X, and Ar$^2$ are as defined.

An embodiment of the invention is the provision of a method using a compound of Formula I, where the various moieties are independently selected, Ar$^1$ is heteroaryl, and n, m, z, X, and Ar$^2$ are as defined.

An embodiment of the invention is the provision of a method using a compound of Formula I, where the various moieties are independently selected, Ar$^1$ is (heteroaryl)alkyl, and n, m, z, X, and Ar$^2$ are as defined.

An embodiment of the invention is the provision of a method using a compound of Formula I, where the various moieties are independently selected, Ar$^1$ is arylalkyl, and n, m, z, X, and Ar$^2$ are as defined.

An embodiment of the invention is the provision of a method using a compound of Formula I, where the various moieties are independently selected, Ar$^1$, n, m, z, and Ar$^2$ are as defined and X is N.

An embodiment of the invention is the provision of a method using a compound of Formula I, where the various moieties are independently selected, Ar$^1$, n, m, z, and Ar$^2$ are as defined and X is N(O).

An embodiment of the invention is the provision of a method using a compound of Formula I, where the various moieties are independently selected, Ar$^1$, n, m, z, and Ar$^2$ are as defined and X is O.

An embodiment of the invention is the provision of a method using a compound of Formula I, where the various moieties are independently selected, Ar$^1$, n, m, z, and Ar$^2$ are as defined and X is C(O).

An embodiment of the invention is the provision of a method using a compound of Formula I, where the various moieties are independently selected, Ar$^1$, m, z, X, and Ar$^2$ are as defined and n is 0.

An embodiment of the invention is the provision of a method using a compound of Formula I, where the various moieties are independently selected, Ar$^1$, m, z, X, and Ar$^2$ are as defined and n is 1.

An embodiment of the invention is the provision of a method using a compound of Formula I, where the various moieties are independently selected, Ar$^1$, m, z, X, and Ar$^2$ are as defined and n is 2.

An embodiment of the invention is the provision of a method using a compound of Formula I, where the various moieties are independently selected, Ar$^1$, n, z, X, and Ar$^2$ are as defined and m is 0.

An embodiment of the invention is the provision of a method using a compound of Formula I, where the various moieties are independently selected, Ar$^1$, n, z, X, and Ar$^2$ are as defined and m is 1.

An embodiment of the invention is the provision of a method using a compound of Formula I, where the various moieties are independently selected, Ar$^1$, n, z, X, and Ar$^2$ are as defined and m is 2.

An embodiment of the invention is the provision of a method using a compound of Formula I, where the various moieties are independently selected, Ar¹, n, z, X, and m are as defined and Ar² is

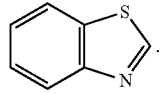

An embodiment of the invention is the provision of a method using a compound of Formula I, where the various moieties are independently selected, Ar¹, n, z, X, and m are as defined and Ar² is

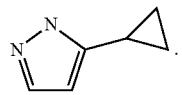

An embodiment of the invention is the provision of a method using a compound of Formula I, where the various moieties are independently selected, Ar², n, z, X, and m are as defined and Ar¹ is

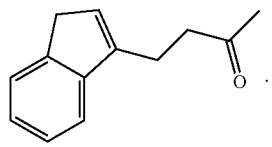

An embodiment of the invention is the provision of a method using a compound of Formula I, where the various moieties are independently selected, Ar², z, X, and m are as defined, n is 0, and Ar¹ is

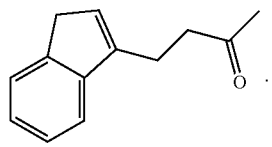

An embodiment of the invention is the provision of a method using a compound of Formula I, where the various moieties are independently selected, Ar², z, X, and m are as defined, n is 1, and Ar¹ is

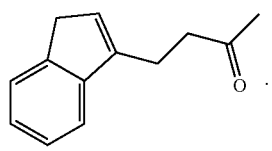

An embodiment of the invention is the provision of a method using a compound of Formula I, where the various moieties are independently selected, Ar², z, n, and m are as defined, X is N, and Ar¹ is

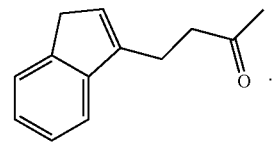

An embodiment of the invention is the provision of a method using a compound of Formula I, where the various moieties are independently selected, n, z, X, and m are as defined, Ar¹ is

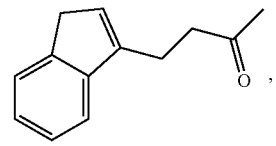

and Ar² is benzene wherein each hydrogen atom on said benzene is un-substituted or independent substituted with one or more substituents which can be the same or different and are independently selected from the group consisting of halo, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z, X, and m are as defined, n is 0, Ar¹ is

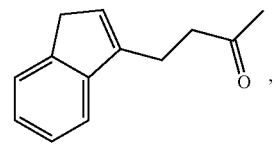

and Ar² is benzene wherein each hydrogen atom on said benzene is un-substituted or independent substituted with one or more substituents which can be the same or different and are independently selected from the group consisting of halo, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z, X, and m are as defined, n is 1, Ar¹ is

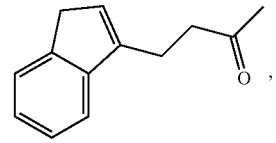

and Ar² is benzene wherein each hydrogen atom on said benzene is un-substituted or independent substituted with one or more substituents which can be the same or different and are independently selected from the group consisting of halo, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, n, z and m are as defined, X is N, Ar$^1$ is

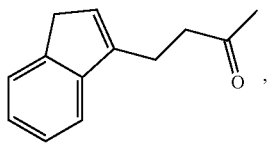

and Ar$^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z and m are as defined, X is N, n is 0, Ar$^1$ is

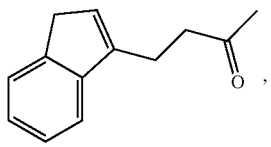

and Ar$^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z and m are as defined, X is N, n is 1, Ar$^1$ is

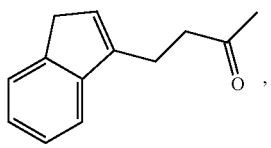

and Ar$^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, Ar$^2$, n, z, X, and m are as defined and Ar$^1$ is

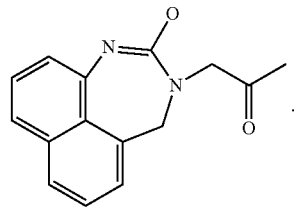 [SMILES: CC(=O)CN1Cc2cccc3cccc(c23)N=C1O]

An embodiment of the invention is the provision of a method using a compound of Formula I, where the various moieties are independently selected, Ar$^2$, z, X, and m are as defined, n is 0, and Ar$^1$ is

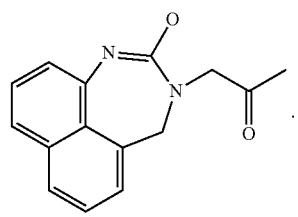 [SMILES: CC(=O)CN1Cc2cccc3cccc(c23)N=C1O]

An embodiment of the invention is the provision of a method using a compound of Formula I, where the various moieties are independently selected, Ar$^2$, z, X, and m are as defined, n is 1, and Ar$^1$ is

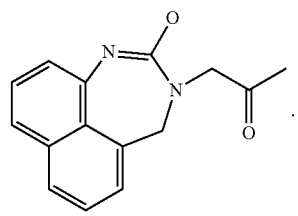 [SMILES: CC(=O)CN1Cc2cccc3cccc(c23)N=C1O]

An embodiment of the invention is the provision of a method using a compound of Formula I, where the various moieties are independently selected, Ar$^2$, z, n, and m are as defined, X is N, and Ar$^1$ is

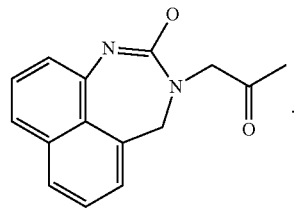 [SMILES: CC(=O)CN1Cc2cccc3cccc(c23)N=C1O]

An embodiment of the invention is the provision of a method using a compound of Formula I, where the various moieties are independently selected, n, z, X, and m are as defined, $Ar^1$ is

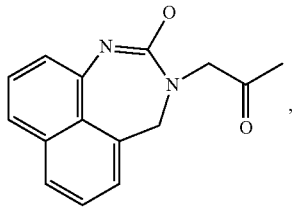 [SMILES: CC(=O)CN1Cc2cccc3cccc(c23)N=C1O]

and $Ar^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z, X, and m are as defined, n is 0, $Ar^1$ is

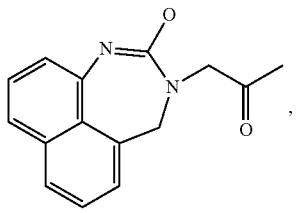 [SMILES: CC(=O)CN1Cc2cccc3cccc(c23)N=C1O]

and $Ar^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z, X, and m are as defined, n is 1, $Ar^1$ is

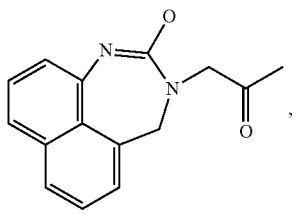 [SMILES: CC(=O)CN1Cc2cccc3cccc(c23)N=C1O]

and $Ar^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, n, z and m are as defined, X is N, $Ar^1$ is

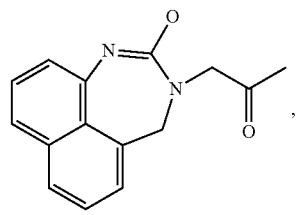 [SMILES: CC(=O)CN1Cc2cccc3cccc(c23)N=C1O]

and $Ar^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z and m are as defined, X is N, n is 0, $Ar^1$ is

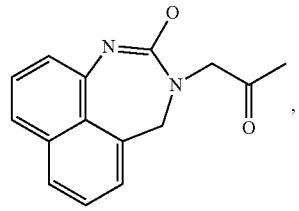 [SMILES: CC(=O)CN1Cc2cccc3cccc(c23)N=C1O]

and $Ar^2$ is benzene wherein each hydrogen atom on said benzene is un-substituted or independent substituted with one or more substituents which can be the same or different and are independently selected from the group consisting of halo, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

An embodiment of the invention is the provision of a method using a compound of Formula I, where the various moieties are independently selected, z and m are as defined, X is N, n is 1, $Ar^1$ is

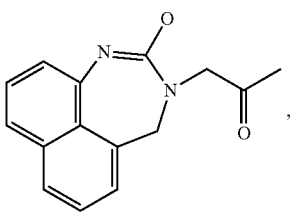 [SMILES: CC(=O)CN1Cc2cccc3cccc(c23)N=C1O]

and Ar² is benzene wherein each hydrogen atom on said benzene is un-substituted or independent substituted with one or more substituents which can be the same or different and are independently selected from the group consisting of halo, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

One aspect of this invention is the provision a method of reducing the speed of, stopping, or reversing progression of abnormal cell growth in a mammal, comprising administering to the mammal a composition comprising therapeutically effective amount of a compound of formula II:

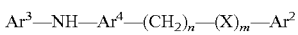

Ar³—NH—Ar⁴—(CH₂)$_n$—(X)$_m$—Ar²     II wherein
n is 0 or 1; and
X is N;
m is 0 or 1;
Ar² is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl) amino-, -cycloalkyl, -heterocycloalkyl, -aryl, —C(O)-alkyl, —C(O)-aryl, —S(O)-aryl, —NH—C(O)—alkyl, —NH—C(O)-aryl and heteroaryl, with the proviso that no two adjacent ring heteroatoms on a ring are both S or both O;

Ar³ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl, heteroaryl, arylalkyl or heteroarylalkyl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl) amino-, -cycloalkyl, -heterocycloalkyl, -aryl, —C(O)-alkyl, —C(O)-aryl, —S(O)-aryl, —NH—C(O)—alkyl, —NH—C(O)-aryl and heteroaryl, with the proviso that no two adjacent ring heteroatoms on a ring are both S or both O; and Ar⁴ is aryl, heteroaryl, arylalkyl or heteroarylalkyl, wherein the heteroatom of each of said heteroaryl and heteroaryl independently numbers 1, 2 or 3, and is independently selected from N, S or O, and pharmaceutically acceptable salts, solvates, esters, prodrugs or isomers thereof.

In the compounds of Formula II, the various moieties are independently selected.

The following embodiments are directed to a method using a compound of Formula II, as presented herein and further defined. For any moieties that are not specifically defined, the previous definitions control. Further, the moieties aryl, heteroaryl, and heterocycloalkyl in these embodiments can be independently unsubstituted or optionally substituted or optionally fused as described earlier.

An embodiment of the invention is the provision of a method using a compound of Formula II, where the various moieties are independently selected, Ar² is aryl, and n, m, z, X, Ar³ and Ar⁴ are as defined.

An embodiment of the invention is the provision of a method using a compound of Formula II, where the various moieties are independently selected, Ar² is aryl, and n, m, z, X, Ar³ and Ar⁴ and Ar⁴ are as defined.

An embodiment of the invention is the provision of a method using a compound of Formula II, where the various moieties are independently selected, Ar² is aryl, and n, m, z, X, Ar³ and Ar⁴ are as defined.

An embodiment of the invention is the provision of a method using a compound of Formula II, where the various moieties are independently selected, Ar² is aryl, and n, m, z, X, Ar³ and Ar⁴ are as defined.

An embodiment of the invention is the provision of a method using a compound of Formula II, where the various moieties are independently selected, Ar³ is aryl, and n, m, z, X, Ar² and Ar⁴ are as defined.

An embodiment of the invention is the provision of a method using a compound of Formula II, where the various moieties are independently selected, Ar³ is heteroaryl, and n, m, z, X, Ar² and Ar⁴ are as defined.

An embodiment of the invention is the provision of a method using a compound of Formula II, where the various moieties are independently selected, Ar³ is (heteroaryl)alkyl, and n, m, z, X, Ar² and Ar⁴ are as defined.

An embodiment of the invention is the provision of a method using a compound of Formula II, where the various moieties are independently selected, Ar³ is arylalkyl, and n, m, z, X, Ar² and Ar⁴ are as defined.

An embodiment of the invention is the provision of a method using a compound of Formula II, where the various moieties are independently selected, Ar⁴ is aryl, and n, m, z, X, Ar² and Ar³ are as defined.

An embodiment of the invention is the provision of a method using a compound of Formula II, where the various moieties are independently selected, Ar⁴ is heteroaryl, and n, m, z, X, Ar² and Ar³ are as defined.

An embodiment of the invention is the provision of a method using a compound of Formula II, where the various moieties are independently selected, Ar⁴ is arylalkyl, and n, m, z, X, Ar² and Ar³ are as defined.

An embodiment of the invention is the provision of a method using a compound of Formula II, where the various moieties are independently selected, Ar⁴ is heteroarylalkyl, and n, m, z, X, Ar² and Ar³ are as defined.

An embodiment of the invention is the provision of a method using a compound of Formula II, where the various moieties are independently selected, Ar², Ar³, m, z, X, and Ar⁴ are as defined and n is 0.

An embodiment of the invention is the provision of a method using a compound of Formula II, where the various moieties are independently selected, Ar², Ar³, m, z, X, and Ar⁴ are as defined and n is 1.

An embodiment of the invention is the provision of a method using a compound of Formula II, where the various moieties are independently selected, Ar², Ar³, n, z, X, and Ar⁴ are as defined and m is 0.

An embodiment of the invention is the provision of a method using a compound of Formula II, where the various moieties are independently selected, Ar², Ar³, n, z, X, and Ar⁴ are as defined and m is 1.

An embodiment of the invention is the provision of a method using a compound of Formula II, where the various moieties are independently selected, Ar³, Ar⁴, n, z, X, and m are as defined and Ar² is aryl, heteroaryl, arylalkyl or heteroarylalkyl, wherein the heteroatom of each of said heteroaryl and heteroaryl independently numbers 1, 2 or 3, and is independently selected from N, S or O.

An embodiment of the invention is the provision of a method using a compound of Formula II, where the various moieties are independently selected, Ar³, Ar⁴, n, z, X, and m are as defined and Ar² is

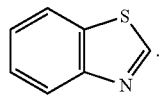

An embodiment of the invention is the provision of a method using a compound of Formula II, where the various moieties are independently selected, Ar³, Ar⁴, n, z, X, and m are as defined and Ar² is

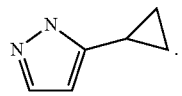

An embodiment of the invention is the provision of a method using a compound of Formula II, where the various moieties are independently selected, Ar², Ar⁴, n, z, X, and m are as defined and Ar³ is aryl, heteroaryl, arylalkyl, heteroarylalkyl, cycloalkyl, or heterocycloalkyl wherein the heteroatom of each of said heteroaryl, heteroarylalkyl, and heterocycloalkyl independently numbers 1, 2 or 3, and is independently selected from N, S or O.

An embodiment of the invention is the provision of a method using a compound of Formula II, where the various moieties are independently selected, Ar⁴, n, z, X, and m are as defined, Ar² is aryl, heteroaryl, arylalkyl or heteroarylalkyl, wherein the heteroatom of each of said heteroaryl and heteroaryl independently numbers 1, 2 or 3, and is independently selected from N, S or O, and Ar³ is aryl, heteroaryl, arylalkyl, heteroarylalkyl, cycloalkyl, or heterocycloalkyl wherein the heteroatom of each of said heteroaryl, heteroarylalkyl, and heterocycloalkyl independently numbers 1, 2 or 3, and is independently selected from N, S or O.

An embodiment of the invention is the provision of a method using a compound of Formula II, where the various moieties are independently selected, Ar², Ar⁴, n, z, X, and m are as defined and Ar³ is

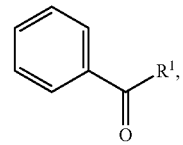

wherein R¹ is cycloalkyl, aryl, heterocycloalkyl, heteroaryl, alkyl, alkenyl, alkynyl, (aryl)alkyl-, (heteroaryl)alkyl- or (heterocycloalkyl)alkyl-.

An embodiment of the invention is the provision of a method using a compound of Formula II, where the various moieties are independently selected, Ar², Ar⁴, n, z, X, and m are as defined and Ar³ is

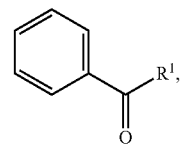

wherein R¹ is

An embodiment of the invention is the provision of a method using a compound of Formula II, where the various moieties are independently selected, Ar², Ar⁴, n, z, X, and m are as defined and Ar³ is

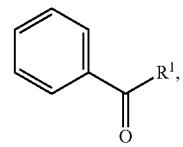

wherein R¹ is

An embodiment of the invention is the provision of a method using a compound of Formula II, where the various moieties are independently selected, Ar², Ar⁴, n, z, X, and m are as defined and Ar³ is

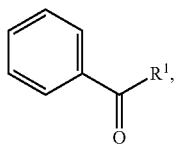

wherein $R^1$ is

An embodiment of the invention is the provision of a method using a compound of Formula II, where the various moieties are independently selected, $Ar^2$, $Ar^4$, n, z, X, and m are as defined and $Ar^3$ is

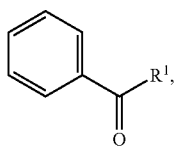

wherein $R^1$ is

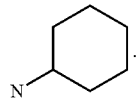

An embodiment of the invention is the provision of a method using a compound of Formula II, where the various moieties are independently selected, $Ar^2$, $Ar^4$, n, z, X, and m are as defined and $Ar^3$ is

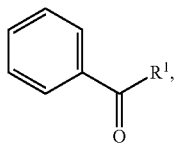

wherein $R^1$ is

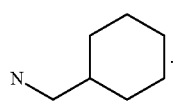

An embodiment of the invention is the provision of a method using a compound of Formula II, where the various moieties are independently selected, $Ar^2$, $Ar^4$, n, z, X, and m are as defined and $Ar^3$ is

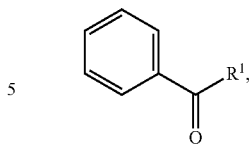

wherein $R^1$ is

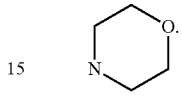

An embodiment of the invention is the provision of a method using a compound of Formula II, where the various moieties are independently selected, $Ar^4$, n, z, X, and m are as defined, $Ar^2$ is

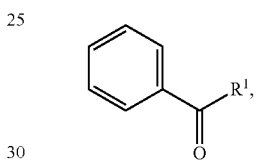

and $Ar^3$ is

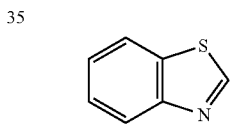

wherein $R^1$ is cycloalkyl, aryl, heterocycloalkyl, heteroaryl, alkyl, alkenyl, alkynyl, (aryl)alkyl-, (heteroaryl)alkyl- or (heterocycloalkyl)alkyl-.

An embodiment of the invention is the provision of a method using a compound of Formula II, where the various moieties are independently selected, $Ar^4$, n, z, X, and m are as defined, $Ar^2$ is

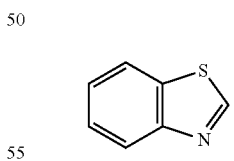

and $Ar^3$ is

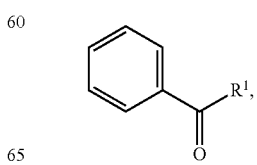

wherein $R^1$

An embodiment of the invention is the provision of a method using a compound of Formula II, where the various moieties are independently selected, $Ar^4$, n, z, X, and m are as defined, $Ar^2$ is

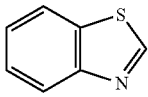

and $Ar^3$ is

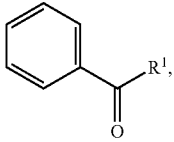

wherein $R^1$

An embodiment of the invention is the provision of a method using a compound of Formula II, where the various moieties are independently selected, $Ar^4$, n, z, X, and m are as defined, $Ar^2$ is

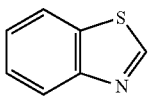

and $Ar^3$ is

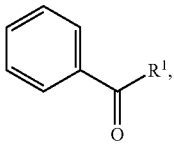

wherein $R^1$

An embodiment of the invention is the provision of a method using a compound of Formula II, where the various moieties are independently selected, $Ar^4$, n, z, X, and m are as defined, $Ar^2$ is

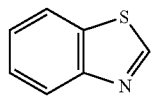

and $Ar^3$ is

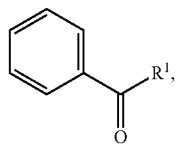

wherein $R^1$

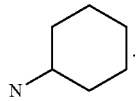

An embodiment of the invention is the provision of a method using a compound of Formula II, where the various moieties are independently selected, $Ar^4$, n, z, X, and m are as defined, $Ar^2$ is

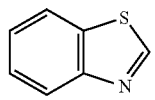

and $Ar^3$ is

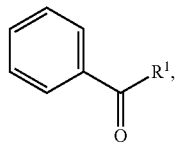

wherein $R^1$

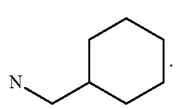

An embodiment of the invention is the provision of a method using a compound of Formula II, where the various moieties are independently selected, $Ar^4$, n, z, X, and m are as defined, $Ar^2$ is

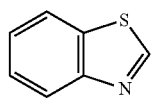

and Ar³ is

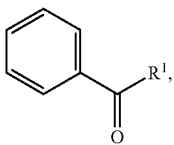

wherein R¹

An embodiment of the invention is the provision of a method using a compound of Formula II, where the various moieties are independently selected, Ar⁴, n, z, X, and m are as defined, Ar² is

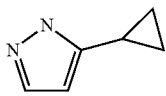

and Ar³ is

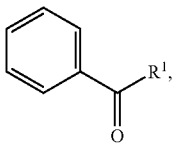

wherein R¹ is cycloalkyl, aryl, heterocycloalkyl, heteroaryl, alkyl, alkenyl, alkynyl, (aryl)alkyl-, (heteroaryl)alkyl- or (heterocycloalkyl)alkyl-.

An embodiment of the invention is the provision of a method using a compound of Formula II, where the various moieties are independently selected, Ar⁴, n, z, X, and m are as defined, Ar² is

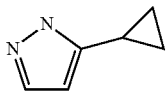

and Ar³ is

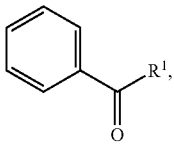

wherein R¹

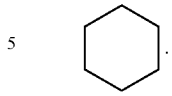

An embodiment of the invention is the provision of a method using a compound of Formula II, where the various moieties are independently selected, Ar⁴, n, z, X, and m are as defined, Ar² is

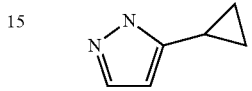

and Ar³ is

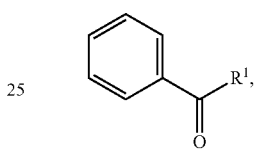

wherein R¹

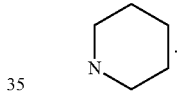

An embodiment of the invention is the provision of a method using a compound of Formula II, where the various moieties are independently selected, Ar⁴, n, z, X, and m are as defined, Ar² is

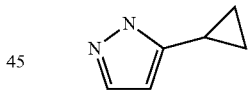

and Ar³ is

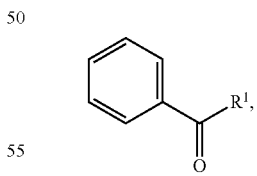

wherein R¹

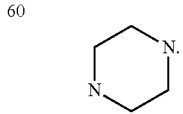

An embodiment of the invention is the provision of a method using a compound of Formula II, where the various moieties are independently selected, Ar⁴, n, z, X, and m are as defined, Ar² is

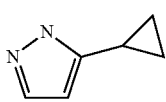

and Ar³ is

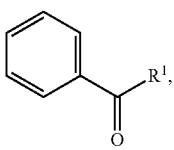

wherein R¹

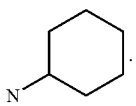

An embodiment of the invention is the provision of a method using a compound of Formula II, where the various moieties are independently selected, Ar⁴, n, z, X, and m are as defined, Ar² is

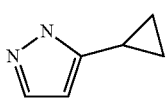

and Ar³ is

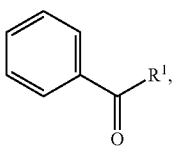

wherein R¹

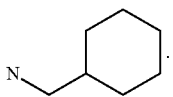

An embodiment of the invention is the provision of a method using a compound of Formula II, where the various moieties are independently selected, Ar⁴, n, z, X, and m are as defined, Ar² is

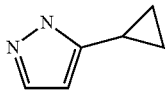

and Ar³ is

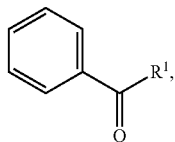

wherein R¹

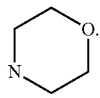

An embodiment of the invention is the provision of a method using a compound of Formula II, where the various moieties are independently selected, Ar², Ar³, n, z, X, and m are as defined, wherein Ar⁴ is heteroaryl and the heteroatom of each of said heteroaryl is N and independently numbers 1, 2 or 3, further wherein the atoms of said heteroaryl is unsubstituted or independently substituted with halo or alkyl.

An embodiment of the invention is the provision of a method using a compound of Formula II, where the various moieties are independently selected, Ar², Ar³, n, z, X, and m are as defined, wherein Ar⁴ is

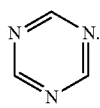

An embodiment of the invention is the provision of a method using a compound of Formula II, where the various moieties are independently selected, Ar², Ar³, n, z, X, and m are as defined, wherein Ar⁴ is

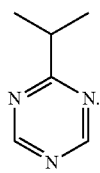

An embodiment of the invention is the provision of a method using a compound of Formula II, where the various moieties are independently selected, Ar², Ar³, n, z, X, and m are as defined, wherein Ar⁴ is

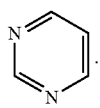

An embodiment of the invention is the provision of a method using a compound of Formula II, where the various moieties are independently selected, Ar², Ar³, n, z, X, and m are as defined, wherein Ar⁴ is

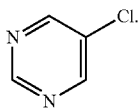

An embodiment of the invention is the provision of a method using a compound of Formula II, where the various moieties are independently selected, $Ar^3$, n, z, X, and m are as defined, wherein $Ar^2$ is

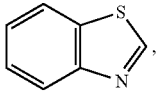

and $Ar^4$ is heteroaryl and the heteroatom of each of said heteroaryl is N and independently numbers 1, 2 or 3, further wherein the atoms of said heteroaryl is unsubstituted or independently substituted with halo or alkyl.

An embodiment of the invention is the provision of a method using a compound of Formula II, where the various moieties are independently selected, $Ar^3$, n, z, X, and m are as defined, wherein $Ar^2$ is

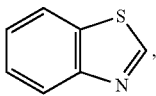

and $Ar^4$ is

An embodiment of the invention is the provision of a method using a compound of Formula II, where the various moieties are independently selected, $Ar^3$, n, z, X, and m are as defined, wherein $Ar^2$ is

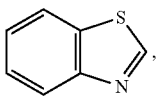

and $Ar^4$ is

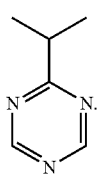

An embodiment of the invention is the provision of a method using a compound of Formula II, where the various moieties are independently selected, $Ar^3$, n, z, X, and m are as defined, wherein $Ar^2$ is

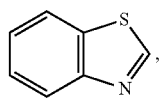

and $Ar^4$ is

An embodiment of the invention is the provision of a method using a compound of Formula II, where the various moieties are independently selected, $Ar^3$, n, z, X, and m are as defined, wherein $Ar^2$ is

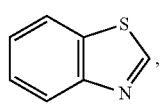

and $Ar^4$ is

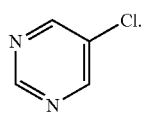

An embodiment of the invention is the provision of a method using a compound of Formula II, where the various moieties are independently selected, $Ar^3$, n, z, X, and m are as defined, wherein $Ar^2$ is

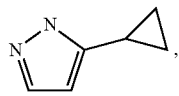

and $Ar^4$ is heteroaryl and the heteroatom of each of said heteroaryl is N and independently numbers 1, 2 or 3, further wherein the atoms of said heteroaryl is unsubstituted or independently substituted with halo or alkyl.

An embodiment of the invention is the provision of a method using a compound of Formula II, where the various moieties are independently selected, $Ar^3$, n, z, X, and m are as defined, wherein $Ar^2$ is

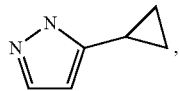

and $Ar^4$ is

An embodiment of the invention is the provision of a method using a compound of Formula II, where the various moieties are independently selected, Ar³, n, z, X, and m are as defined, wherein Ar² is

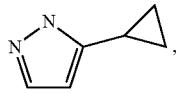

and Ar⁴ is

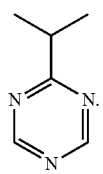

An embodiment of the invention is the provision of a method using a compound of Formula II, where the various moieties are independently selected, Ar³, n, z, X, and m are as defined, wherein Ar² is

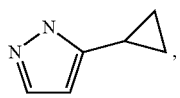

and Ar⁴ is

An embodiment of the invention is the provision of a method using a compound of Formula II, where the various moieties are independently selected, Ar³, n, z, X, and m are as defined, wherein Ar² is

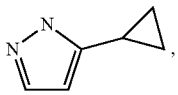

and Ar⁴ is

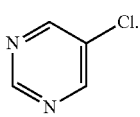

In another embodiment, the invention is further illustrated by the compounds shown in Table 1.

TABLE 1

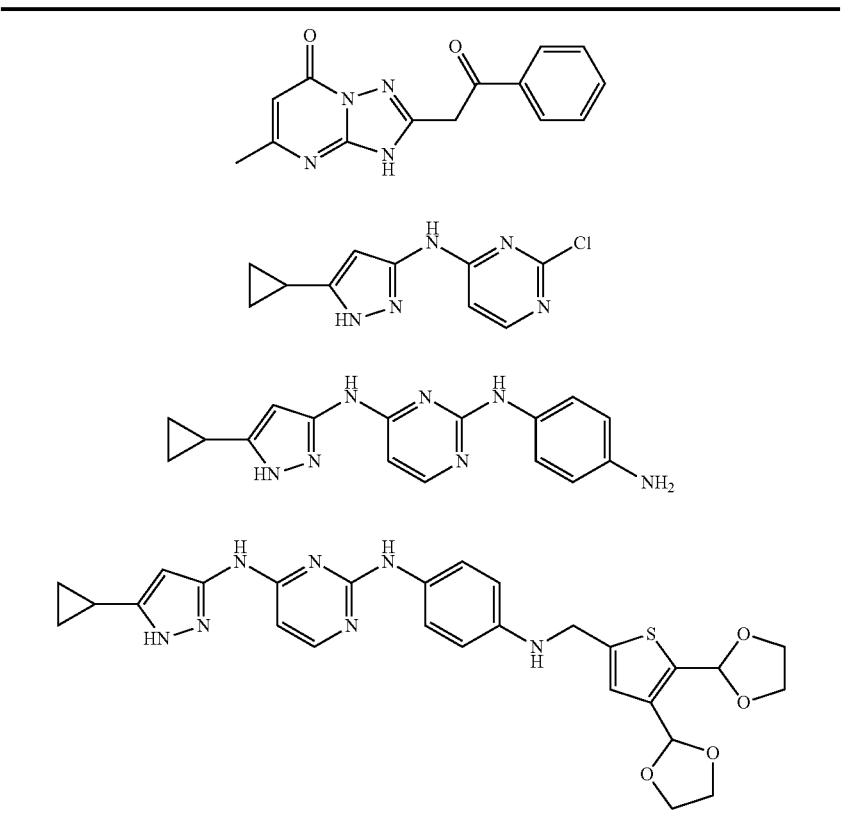

TABLE 1-continued
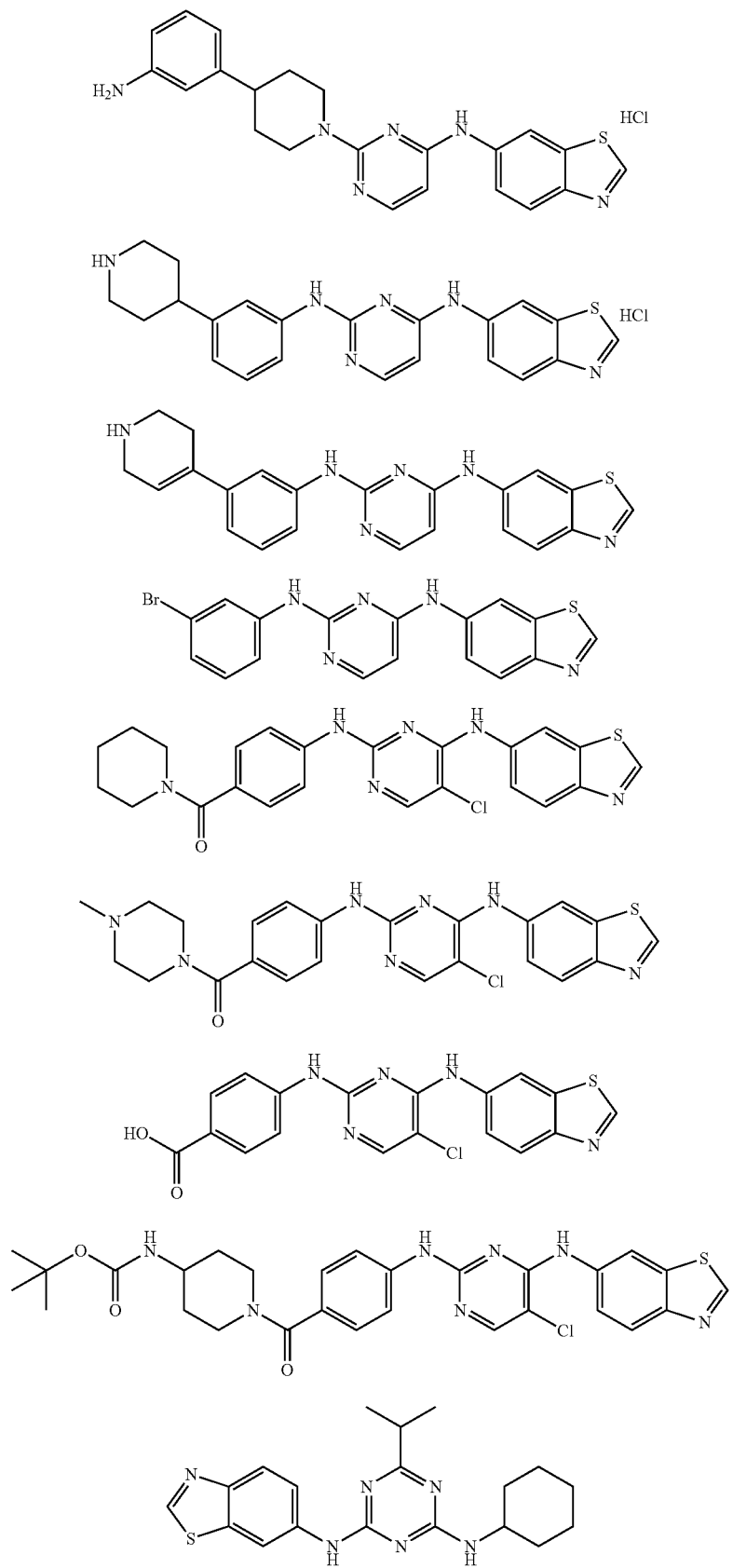

TABLE 1-continued
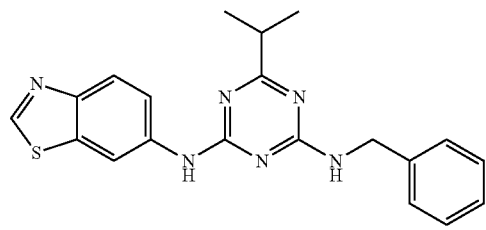 [SMILES: CC(C)c1nc(NCc2ccccc2)nc(Nc2ccc3ncsc3c2)n1]
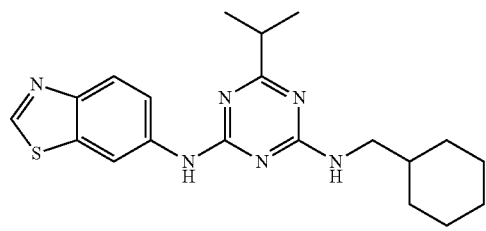 [SMILES: CC(C)c1nc(NCC2CCCCC2)nc(Nc2ccc3ncsc3c2)n1]
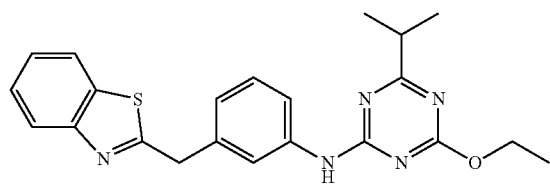 [SMILES: CCOc1nc(Nc2cccc(Cc3nc4ccccc4s3)c2)nc(C(C)C)n1]
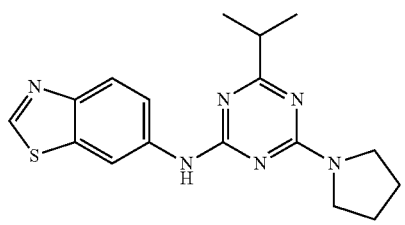 [SMILES: CC(C)c1nc(Nc2ccc3ncsc3c2)nc(N2CCCC2)n1]
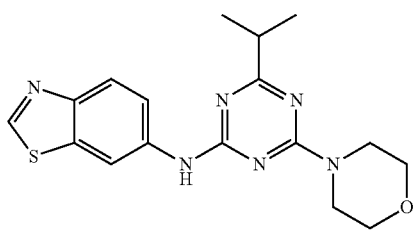 [SMILES: CC(C)c1nc(Nc2ccc3ncsc3c2)nc(N2CCOCC2)n1]
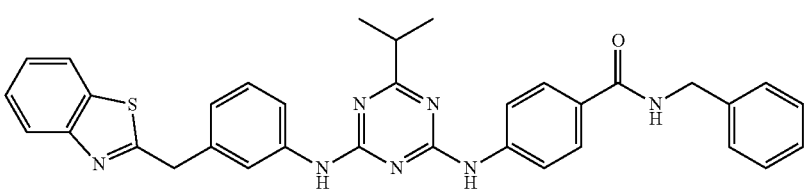 [SMILES: CC(C)c1nc(Nc2ccc(C(=O)NCc3ccccc3)cc2)nc(Nc2cccc(Cc3nc4ccccc4s3)c2)n1]
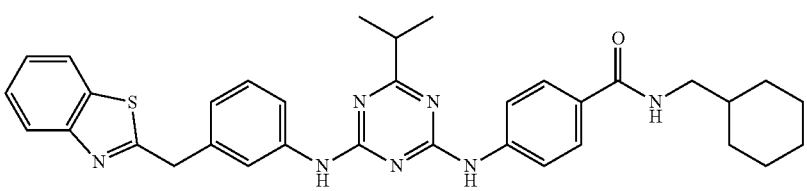 [SMILES: CC(C)c1nc(Nc2ccc(C(=O)NCC3CCCCC3)cc2)nc(Nc2cccc(Cc3nc4ccccc4s3)c2)n1]

TABLE 1-continued
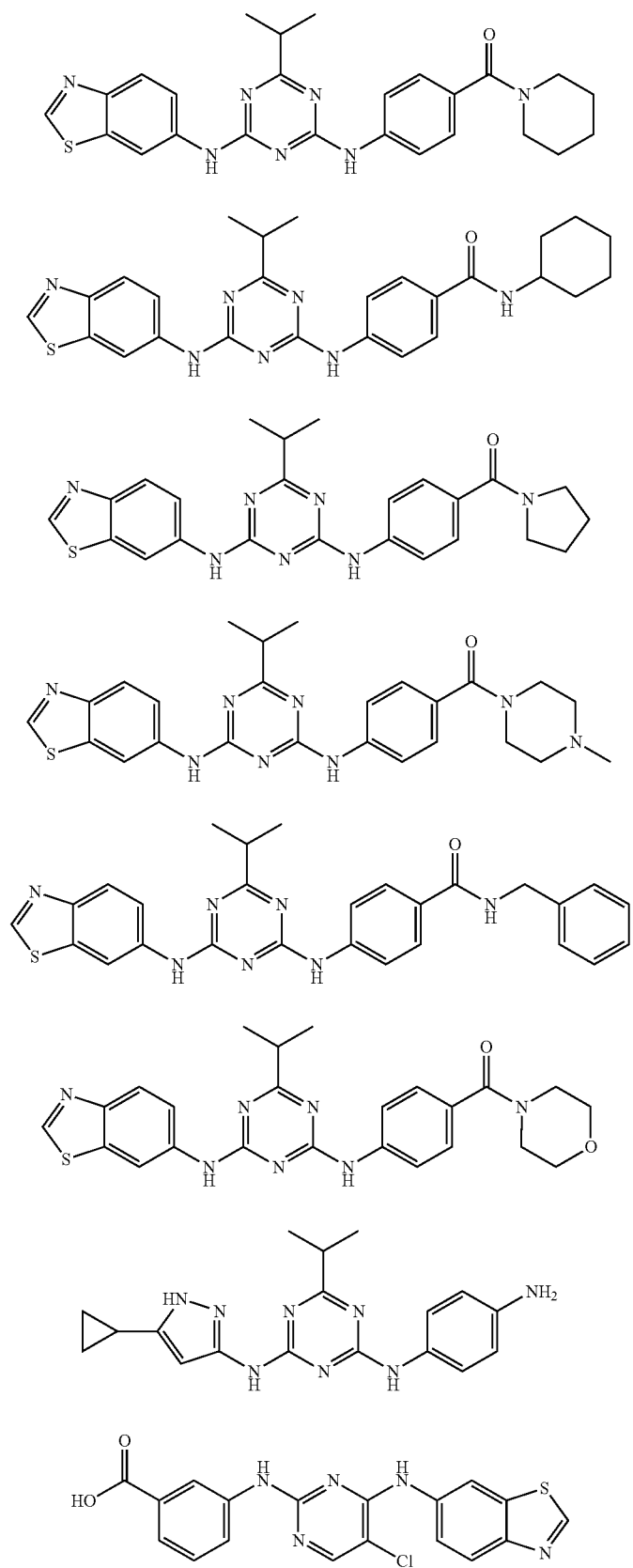

TABLE 1-continued
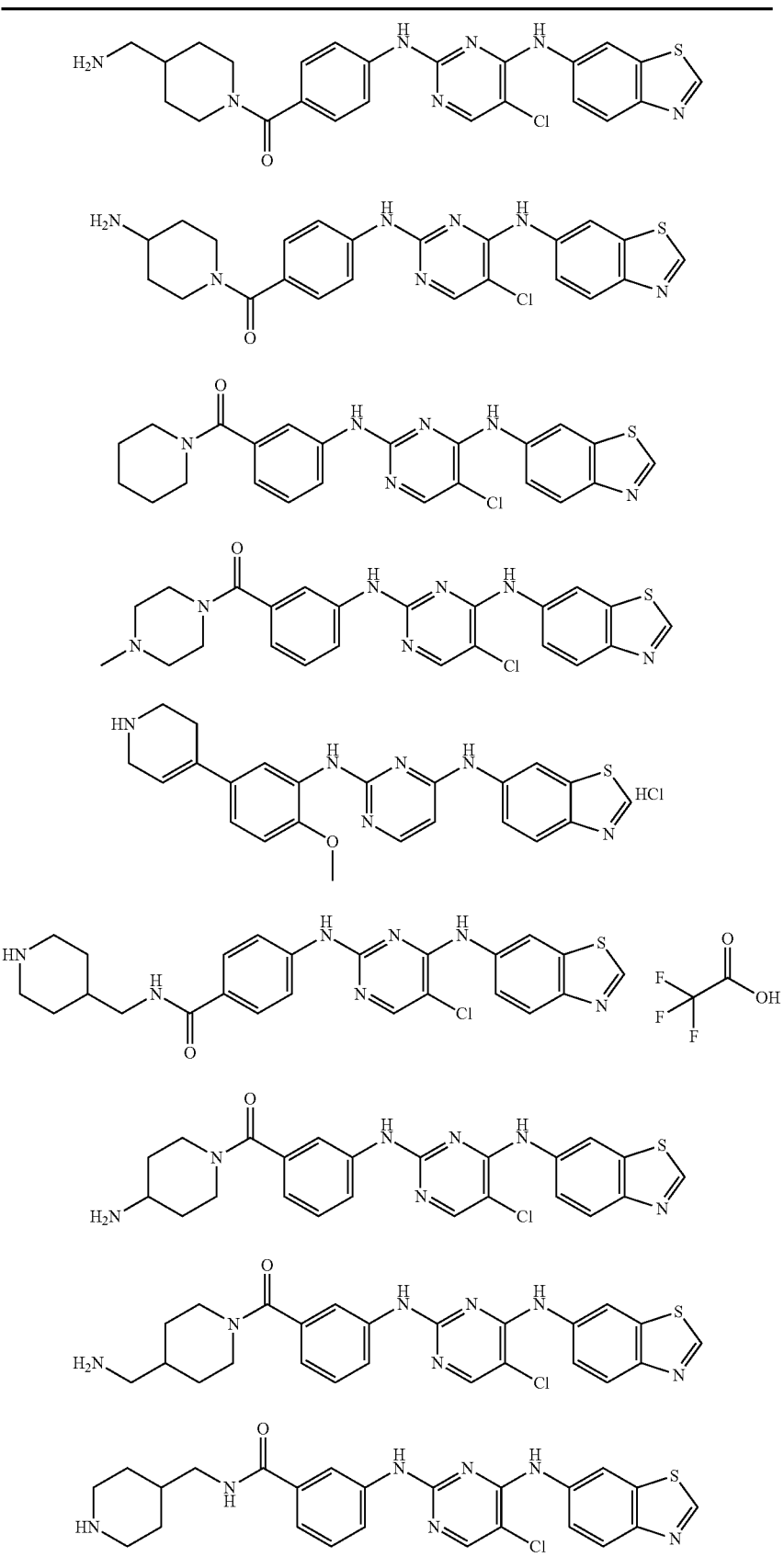

TABLE 1-continued
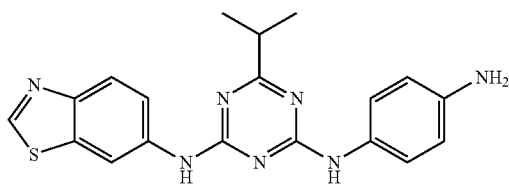 [SMILES: CC(C)c1nc(Nc2ccc(N)cc2)nc(Nc2ccc3ncsc3c2)n1]
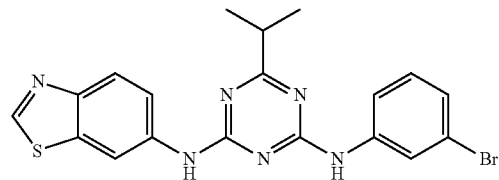
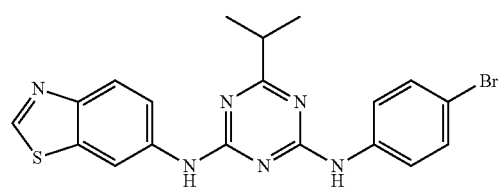 [SMILES: CC(C)c1nc(Nc2ccc(Br)cc2)nc(Nc2ccc3ncsc3c2)n1]
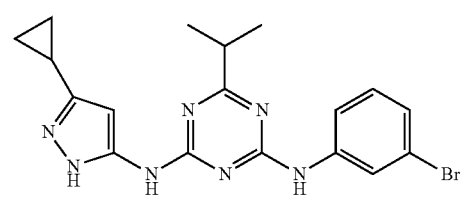 [SMILES: CC(C)c1nc(Nc2cccc(Br)c2)nc(Nc2cc(C3CC3)n[nH]2)n1]
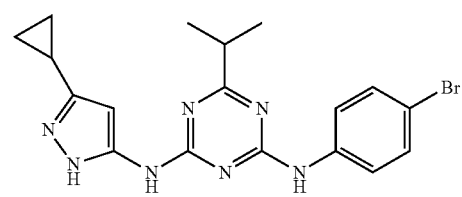 [SMILES: CC(C)c1nc(Nc2ccc(Br)cc2)nc(Nc2cc(C3CC3)n[nH]2)n1]
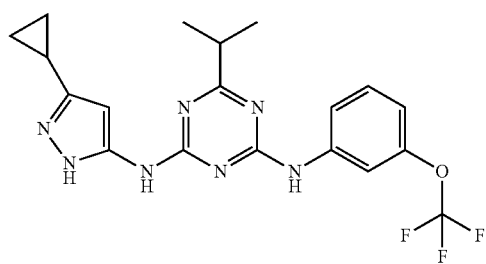 [SMILES: CC(C)c1nc(Nc2cccc(OC(F)(F)F)c2)nc(Nc2cc(C3CC3)n[nH]2)n1]
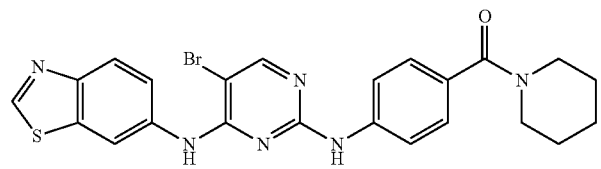 [SMILES: O=C(c1ccc(Nc2ncc(Br)c(Nc3ccc4ncsc4c3)n2)cc1)N1CCCCC1]
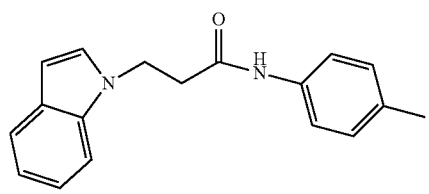 [SMILES: Cc1ccc(NC(=O)CCn2ccc3ccccc32)cc1]

TABLE 1-continued
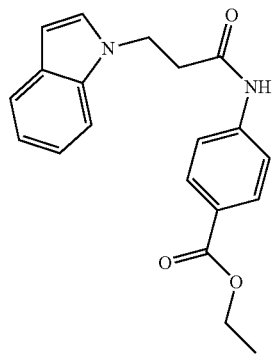 [SMILES: CCOC(=O)c1ccc(NC(=O)CCn2ccc3ccccc32)cc1]
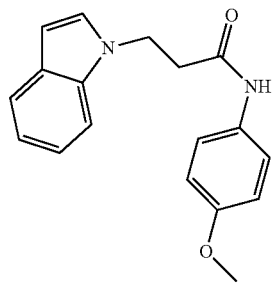 [SMILES: COc1ccc(NC(=O)CCn2ccc3ccccc32)cc1]
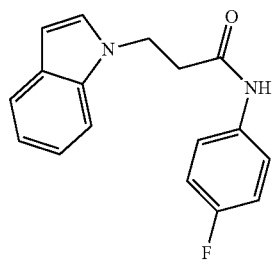 [SMILES: O=C(CCn1ccc2ccccc21)Nc1ccc(F)cc1]
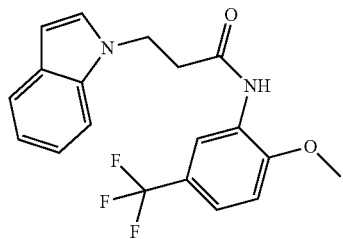 [SMILES: COc1ccc(C(F)(F)F)cc1NC(=O)CCn1ccc2ccccc21]
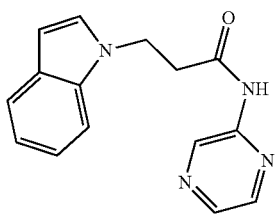 [SMILES: O=C(CCn1ccc2ccccc21)Nc1cnccn1]
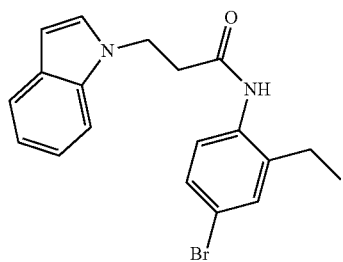 [SMILES: CCc1cc(Br)ccc1NC(=O)CCn1ccc2ccccc21]

TABLE 1-continued
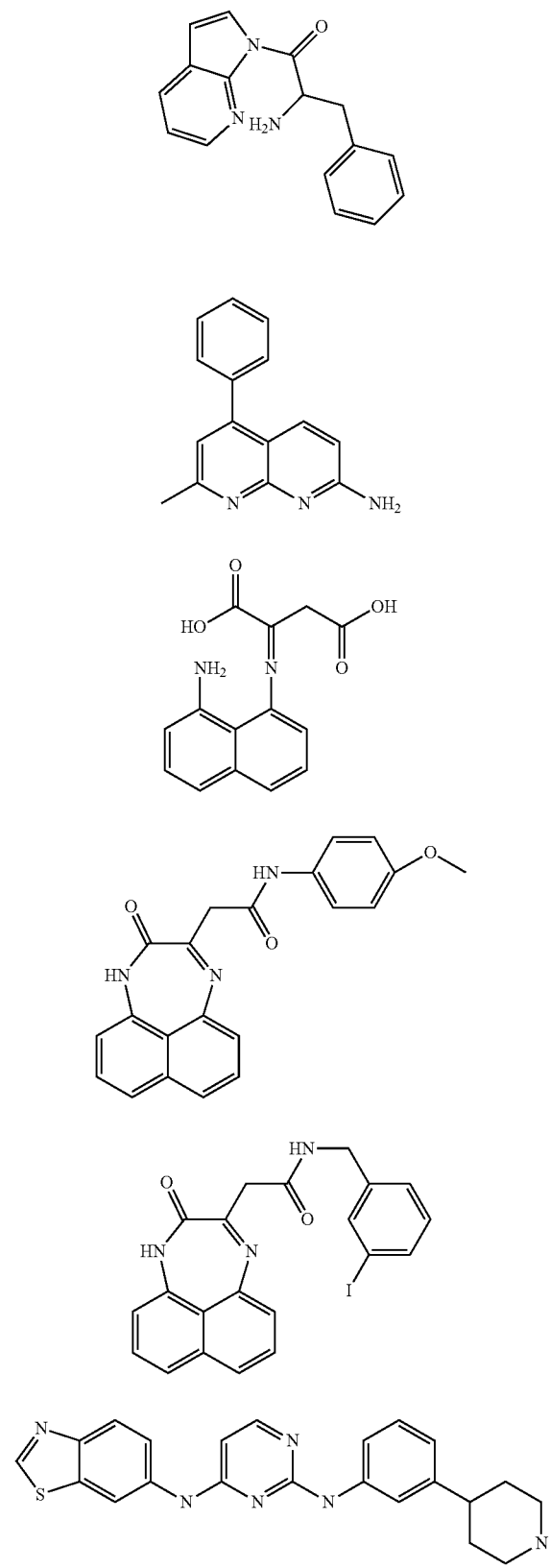

TABLE 1-continued
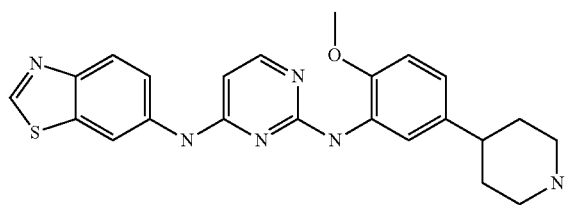 [SMILES: COc1ccc(C2CCNCC2)cc1Nc1nccc(Nc2ccc3ncsc3c2)n1]
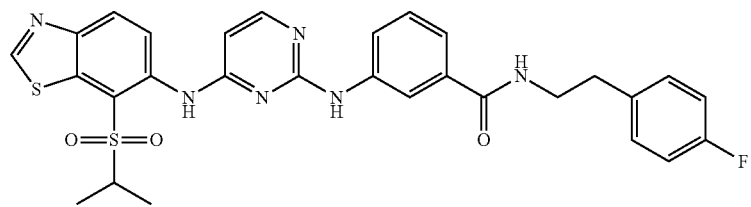 [SMILES: CC(C)S(=O)(=O)c1c(Nc2ccnc(Nc3cccc(C(=O)NCCc4ccc(F)cc4)c3)n2)ccc2ncsc12]
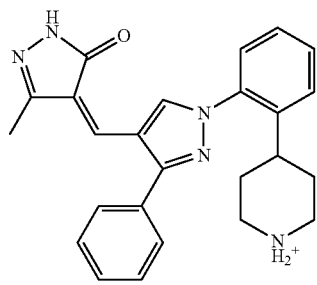 [SMILES: CC1=NNC(=O)/C1=C\c1cn(-c2ccccc2C2CC[NH2+]CC2)nc1-c1ccccc1]
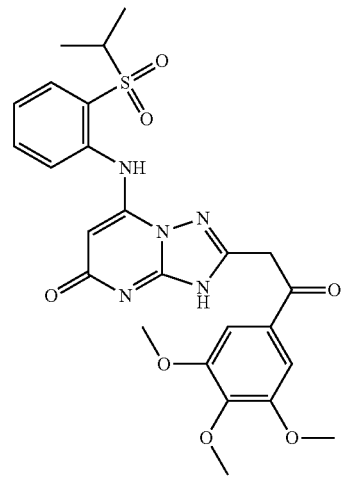 [SMILES: COc1cc(C(=O)Cc2nn3c(Nc4ccccc4S(=O)(=O)C(C)C)cc(=O)nc3[nH]2)cc(OC)c1OC]
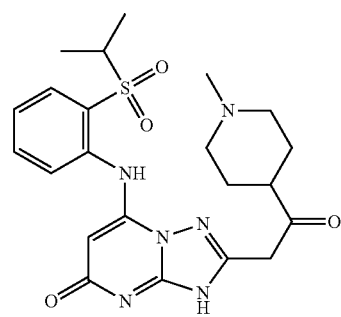 [SMILES: CC(C)S(=O)(=O)c1ccccc1Nc1cc(=O)nc2[nH]c(CC(=O)C3CCN(C)CC3)nn12]

TABLE 1-continued
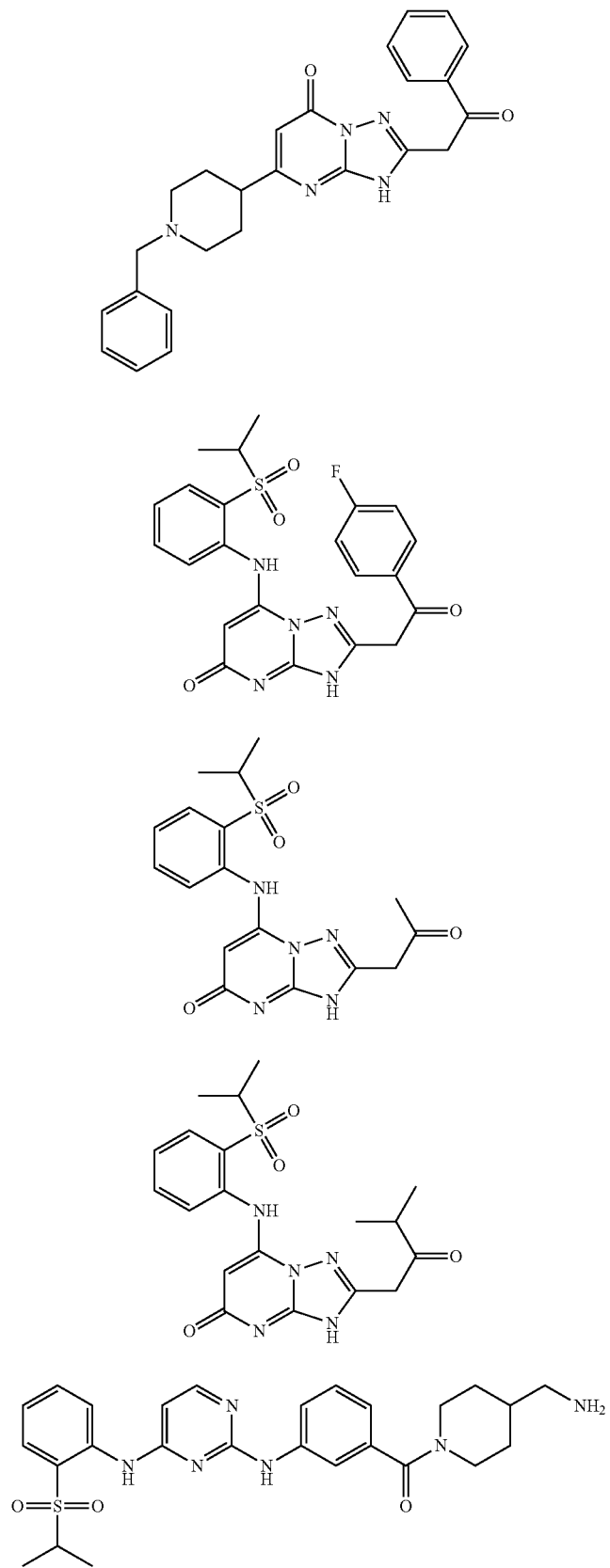

TABLE 1-continued
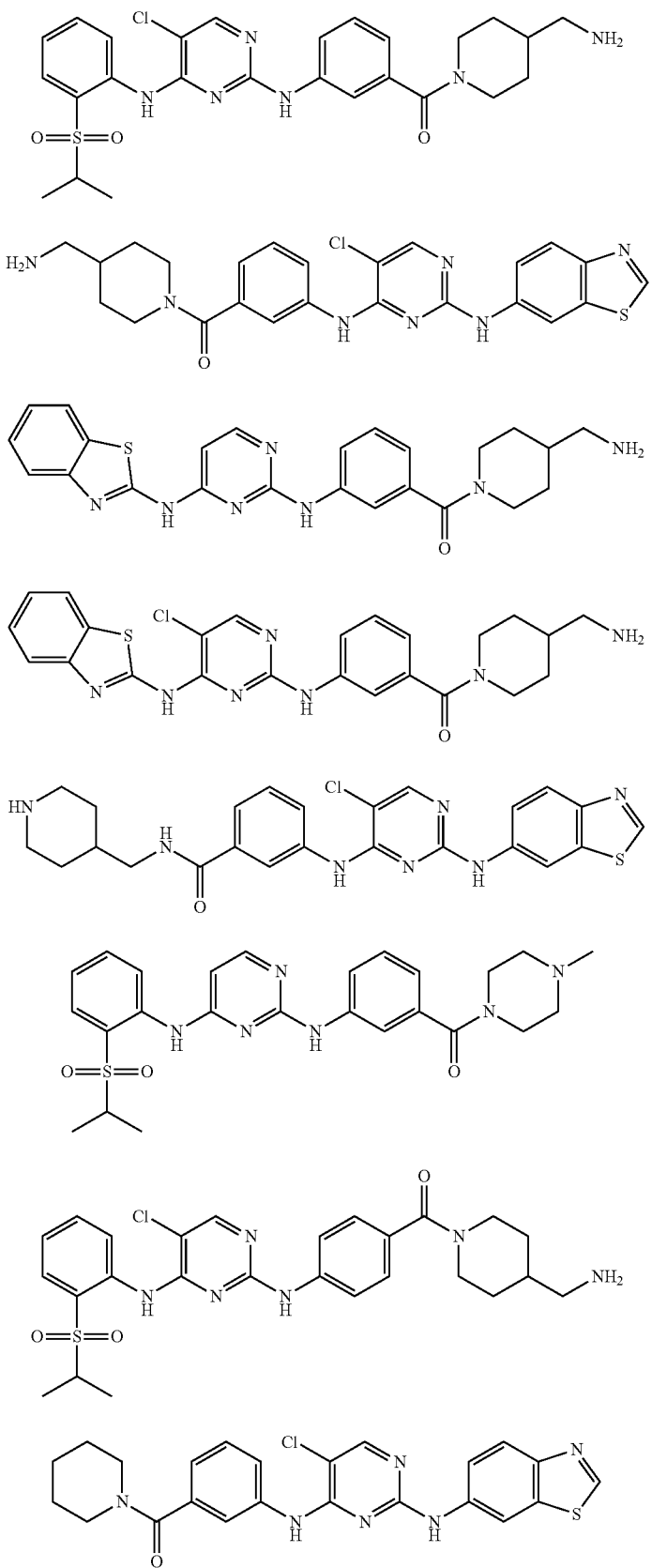

TABLE 1-continued
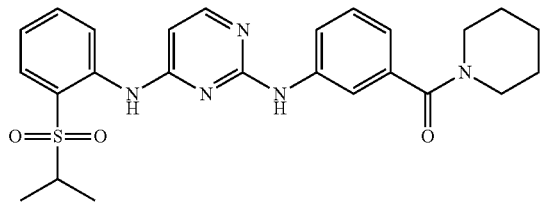 [SMILES: CC(C)S(=O)(=O)c1ccccc1Nc1ccnc(Nc2cccc(C(=O)N3CCCCC3)c2)n1]
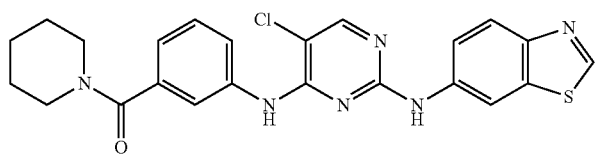 [SMILES: O=C(c1cccc(Nc2nc(Nc3ccc4ncsc4c3)ncc2Cl)c1)N1CCCCC1]
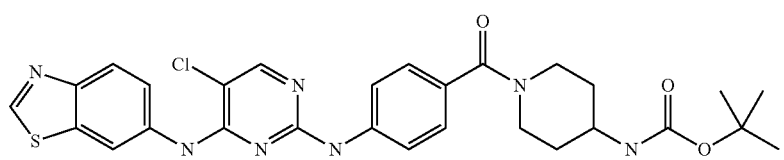 [SMILES: CC(C)(C)OC(=O)NC1CCN(C(=O)c2ccc(Nc3ncc(Cl)c(Nc4ccc5ncsc5c4)n3)cc2)CC1]
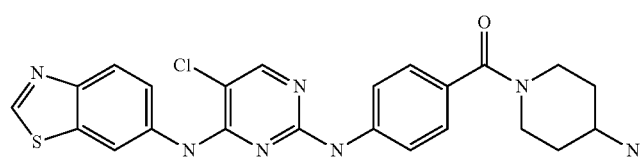 [SMILES: NC1CCN(C(=O)c2ccc(Nc3ncc(Cl)c(Nc4ccc5ncsc5c4)n3)cc2)CC1]
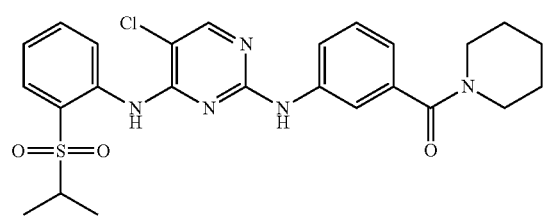 [SMILES: CC(C)S(=O)(=O)c1ccccc1Nc1nc(Nc2cccc(C(=O)N3CCCCC3)c2)ncc1Cl]
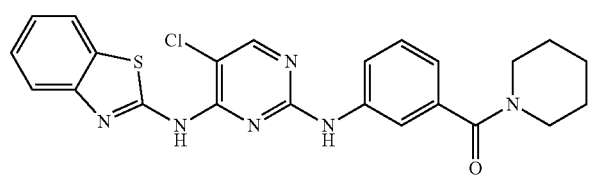 [SMILES: O=C(c1cccc(Nc2ncc(Cl)c(Nc3nc4ccccc4s3)n2)c1)N1CCCCC1]
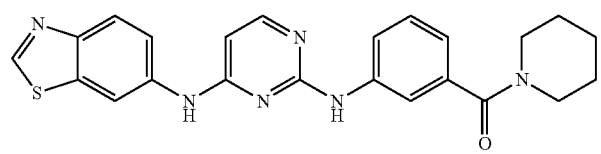 [SMILES: O=C(c1cccc(Nc2nccc(Nc3ccc4ncsc4c3)n2)c1)N1CCCCC1]
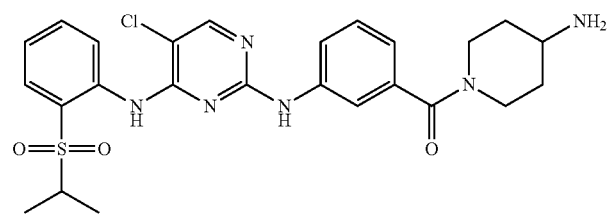 [SMILES: CC(C)S(=O)(=O)c1ccccc1Nc1nc(Nc2cccc(C(=O)N3CCC(N)CC3)c2)ncc1Cl]

TABLE 1-continued
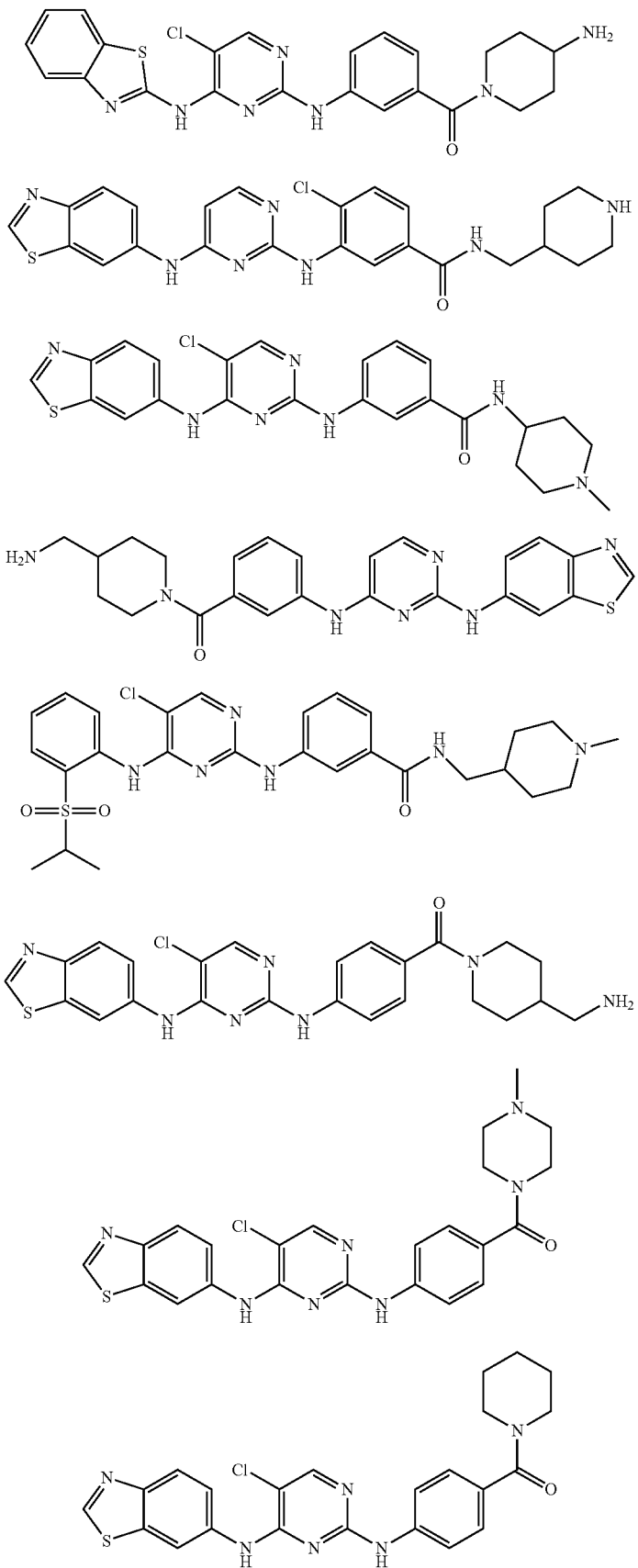

TABLE 1-continued

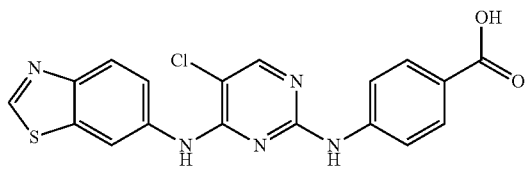 [SMILES: O=C(O)c1ccc(Nc2ncc(Cl)c(Nc3ccc4ncsc4c3)n2)cc1]

EXAMPLES

The following are illustrative, but non-limiting, examples of certain embodiments of the present invention.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis.

Biochemical Inhibition Assay

In Vitro ROS Enzymatic Reaction Assay

The ROS enzymatic reactions were carried out with a high throughput screening platform for phosphor-detection of kinase activity. This platform based on homogeneous time resolved fluorescence (HTRF) technology from Cisbio Bioassays, Inc. (Cisbio). The compounds were added at a concentration of 5 uM or 10 uM to a reaction mix, having the following components: ROS or EGFR enzyme, 0.008 ng/ul; ATP, 10 uM, MgCl$_2$, 10 mM; DTT, 1 mM; 1× Enzymatic buffer I Kinase have HEPES 50 mM, BSA 0.01%, NaN$_3$ 0.02%, Orthovanadate 0.1 mM; Tween 20, 0.01%, and Tyrosine kinase substrate 300 nM. The reaction was allowed to proceed for 30 minutes at room temperature. An equal volume of detection buffer was then added to the reaction mix. The detection buffer contains: HEPES 50 mM, BSA 0.055%, KF 0.4 M, EDTA 10 mM.

HTRF kinase reaction is detected with a biotinylated peptide substrate and a specific anti-phospho peptide antibody that is coupled with Eu$^{3+}$ Cryptate and XL665 conjugated with streptavidin. % Inhibition was determined by comparing the samples having compounds added with samples without ROS or EGFR as 100% inhibition and samples without any compounds added as 0% inhibition. ROS compound IC50 data and EGFR IC50 data were calculated using Prism 4 software with 4 parameters fitting.

Results:

Table 2 here lists the ROS kinase inhibition data for the compounds shown in Table 1, as well as some additional compounds. Shown here are the % Kinase Inhibition data when a compound was added to 10 uM or 5 uM, the 1050 data for ROS kinases inhibition, and the 1050 data for the inhibition of EGFR.

TABLE 2

| Structure | Kinase Inhib. 10 uM (%) | Kinase Inhib. 5 uM (%) | IC50 ROS (uM) | IC50 EGFR (uM) |
|---|---|---|---|---|
| (structure 1) | 20.19 | | | |
| (structure 2) | 41.55 | | | 1.3 |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| 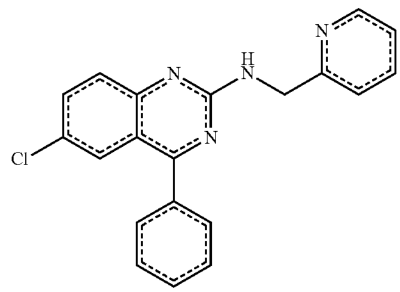 | 25.03 | | | |
| 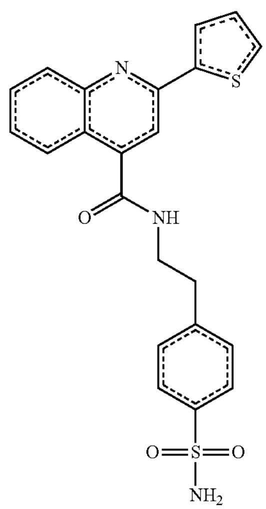 | 21.53 | | | |
| 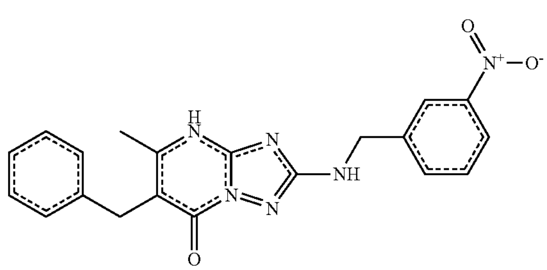 | 23.83 | | | |
| 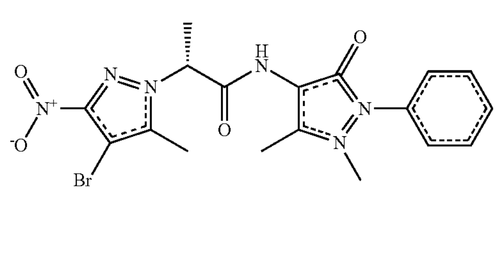 | 34.11 | | >100 | |

TABLE 2-continued
| Structure | Kinase Inhib. 10 uM (%) | Kinase Inhib. 5 uM (%) | IC50 ROS (uM) | IC50 EGFR (uM) |
|---|---|---|---|---|
| 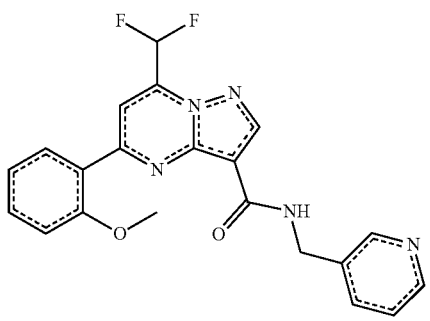 | 35.05 | | 4.0 | |
| 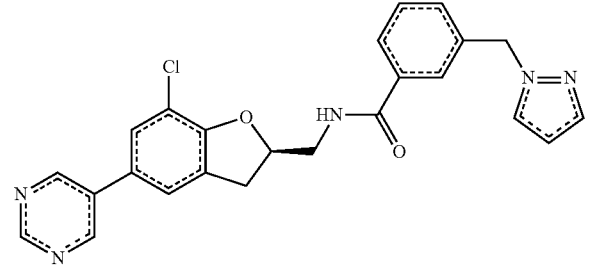 | 30.25 | | >100 | |
| 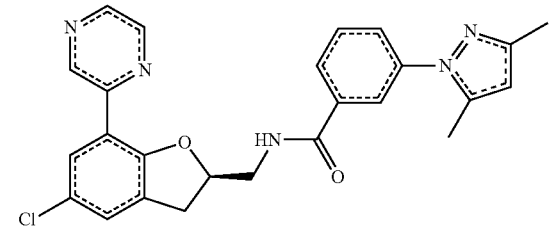 | 29.68 | | >100 | |
| 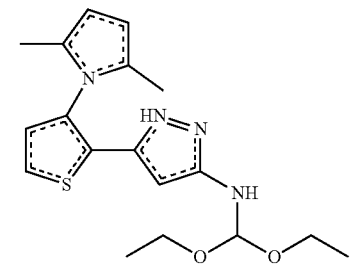 | 27.57 | | | |
| 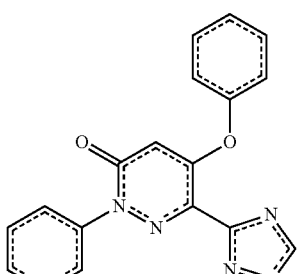 | 20.40 | | | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| *(structure: 3-chlorobenzohydrazide-quinoxaline with benzyl)* | 24.28 | | | |
| *(structure: amino-cyano pyranopyrazole with methoxyphenyl and CF3)* | 61.61 | | 1.7 | |
| *(structure: phenylamino-methylene pyrazolone with phenyl)* | 30.59 | | | |
| *(structure: methoxyphenylamino-methylene pyrazolone with phenyl)* | 34.25 | | | |
| *(structure: tolylamino-methylene pyrazolone with phenyl)* | 43.69 | | | |
| *(structure: tolylamino-pyrimidine-aminobenzoyl-tetrahydropyridine)* | 94.25 | | 0.08 | |

… TABLE 2-continued
| Structure | Kinase Inhib. 10 uM (%) | Kinase Inhib. 5 uM (%) | IC50 ROS (uM) | IC50 EGFR (uM) |
|---|---|---|---|---|
| 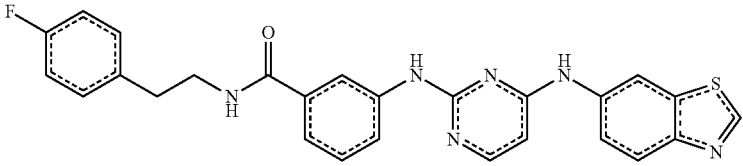 | | 100.68 | 0.13 | |
| 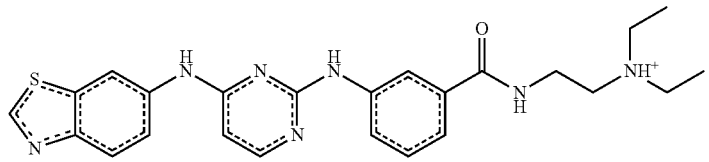 | | 101.61 | | |
| 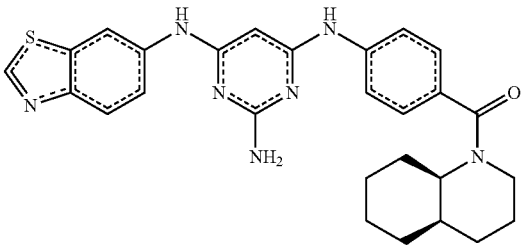 | | 27.92 | | |
| 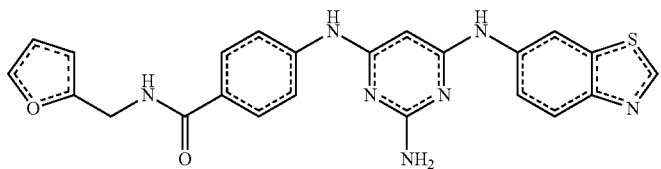 | | 48.97 | 3.81 | |
| 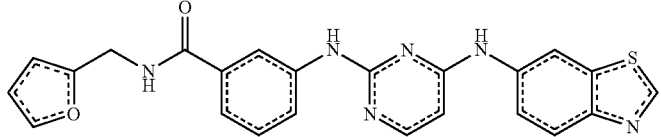 | | 100.94 | 0.16 | |
| 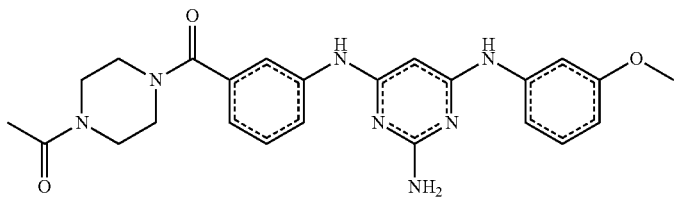 | | 22.31 | | |
| 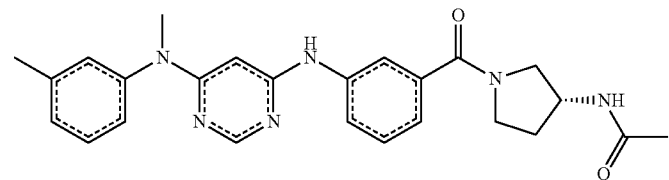 | | 29.64 | | |
| 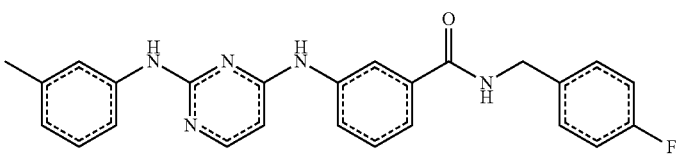 | | 23.73 | | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| | | 101.17 | 0.62 | |
| | | 98.40 | 2.10 | |
| | | 47.31 | | |
| | | 21.21 | | |
| | | 28.49 | | |
| | | 39.47 | 4.1 | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| 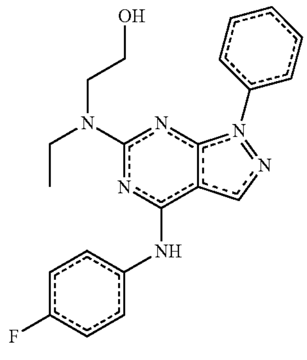 | 38.92 | | 16.85 | |
| | | 41.55 | | |
| 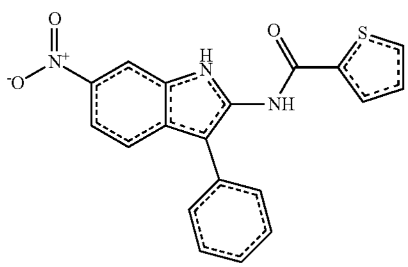 | 23.50 | | | |
| 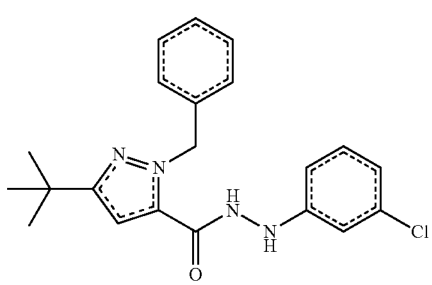 | 27.16 | | | |
| 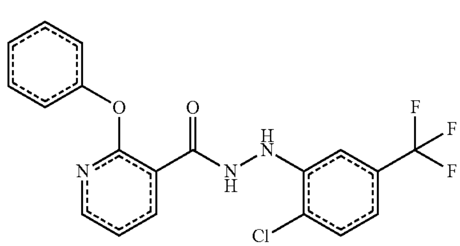 | 31.21 | | >100 | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| 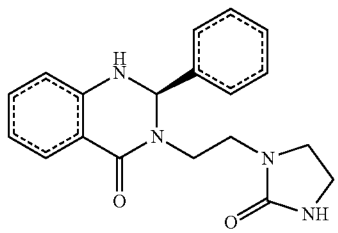 | 20.33 | | | |
| 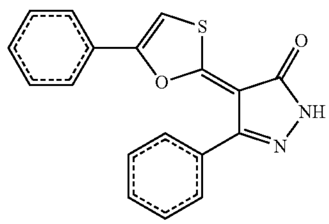 | 77.85 | 69.19 | 0.16 | |
| 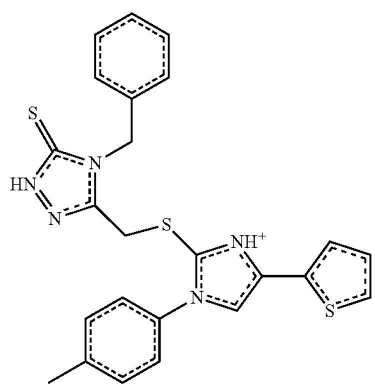 | 28.13 | | | |
| 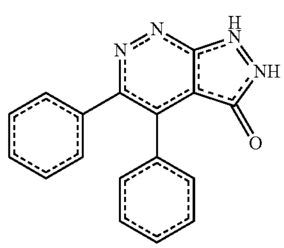 | 35.63 | | 20.35 | |
| 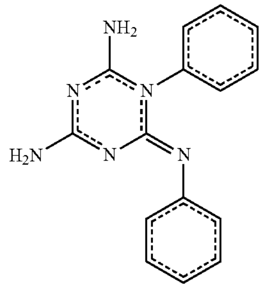 | 34.47 | | >100 | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| 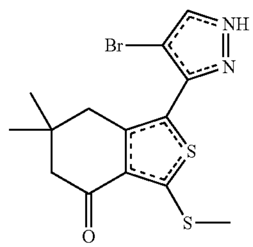 | 34.00 | | 10 | |
| | | 28.49 | | |
| | | 23.62 | | |
| | | 31.08 | | |
| | | 21.55 | | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| | | 37.09 | | |
| | | 26.87 | | |
| | | 62.05 | 1.22 | |
| | | 20.00 | | |
| | | 20.74 | | |
| 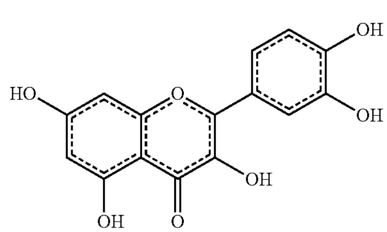 | 98.18 | 99.62 | 0.05 | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| [structure] | | 32.58 | | |
| [structure] | | 96.28 | 0.361 | |
| [structure] | | 22.67 | | |
| [structure] | | 100.78 | 0.435 | |
| [structure] | | 100.91 | | |
| [structure] | | 33.27 | | |
| [structure] | | 100.72 | 0.271 | |
| [structure] | | 101.04 | | |
| [structure] | | 99.38 | 0.140 | |

TABLE 2-continued
| Structure | Kinase Inhib. 10 uM (%) | Kinase Inhib. 5 uM (%) | IC50 ROS (uM) | IC50 EGFR (uM) |
|---|---|---|---|---|
| 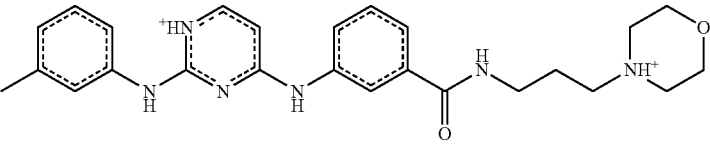 | | 92.94 | | |
| 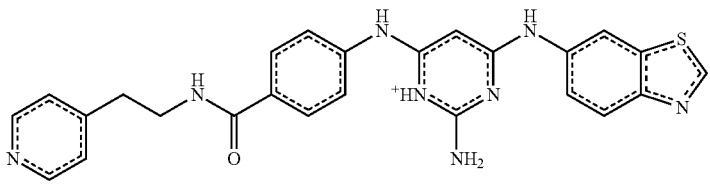 | | 61.14 | | |
| 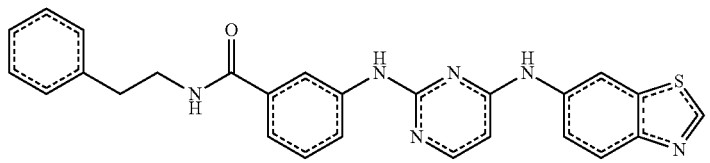 | | 94.23 | | |
| 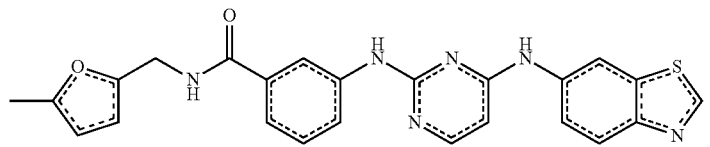 | | 99.06 | 0.196 | |
| 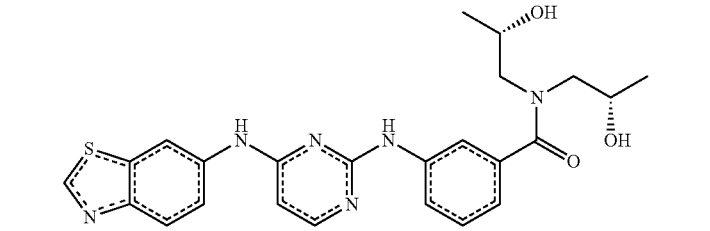 | | 100.81 | | |
| 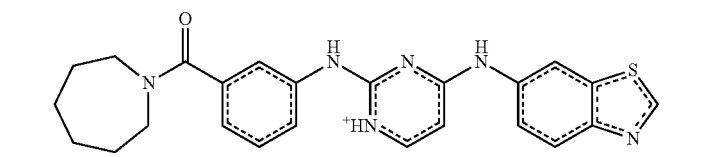 | | 100.38 | 0.450 | |
| 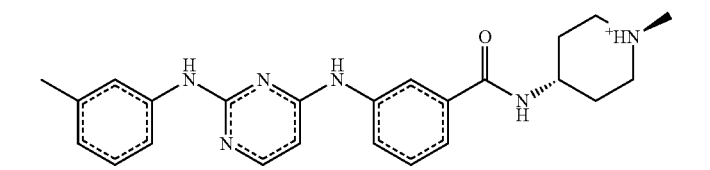 | | 98.59 | 1.42 | |
| 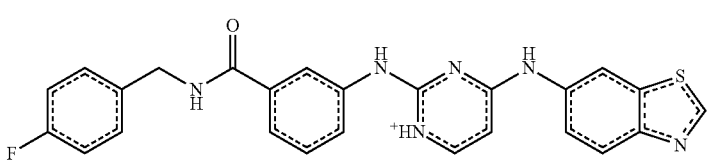 | | 100.82 | 0.582 | |

TABLE 2-continued
| Structure | Kinase Inhib. 10 uM (%) | Kinase Inhib. 5 uM (%) | IC50 ROS (uM) | IC50 EGFR (uM) |
|---|---|---|---|---|
| 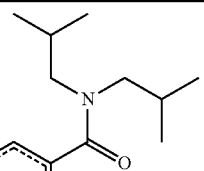 | | 99.62 | 1.296 | |
| 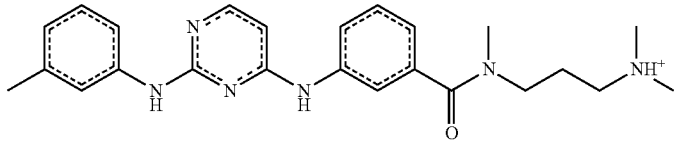 | | 98.57 | | |
| 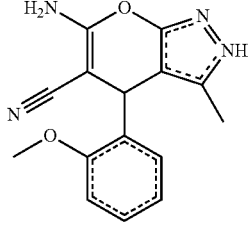 | | 27.58 | | |
| 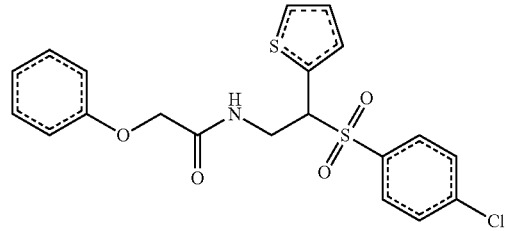 | 101.51 | 83.80 | 1.78 | |
| 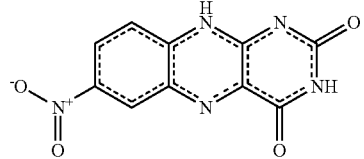 | | 26.23 | | |
| 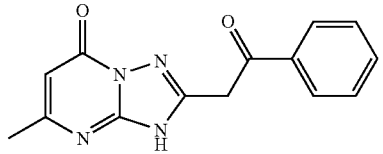 [SMILES: Cc1cc(=O)n2nc(CC(=O)c3ccccc3)[nH]c2n1] | | 33.25 | | |
| 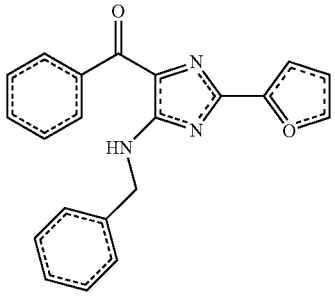 | | 25.92 | | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| | | 25.09 | | |
| | | 26.59 | | |
| | | 40.40 | | |
| | | 85.11 | 0.48 | |
| | | 38.40 | 2.1 | >50 |
| | | 100 | 0.045 | 18.88 |

TABLE 2-continued
| Structure | Kinase Inhib. 10 uM (%) | Kinase Inhib. 5 uM (%) | IC50 ROS (uM) | IC50 EGFR (uM) |
|---|---|---|---|---|
| 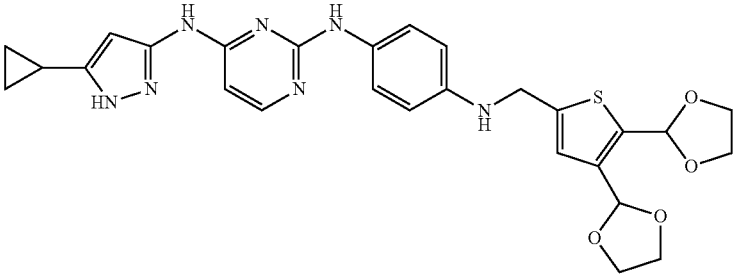 [SMILES: c1cc(Nc2cc(C3CC3)[nH]n2)nc(Nc2ccc(NCc3cc(C4OCCO4)c(C4OCCO4)s3)cc2)n1] | | 79.27 | 1.14 | >50 |
| 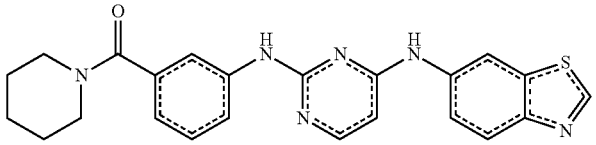 | | 100.04 | 0.392 | |
| 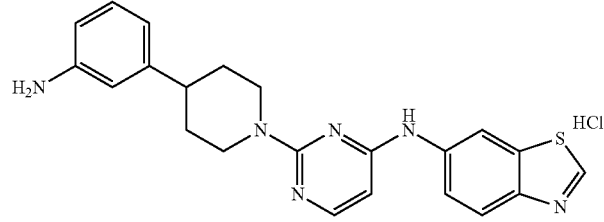 [SMILES: Nc1cccc(C2CCN(c3nccc(Nc4ccc5ncsc5c4)n3)CC2)c1 ; Cl] | | 100.78 | 0.048 | 4.7 |
| 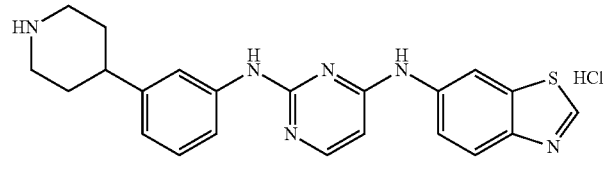 [SMILES: c1cc(Nc2nccc(Nc3ccc4ncsc4c3)n2)cc(C2CCNCC2)c1 ; Cl] | | 100.46 | 0.042 | 4.6 |
| 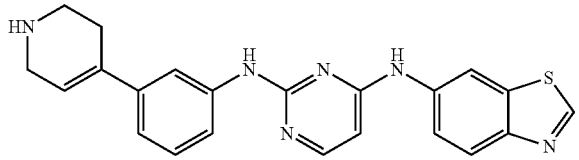 [SMILES: C1=C(c2cccc(Nc3nccc(Nc4ccc5ncsc5c4)n3)c2)CCNC1] | | 100.73 | 0.041 | >5.0 |
| 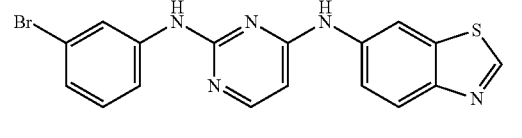 [SMILES: Brc1cccc(Nc2nccc(Nc3ccc4ncsc4c3)n2)c1] | | 89.99 | 0.017 | >5.0 |
| 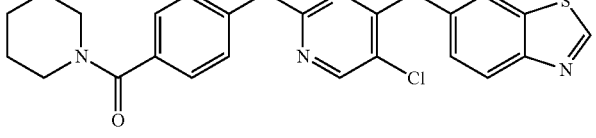 | | 87.91 | 0.070 | >5.0 |
| 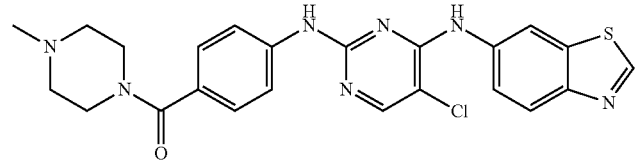 [SMILES: CN1CCN(C(=O)c2ccc(Nc3ncc(Cl)c(Nc4ccc5ncsc5c4)n3)cc2)CC1] | | 92.22 | 0.405 | >5.0 |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| (4-carboxyphenyl)-(5-chloro-pyrimidin-2-yl)-(benzothiazol-6-yl)-diamine | | 100.60 | 0.037 | 2.4 |
| Boc-piperidinyl-benzoyl-phenyl-(5-chloro-pyrimidin-2-yl)-(benzothiazol-6-yl)-diamine | | 29.35 | >5.0 | >5.0 |
| (benzothiazol-6-yl)-(isopropyl-triazinyl)-cyclohexyl-diamine | | | 1.50 | |
| (benzothiazol-6-yl)-(isopropyl-triazinyl)-benzyl-diamine | | | 0.358 | |
| (benzothiazol-6-yl)-(isopropyl-triazinyl)-cyclohexylmethyl-diamine | | | 0.528 | |
| (benzothiazol-2-ylmethyl-phenyl)-(ethoxy-isopropyl-triazinyl)-amine | | | 9.26 | |
| (benzothiazol-6-yl)-(isopropyl-pyrrolidinyl-triazinyl)-amine | | 20.87 | >5.0 | n/a |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| | | 23.51 | >5.0 | n/a |
| | | 45.15 | >5.0 | n/a |
| | | 25.30 | >5.0 | n/a |
| | | 58.64 | >5.0 | n/a |
| | | 98.76 | 0.76 | n/a |
| | | 92.55 | 1.878 | n/a |
| | | 90.72 | 3.891 | n/a |

TABLE 2-continued

| Structure | Kinase Inhib. 10 uM (%) | Kinase Inhib. 5 uM (%) | IC50 ROS (uM) | IC50 EGFR (uM) |
| --- | --- | --- | --- | --- |
| (benzothiazole-NH-triazine(iPr)-NH-phenyl-C(O)NH-CH2-phenyl) | | 97.36 | 3.694 | n/a |
| (benzothiazole-NH-triazine(iPr)-NH-phenyl-C(O)-morpholine) | | 65.72 | 0.333 | n/a |
| (cyclopropyl-pyrazole-NH-triazine(iPr)-NH-phenyl-NH2) | | 20.45 | >5.0 | n/a |
| (HOOC-phenyl-NH-pyrimidine(Cl)-NH-benzothiazole) | | 100 | 0.189 | >5.0 |
| (H2N-CH2-piperidine-C(O)-phenyl-NH-pyrimidine(Cl)-NH-benzothiazole) | | 100 | 0.368 | >5.0 |
| (H2N-piperidine-C(O)-phenyl-NH-pyrimidine(Cl)-NH-benzothiazole) | | 100 | 0.444 | >5.0 |
| (piperidine-C(O)-phenyl-NH-pyrimidine(Cl)-NH-benzothiazole) | | 100 | 0.24 | >5.0 |
| (N-methylpiperazine-C(O)-phenyl-NH-pyrimidine(Cl)-NH-benzothiazole) | | 100 | 0.33 | >5.0 |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| [structure] | | 100 | 0.003 | 0.802 |
| [structure] | | 100 | 1.009 | >5.0 |
| [structure] | | 100 | 0.165 | >5.0 |
| [structure] | | 100 | 0.11 | >5.0 |
| [structure] | | 100 | 0.38 | >5.0 |
| [structure] | 27.50 | | | |
| [structure] | 24.51 | | | |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| *indole-CH2CH2-C(O)NH-(4-methoxyphenyl)* | | 29.54 | | |
| *indole-CH2CH2-C(O)NH-(4-fluorophenyl)* | | 23.17 | | |
| *indole-CH2CH2-C(O)NH-(2-methoxy-5-trifluoromethylphenyl)* | | 26.45 | | |
| *indole-CH2CH2-C(O)NH-(pyrazin-2-yl)* | | 14.35 | | |
| *indole-CH2CH2-C(O)NH-(4-bromo-2-ethylphenyl)* | | 20.82 | | |
| *7-azaindole-C(O)-CH(NH2)-CH2-phenyl* | | 26.91 | | |

TABLE 2-continued
| Structure | Kinase Inhib. 10 uM (%) | Kinase Inhib. 5 uM (%) | IC50 ROS (uM) | IC50 EGFR (uM) |
|---|---|---|---|---|
| 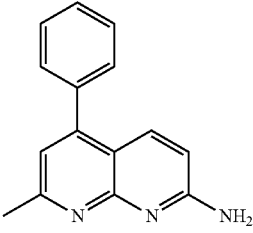 [SMILES: Cc1cc(-c2ccccc2)c2ccc(N)nc2n1] | 28.86 | | | |
| 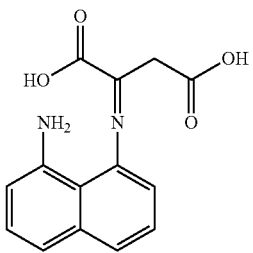 [SMILES: Nc1cccc2cccc(N=C(CC(=O)O)C(=O)O)c12] | 24.61 | | | |
| 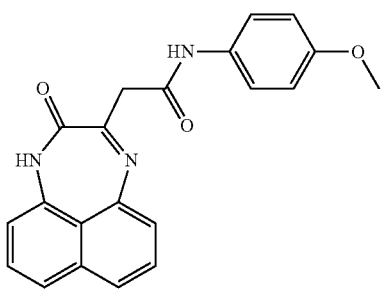 [SMILES: COc1ccc(NC(=O)CC2=Nc3cccc4cccc(c34)NC2=O)cc1] | 26.47 | | | |
| 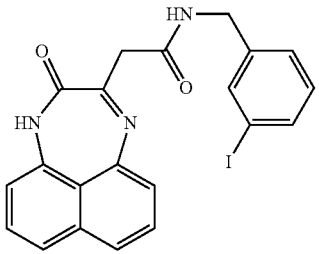 [SMILES: O=C(CC1=Nc2cccc3cccc(c23)NC1=O)NCc1cccc(I)c1] | 22.50 | | | |
| 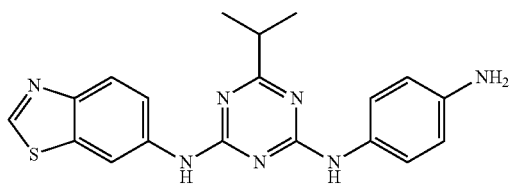 [SMILES: CC(C)c1nc(Nc2ccc(N)cc2)nc(Nc2ccc3ncsc3c2)n1] | | | | 0.746 |
| 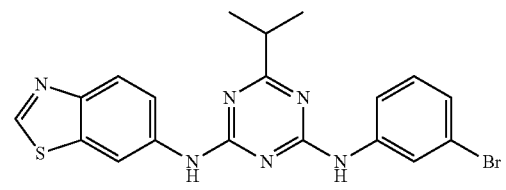 [SMILES: CC(C)c1nc(Nc2cccc(Br)c2)nc(Nc2ccc3ncsc3c2)n1] | | | | 0.086 |

TABLE 2-continued

| Structure | Kinase Inhib. 10 uM (%) | Kinase Inhib. 5 uM (%) | IC50 ROS (uM) | IC50 EGFR (uM) |
|---|---|---|---|---|
| 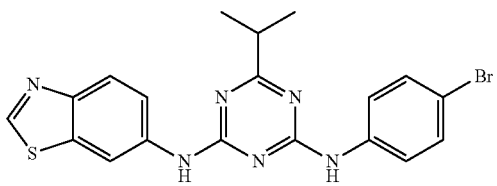 [SMILES: CC(C)c1nc(Nc2ccc(Br)cc2)nc(Nc2ccc3ncsc3c2)n1] | | | 0.84 | |
| 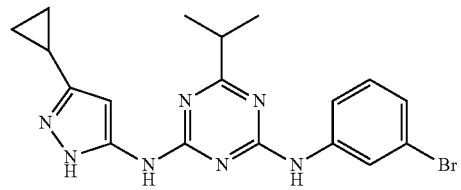 [SMILES: CC(C)c1nc(Nc2cccc(Br)c2)nc(Nc2cc(C3CC3)n[nH]2)n1] | | | 0.038 | |
| 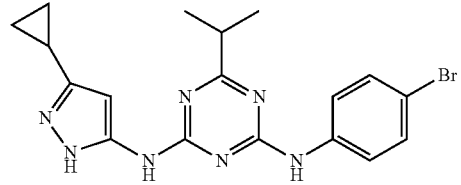 [SMILES: CC(C)c1nc(Nc2ccc(Br)cc2)nc(Nc2cc(C3CC3)n[nH]2)n1] | | | 0.067 | |
| 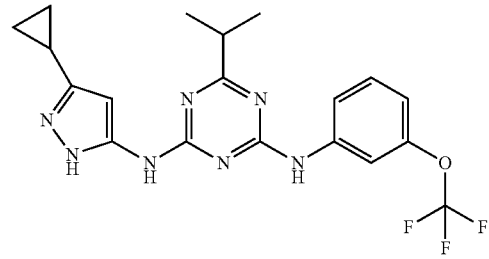 [SMILES: CC(C)c1nc(Nc2cccc(OC(F)(F)F)c2)nc(Nc2cc(C3CC3)n[nH]2)n1] | | | 0.040 | |
| 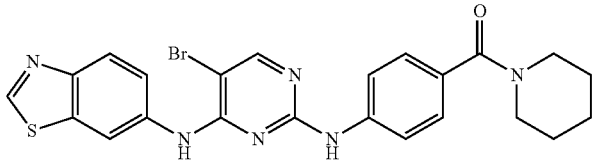 [SMILES: O=C(c1ccc(Nc2ncc(Br)c(Nc3ccc4ncsc4c3)n2)cc1)N1CCCCC1] | | | 0.62 | |
| 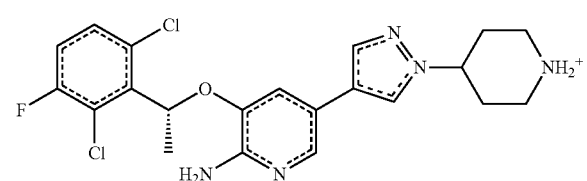 | 100 | | 0.0015 | >5 uM |

In-Vitro Cell Survival Assay

Five tumor-derived cell lines were treated with the ROS inhibitor compounds and cell survival was monitored to determine the cancer prohibition effects of the compounds. The cell lines included HeLa, a cervical cancer cell line, and four glioblastoma cell lines U138, U87, LN18, and U118. The basic protocol for the in-vitro cell survival assay is the same for all five cell lines. In particular, the cells were seeded in 96-well plates at 2-5×10³ cells/well (cell line dependent) in culture medium. The cells were grown for 2 days before the compounds were dissolved in DMSO and added to final concentrations of 100 uM, 10 uM, or 1 uM (DMSO final concentration 0.5%). The cell culture was then assayed one day after the addition of the compounds. The assay used Alamar blue as a redox-sensitive dye that interrogates mitochondrial fitness of cells, and these assays provided a readout for cell proliferation and viability. The raw values were normalized to an average of several vehicle control wells and are presented as percent decrease in proliferation/viability, which is converted to half maximal effective concentration (EC50) values.

Results:

TABLE 3

| Structure | EC50 U138 (uM) | EC50 HeLa (uM) | EC50 U87 (uM) | EC50 LN18 (uM) | EC50 U118 (uM) |
| --- | --- | --- | --- | --- | --- |
| | >100 | >100 | >100 | >100 | >100 |
| | >100 | >100 | >100 | >100 | >100 |
| | >100 | >100 | 71 | 16 | >100 |
| | >100 | >100 | >100 | 25 | 29 |
| | >100 | >100 | 45 | >100 | >100 |

TABLE 3-continued
| Structure | EC50 U138 (uM) | EC50 HeLa (uM) | EC50 U87 (uM) | EC50 LN18 (uM) | EC50 U118 (uM) |
|---|---|---|---|---|---|
| 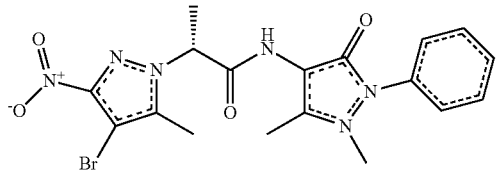 | >100 | >100 | >100 | >100 | >100 |
| 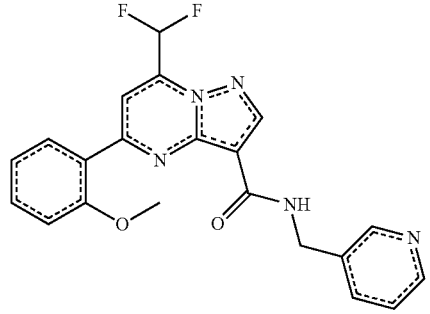 | >100 | >100 | 22 | 16 | >100 |
| 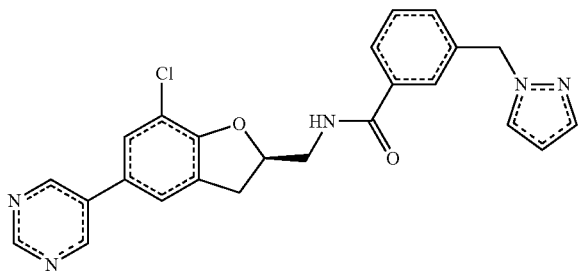 | >100 | >100 | >100 | >100 | >100 |
| 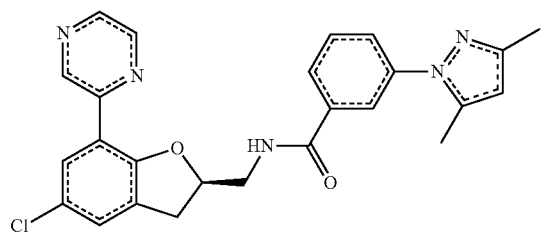 | >100 | 70 | 94 | 64 | 96 |
| 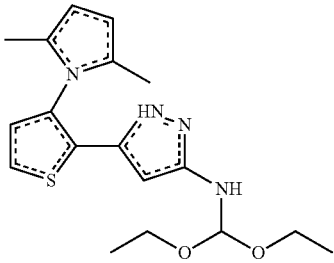 | >100 | >100 | 26 | >100 | >100 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
|  | >100 | >100 | 26 | >100 | >100 |
|  | >100 | >100 | 25 | 22 | >100 |
| 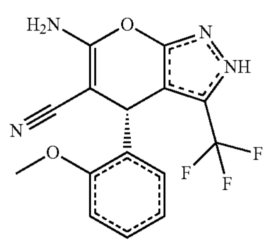 | 84 | 90 | 80 | 62 | >100 |
|  |  | >100 |  | >100 |  |
|  |  | 100 |  | 78 |  |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| (pyrazolone with phenyl and p-tolylaminomethylene) | | >100 | | 52 | |
| (m-tolyl-NH-pyrimidine-NH-phenyl-C(O)-tetrahydropyridine) | >100 | 25 | 17 | 13 | 28 |
| (4-fluorophenethyl-NH-C(O)-phenyl-NH-pyrimidine-NH-benzothiazole) | 8 | 5 | 10 | 6 | 9 |
| (benzothiazole-NH-pyrimidine-NH-phenyl-C(O)-NH-ethyl-NHEt2+) | 45 | 15 | 37 | 15 | 35 |
| (benzothiazole-NH-(2-amino)pyrimidine-NH-phenyl-C(O)-decahydroquinoline) | >100 | 58 | 30 | 14 | >100 |
| (furfuryl-NH-C(O)-phenyl-NH-(2-amino)pyrimidine-NH-benzothiazole) | >100 | 44 | 32 | 18 | 27 |
| (furfuryl-NH-C(O)-phenyl-NH-pyrimidine-NH-benzothiazole) | 35 | 10 | 21 | 10 | 18 |
| (acetylpiperazine-C(O)-phenyl-NH-(2-amino)pyrimidine-NH-methoxyphenyl) | >100 | >100 | >100 | 64 | 91 |

TABLE 3-continued
| Structure | EC50 U138 (uM) | EC50 HeLa (uM) | EC50 U87 (uM) | EC50 LN18 (uM) | EC50 U118 (uM) |
|---|---|---|---|---|---|
| 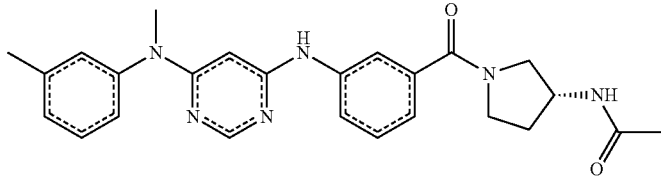 | >100 | >100 | >100 | >100 | >100 |
| 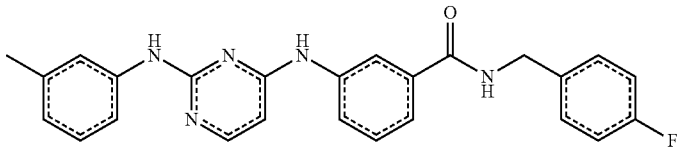 | 19 | 13 | 13 | 7 | 28 |
| 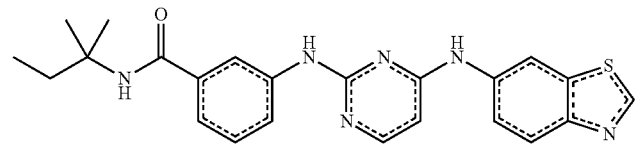 | 46 | 8 | 22 | 15 | 15 |
| 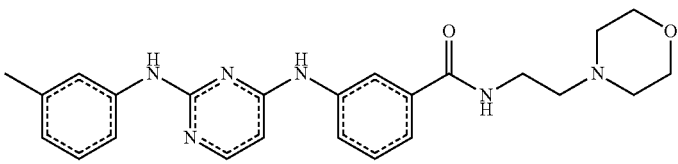 | 54 | 43 | 36 | 11 | 17 |
| 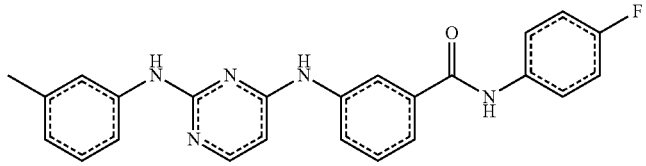 | 75 | 14 | 27 | 6 | 30 |
| 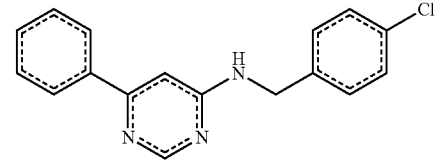 | 62 | >100 | 38 | 62 | 33 |
| 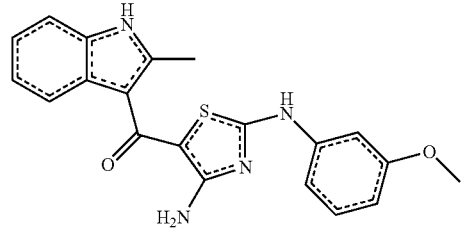 | 19 | 72 | 15 | 10 | 16 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| 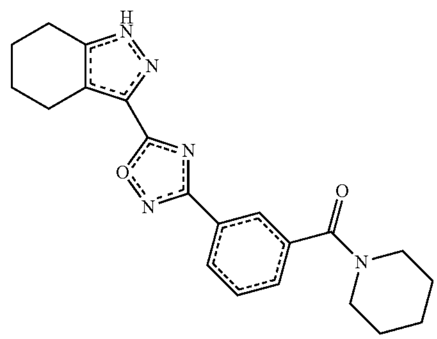 | 83 | >100 | 14 | 62 | 83 |
| 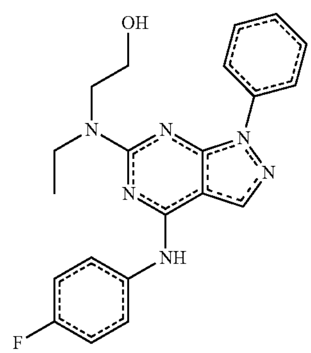 | 57 | 54 | 10 | 7 | 58 |
| 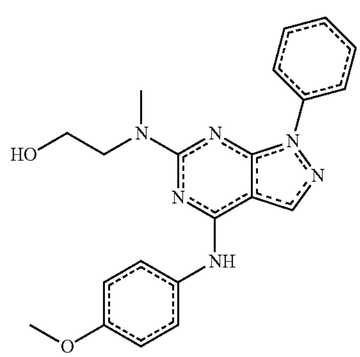 | 9 | 7 | 11 | 6 | 8 |
| 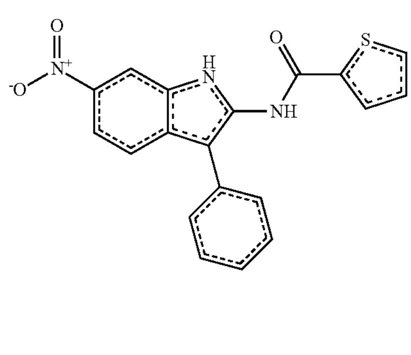 | >100 | 9 | 29 | 62 | 83 |

TABLE 3-continued
| Structure | EC50 U138 (uM) | EC50 HeLa (uM) | EC50 U87 (uM) | EC50 LN18 (uM) | EC50 U118 (uM) |
|---|---|---|---|---|---|
| 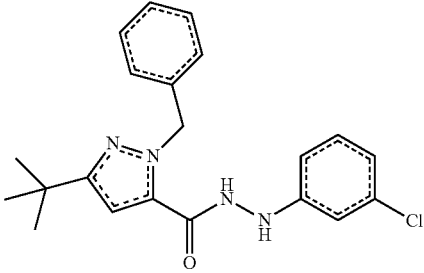 | >100 | >100 | 50 | >100 | >100 |
| 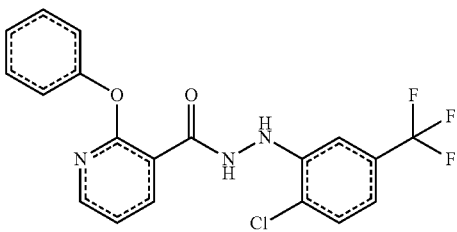 | >100 | 59 | 96 | 58 | >100 |
| 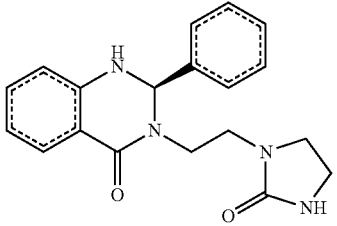 | >100 | >100 | >100 | 36 | 38 |
| 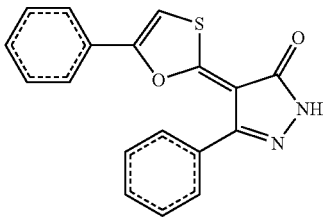 | >100 | 23 | 37 | 17 | 27 |
| 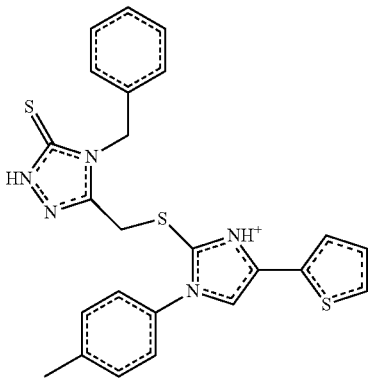 | >100 | >100 | 24 | >100 | >100 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| | >100 | >100 | 28 | >100 | >100 |
| | >100 | >100 | 33 | >100 | >100 |
| | >100 | >100 | 18 | 94 | >100 |
| | >100 | 62 | 20 | >100 | >100 |
| | >100 | >100 | >100 | >100 | >100 |

TABLE 3-continued
| Structure | EC50 U138 (uM) | EC50 HeLa (uM) | EC50 U87 (uM) | EC50 LN18 (uM) | EC50 U118 (uM) |
|---|---|---|---|---|---|
| 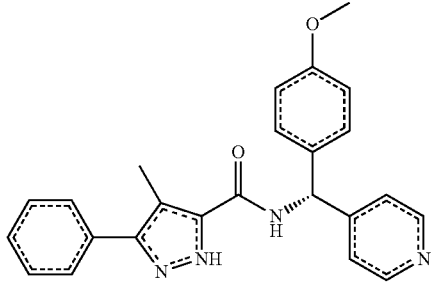 | >100 | >100 | >100 | 59 | >100 |
| 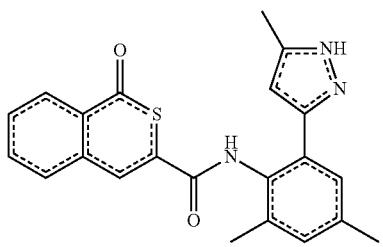 | >100 | >100 | >100 | >100 | >100 |
| 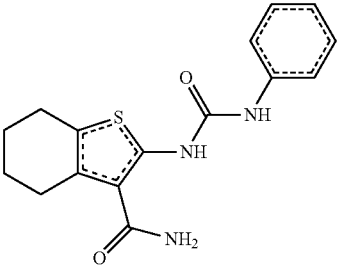 | 27 | 16 | 80 | 38 | 34 |
| 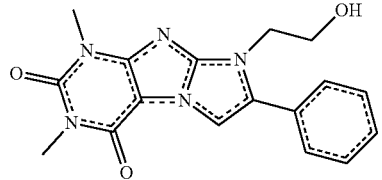 | >100 | >100 | >100 | >100 | >100 |
| 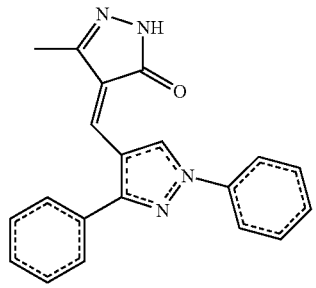 | 8 | 20 | 8 | 12 | 7 |
| 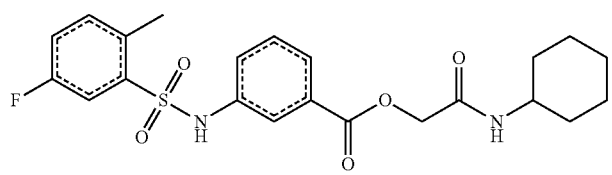 | >100 | >100 | 33 | >100 | >100 |

TABLE 3-continued

| Structure | EC50 U138 (uM) | EC50 HeLa (uM) | EC50 U87 (uM) | EC50 LN18 (uM) | EC50 U118 (uM) |
| --- | --- | --- | --- | --- | --- |
| | >100 | >100 | >100 | >100 | >100 |
| | >100 | 21 | 36 | 24 | 33 |
| | >100 | >100 | 33 | 87 | >100 |
| 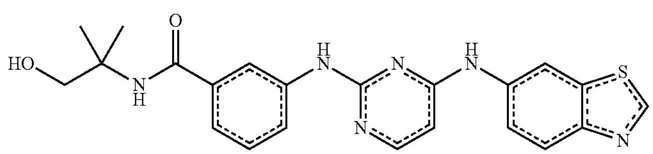 | 16 | 12 | 17 | 10 | 18 |
| | >100 | 50 | 25 | 14 | >100 |
| 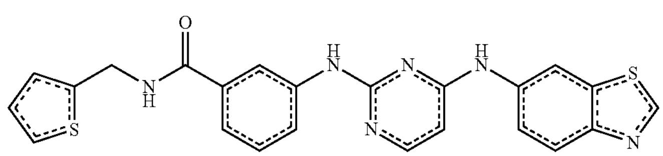 | 26 | 9 | 25 | 11 | 23 |
| | >100 | 19 | 18 | >100 | >100 |
| 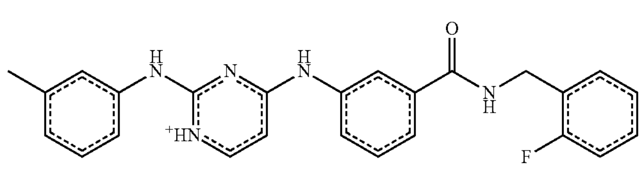 | 34 | 9 | 11 | 6 | 16 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| 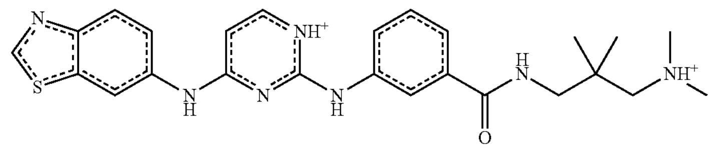 | 73 | 24 | 32 | 9 | 76 |
| | >100 | 11 | 16 | 15 | >100 |
| 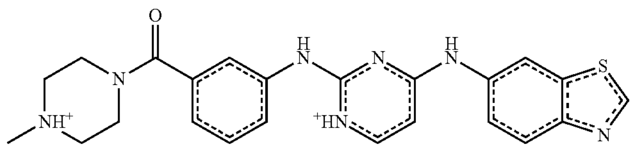 | 32 | 11 | 22 | 14 | 39 |
| 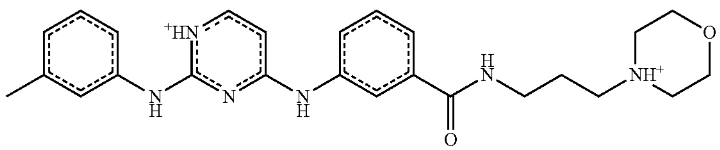 | 76 | 34 | 99 | 40 | >100 |
| 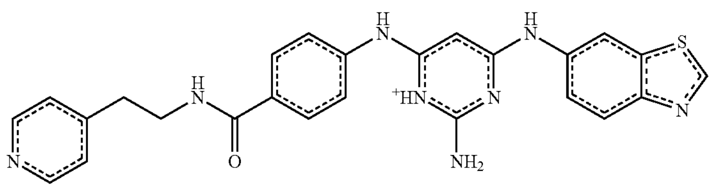 | 33 | 22 | 17 | >100 | >100 |
| 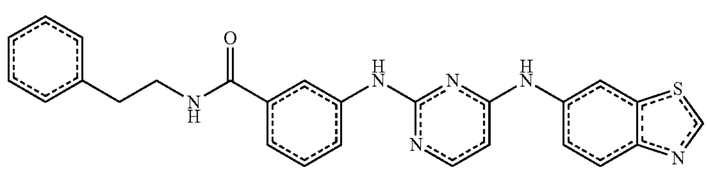 | 38 | 15 | 13 | 11 | 24 |
| | 19 | 10 | 16 | 7 | 17 |
| | 19 | 14 | 21 | 31 | 31 |
| | >100 | 9 | 25 | 9 | 81 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| 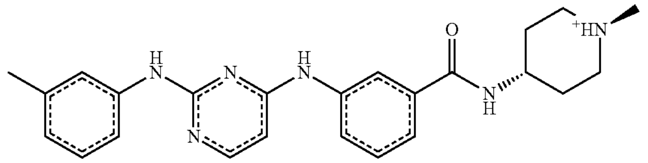 | 20 | 25 | 18 | 5 | 60 |
| 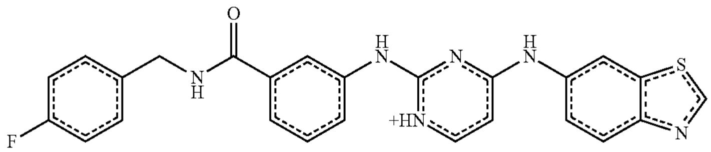 | 18 | 6 | 11 | 9 | 24 |
| 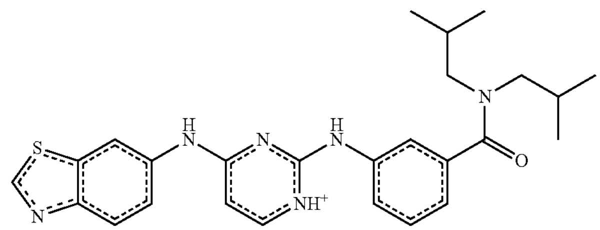 | 54 | 15 | 17 | 22 | >100 |
| | >100 | 39 | 46 | 89 | >100 |
| | | | | | |
| | >100 | >100 | 36 | 83 | 45 |
| | | | | | |
| | | | | | |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| | >100 | >100 | >100 | >100 | >100 |
| | >100 | >100 | >100 | >100 | >100 |
| | >100 | >100 | >100 | >100 | >100 |
| | >100 | >100 | >100 | >100 | >100 |
| | >100 | 77 | 30 | 21 | 54 |
| 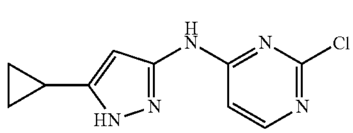 [SMILES: Clc1nccc(Nc2cc(C3CC3)[nH]n2)n1] | 63 | 45 | 29 | >100 | 31 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| 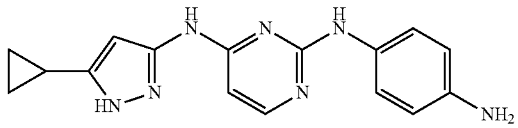 [SMILES: Nc1ccc(Nc2nccc(Nc3cc(C4CC4)[nH]n3)n2)cc1] | 1.9 | 0.4 | 5.0 | 10.0 | 30 |
| 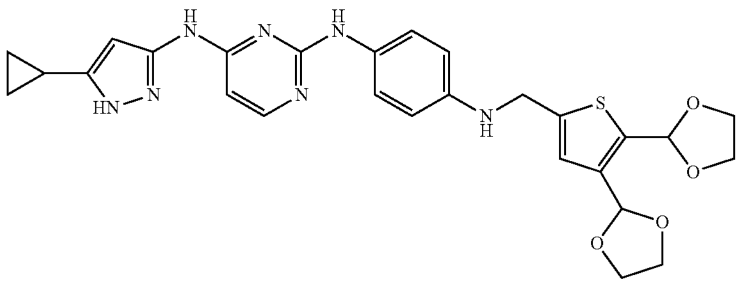 [SMILES: c1cc(Nc2cc(C3CC3)[nH]n2)nc(Nc2ccc(NCc3cc(C4OCCO4)c(C4OCCO4)s3)cc2)n1] | 14 | 13 | 13 | 14 | 18 |
| | >100 | 19 | 20 | 12 | 52 |
| | | 5 | 6 | 14 | 15 |
| | | 25 | 15 | 35 | 18 |
| | | 25 | 13 | 40 | 22 |
| | | >100 | >100 | >100 | >100 |
| | | >100 | >100 | >100 | >100 |

TABLE 3-continued
| Structure | EC50 U138 (uM) | EC50 HeLa (uM) | EC50 U87 (uM) | EC50 LN18 (uM) | EC50 U118 (uM) |
|---|---|---|---|---|---|
| 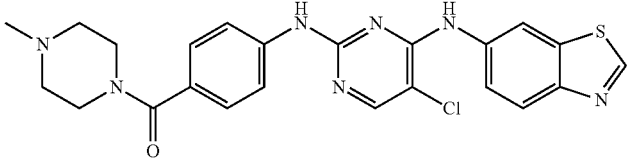 [SMILES: CN1CCN(C(=O)c2ccc(Nc3ncc(Cl)c(Nc4ccc5ncsc5c4)n3)cc2)CC1] | 28 | 12 | 15 | 22 | |
| 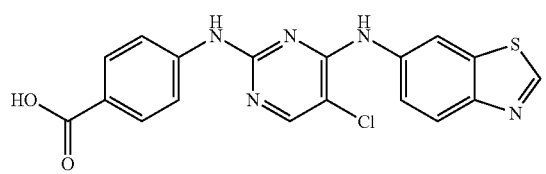 [SMILES: O=C(O)c1ccc(Nc2ncc(Cl)c(Nc3ccc4ncsc4c3)n2)cc1] | 100 | 5 | >100 | 18 | |
| 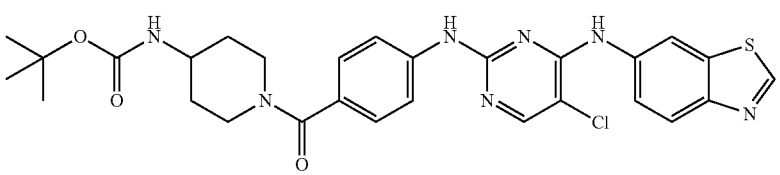 [SMILES: CC(C)(C)OC(=O)NC1CCN(C(=O)c2ccc(Nc3ncc(Cl)c(Nc4ccc5ncsc5c4)n3)cc2)CC1] | 9 | 15 | 80 | 18 | |
| 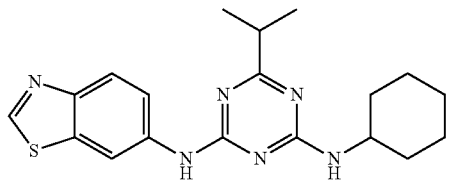 [SMILES: CC(C)c1nc(Nc2ccc3ncsc3c2)nc(NC2CCCCC2)n1] | | | | | |
| 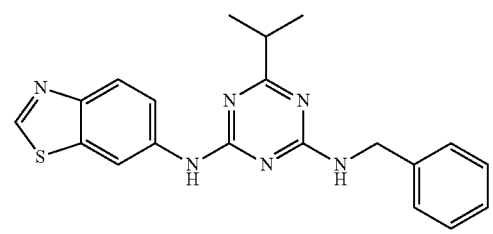 [SMILES: CC(C)c1nc(NCc2ccccc2)nc(Nc2ccc3ncsc3c2)n1] | | | | | |
| 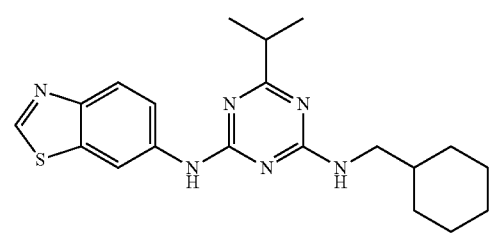 [SMILES: CC(C)c1nc(NCC2CCCCC2)nc(Nc2ccc3ncsc3c2)n1] | | | | | |
| 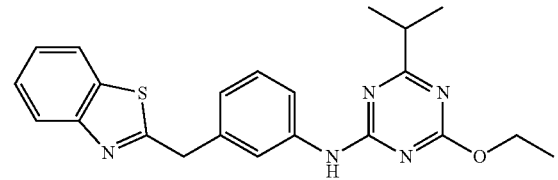 [SMILES: CCOc1nc(Nc2cccc(Cc3nc4ccccc4s3)c2)nc(C(C)C)n1] | | | | | |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| 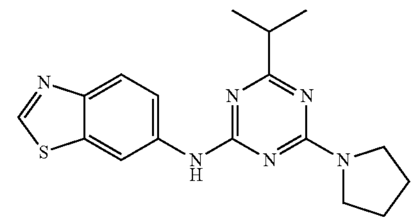 [SMILES: CC(C)c1nc(Nc2ccc3ncsc3c2)nc(N2CCCC2)n1] | 28 | 30 | >100 | 40 | |
| 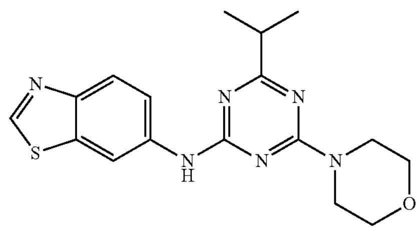 [SMILES: CC(C)c1nc(Nc2ccc3ncsc3c2)nc(N2CCOCC2)n1] | 80 | 100 | >100 | 80 | |
| | >100 | >100 | >100 | >100 | |
| | >100 | >100 | >100 | >100 | |
| 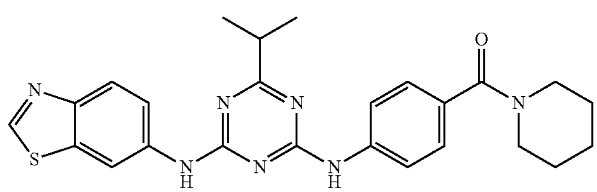 [SMILES: CC(C)c1nc(Nc2ccc(C(=O)N3CCCCC3)cc2)nc(Nc2ccc3ncsc3c2)n1] | 18 | 30 | 40 | 30 | |
| 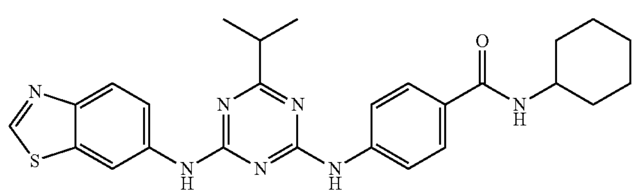 [SMILES: CC(C)c1nc(Nc2ccc(C(=O)NC3CCCCC3)cc2)nc(Nc2ccc3ncsc3c2)n1] | 40 | 28 | 45 | 30 | |
| 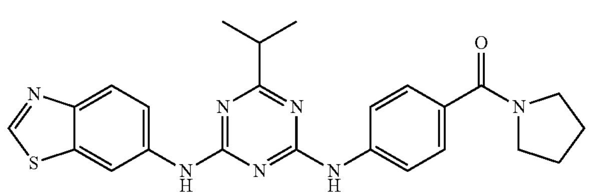 [SMILES: CC(C)c1nc(Nc2ccc(C(=O)N3CCCC3)cc2)nc(Nc2ccc3ncsc3c2)n1] | 22 | 4 | 30 | 20 | |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| [benzothiazole-NH-triazine(iPr)-NH-phenyl-C(O)-N(4-methylpiperazine)] | 28 | 30 | 35 | 40 | |
| [benzothiazole-NH-triazine(iPr)-NH-phenyl-C(O)-NH-benzyl] | 80 | 35 | 100 | 80 | |
| [benzothiazole-NH-triazine(iPr)-NH-phenyl-C(O)-morpholine] | >100 | 35 | >100 | 80 | |
| [cyclopropyl-pyrazole-NH-triazine(iPr)-NH-phenyl-NH2] | 8 | 14 | 35 | 40 | |
| [HOOC-phenyl-NH-pyrimidine(Cl)-NH-benzothiazole] | 100.0 | 15.0 | >100 | 40.0 | |
| [H2N-CH2-piperidine-C(O)-phenyl-NH-pyrimidine(Cl)-NH-benzothiazole] | 80.0 | 70.0 | >100 | 100.0 | |
| [H2N-piperidine-C(O)-phenyl-NH-pyrimidine(Cl)-NH-benzothiazole] | 60.0 | 30.0 | 40.0 | 40.0 | |
| [piperidine-C(O)-phenyl-NH-pyrimidine(Cl)-NH-benzothiazole] | 15.3 | 7.0 | 12.0 | 14.0 | |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| (4-methylpiperazine-carbonyl-phenyl)-aminopyrimidine-chloro-benzothiazole | 15.0 | 2.0 | 24.0 | 15.0 | |
| tetrahydropyridine-methoxyphenyl-aminopyrimidine-benzothiazole HCl | 6.9 | 15.0 | 18.0 | 15.0 | |
| piperidin-4-ylmethyl-benzamide-aminopyrimidine-chloro-benzothiazole TFA | >100 | >100 | >100 | >100 | |
| 4-aminopiperidine-carbonyl-phenyl-aminopyrimidine-chloro-benzothiazole | 25.0 | 20.0 | 35.0 | 40.0 | |
| 4-(aminomethyl)piperidine-carbonyl-phenyl-aminopyrimidine-chloro-benzothiazole | 20.0 | 3.0 | 18.0 | 19.0 | |
| piperidin-4-ylmethyl-benzamide-aminopyrimidine-chloro-benzothiazole | 80.0 | 30.0 | 80.0 | 30.0 | |
| indol-1-yl-propanamide-p-tolyl | >100 | >100 | | >100 | |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| (indole-CH2CH2-C(O)NH-C6H4-C(O)OEt) | >100 | >100 | | | >100 |
| (indole-CH2CH2-C(O)NH-C6H4-OMe) | >100 | 30 | | | >100 |
| (indole-CH2CH2-C(O)NH-C6H4-F) | >100 | >100 | | | >100 |
| (indole-CH2CH2-C(O)NH-C6H3(CF3)(OMe)) | 98 | >100 | | | 47 |
| (indole-CH2CH2-C(O)NH-pyrazine) | 92 | 64 | | | 33 |

TABLE 3-continued
| Structure | EC50 U138 (uM) | EC50 HeLa (uM) | EC50 U87 (uM) | EC50 LN18 (uM) | EC50 U118 (uM) |
|---|---|---|---|---|---|
| 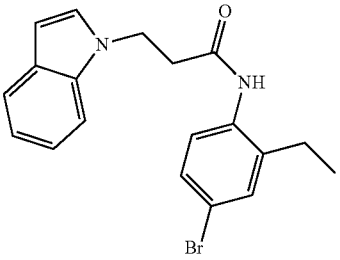 [SMILES: CCc1cc(Br)ccc1NC(=O)CCn1ccc2ccccc21] | >100 | 43 | | | >100 |
| 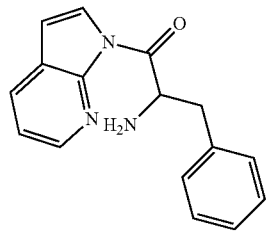 [SMILES: NC(Cc1ccccc1)C(=O)n1ccc2cccnc21] | >100 | 45 | | | >100 |
| 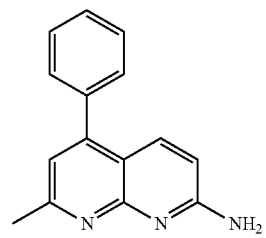 [SMILES: Cc1cc(-c2ccccc2)c2ccc(N)nc2n1] | | 46 | 58 | | >100 |
| 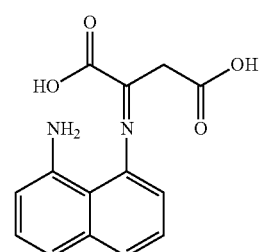 | >100 | 63 | | | >100 |
| 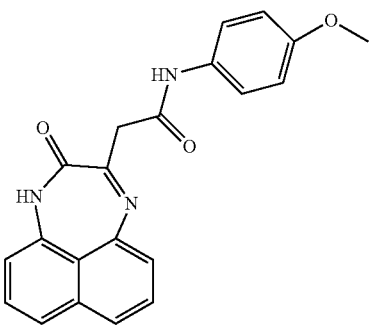 [SMILES: COc1ccc(NC(=O)CC2=Nc3cccc4cccc(c34)NC2=O)cc1] | >100 | 17 | | | >100 |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| 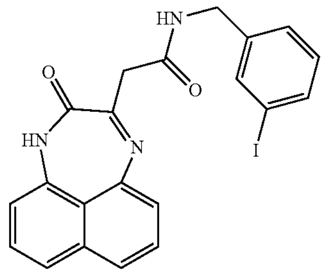 [SMILES: O=C(CC1=Nc2cccc3cccc(c23)NC1=O)NCc1cccc(I)c1] | >100 | 10 | | | 51 |
| | | | | | |
| | | | | | |
| | | | | | |
| | | | | | |
| | | | | | |
| | | | | | |

TABLE 3-continued

| Structure | EC50 U138 (uM) | EC50 HeLa (uM) | EC50 U87 (uM) | EC50 LN18 (uM) | EC50 U118 (uM) |
|---|---|---|---|---|---|
| [structure: benzothiazole-NH-pyrimidine(Br)-NH-phenyl-C(O)-piperidine] | 11.86 | 15 | 12 | 20 | 13 |
| [structure: 2,6-dichloro-4-fluorophenyl-CH(CH3)-O-pyridine(NH2)-pyrazole-piperidine-NH3+] | | | | | |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

Repurposing Crizotinib

Augusta will repurpose drugs to expand their oncology franchise. Here we describe the repurposing of Xalkori (Crizotinib; PF-02341066; Pfizer) for the treatment of ROS kinase-driven cancers such as glioblastoma, non small cell lung carcinoma (NSCLC), cholangiocarcinoma and other p53-inactivated cancers.

The FDA has approved Xalkori in August 2011 for the treatment of advanced anaplastic lymphoma kinase (ALK)-positive non-small cell lung cancers. The ALK-positive tumors refer to a gene rearrangement that fuses of the echinoderm microtubule-associated protein-like 4 (EML4) gene and the anaplastic lymphoma kinase (ALK) gene. Xalkori is a small molecule inhibitor developed to inhibit the ALK kinase, but due to structural similarity in the kinase domain of other protein kinases, it also recognizes MET kinase. Xalkori has produced dramatic responses in clinical trials, ranging from tumor regression to complete tumor elimination.

Although Xalkori has demonstrated promising therapeutic potential, we note that Xalkori is a multikinase inhibitor that effectively blocks the kinase activity of ALK and MET (Cui et al., 2011). This finding may be responsible of adverse events related to long-term therapy (see: (http://www.cancer.gov/cancertopics/druginfo/fda-crizotinib). Importantly, Augusta has identified ROS as a third sensitive target of Xalkori (unpublished data; see attached PDF file). Like the ALK gene rearrangement there is also a ROS gene rearrangement resulting in the fusion of a Golgi apparatus-associated protein called FIG to the kinase domain of ROS, producing the hybrid FIG-ROS kinase (Charest et al., 2003). The hybrid kinase is a potent oncogene, capable of initiating malignant transformation in vitro when localized to the Golgi apparatus and activating growth signaling pathways (Charest et al., 2003; Charest et al., 2006). In a mouse model system, the FIG-ROS fusion cooperates with the loss of CDKN2A to produce glioblastomas (Charest et al., 2006). Oncogenic forms of ROS have also been documented in patient tumors with non small cell lung cancer and cholangiocarcinoma (Acquaviva et al., 2009; Rikova et al., 2007; Gu et al., 2011).

The Augusta founding labs have revealed that for certain tumor cell types, the wild type ROS gene can function as a cancer survival gene in the absence of functional TP53 activity, accentuating the importance of the ROS RTK in cancer development and progression (Baldwin et al., 2010). These data demonstrate that mutated and wild type ROS may be attractive drug targets for glioblastoma, lung cancer, cholanagiocarcinoma, and potentially other cancers. Moreover, genetic screening for ROS rearrangements as a prerequisite for treatment with a ROS-targeting therapeutic may be a grievous miscalculation, if the wt ROS protein is essential for driving tumor growth under specific conditions (e.g., following inactivation of TP53). Thousands of patients may be prevented from receiving life-extending therapy.

Augusta has a proprietary 3D model of the ROS kinase that has been constructed and thoroughly validated using biological and X-ray data (FIG. 1). We capitalized on an important finding pertaining to ROS homology modeling. The ROS kinase domain possesses 48% identity to the ALK kinase domain in amino acid sequence. The binding site similarity between ALK and ROS prompted us to evaluate the possibility that commercially available ALK inhibitors may also inhibit ROS kinase activity and therefore we tested Xalkori in our in vitro kinase and cell-based assays. Our in silico predictions correctly predicted that Xalkori is a highly potent ROS inhibitor in vitro, with an $IC_{50}$ kinase inhibition value of 1 nM (FIG. 2) and an $EC_{50}$ for glioblastoma growth inhibition ranging from 12 to 20 nM depending on the cell line (FIG. 3).

FIG. 1: Xalkori/Crizotinib docked into a structural model of the ROS ATP binding site. Dashed yellow lines represent hydrogen bonds. The amino pyridine core forms hydrogen bonds with backbone atoms of the hinge residues Met2029 and Glu2030, while the piperidine group forms a salt bridge with Asp2033.

FIG. 2: A subset of small molecules that inhibited the in vitro catalytic activity of ROS, employing a substrate phosphorylation assay purchased from Cisbio. All compounds were evaluated for kinase inhibition using a high throughput screening platform for phospho-detection of kinase activity, employing a biotinylated peptide substrate and a specific anti-phospho peptide antibody. A 12 point dose response curve was generated to accurately assess $IC_{50}$ values. The concentration of Crizotinib producing a 50% inhibition of ROS kinase activity (i.e., IC50) was 1.556 nM.

FIG. 3: Potency, selectivity and growth inhibitory effects of Xalkori in in vitro kinase and cell-based assays. Crizotinib inhibition as judged by three approaches: 1) inhibition of ROS enzymatic activity in vitro; 2) inhibition of a second unrelated receptor tyrosine kinase EGFR; and 3) growth inhibition of one cervical cancer cell line (HeLa) and four glioblastoma cells lines (U138, U118, LN18 and U87). U138 and U118 have been documented to express aberrant ROS (FIG-ROS fusion). The cell-based assay conditions measure cell proliferation/survival by Alamar blue staining.

We claim:

1. A method of reducing the speed of, stopping, or reversing progression of abnormal cell growth in a mammal, the method comprising:
   administering to the mammal a composition comprising a therapeutically effective amount of a ROS tyrosine kinase inhibitor compound of formula I:

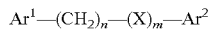

or a pharmaceutically acceptable salt thereof,
   wherein
   Ar¹ is comprised of the formula:

Ar³ is aryl or heteroaryl, wherein the heteroatom of said heteroaryl independently numbers 1, 2 or 3, and is independently selected from N, S or O, wherein each of said aryl or heteroaryl is either unsubstituted or independently substituted with one or more substituent which is independently selected from the group consisting of deuterium, halo, amino, aminoalkyl-, (amino)alkoxy-, —CH$_z$F$_{3-z}$, —OCH$_z$F$_{3-z}$, C(O)(O)H, alkyl, alkenyl, alkynyl, alkoxy-, -cycloalkyl, -heterocycloalkyl, -aryl, —C(O)-alkyl, —C(O)-aryl, —C(O)cycloalkyl, —C(O)-heterocycloalkyl, and heteroaryl, with the proviso that no two adjacent ring heteroatoms on a ring are both S or both O; and
   Ar⁴ is a six membered aryl or heteroaryl, wherein said heteroaryl independently has 1, 2, or 3 heteroatoms with each heteroatom being independently selected from N, S, or O,
      wherein said aryl or heteroaryl is unsubstituted or independently substituted with halo or alkyl;
   n is 0 or;
   X is N;
   z is 0, 1, 2, or 3;
   m is 1;
   Ar² is aryl, heteroaryl, arylalkyl or heteroarylalkyl, wherein said heteroaryl or heteroarylalkyl independently has 1, 2 or 3 heteroatoms, with each heteroatom being independently selected from N, S or O, wherein any of said aryl, heteroaryl, arylalkyl and heteroarylalkyl is either unsubstituted or independently substituted with one substituent which is independently selected from the group consisting of cycloalkyl, -heterocycloalkyl, -aryl, and heteroaryl, with the proviso that no two adjacent ring heteroatoms on a ring are both S or both O; and
   wherein said abnormal cell growth is caused by an elevated level of ROS or expression of fusion protein FIG-ROS.

2. The method of claim 1, wherein Ar² is

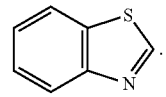

3. The method of claim 1, wherein Ar² is

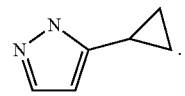

4. The method of claim 1, wherein
Ar³ is aryl or heteroaryl wherein the heteroatom of said heteroaryl independently numbers 1, 2 or 3, and is independently selected from N, S or O.

5. The method of claim 1, wherein Ar³ is

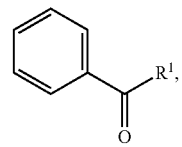

wherein
R¹ is cycloalkyl or heterocycloalkyl.

6. The method of claim 5, wherein R¹ is

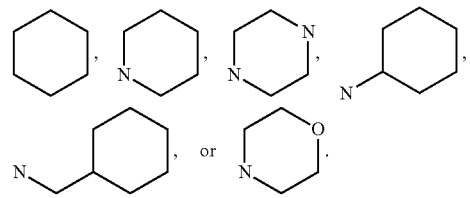

7. The method of claim 5, wherein Ar² is

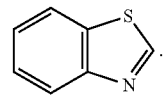

8. The method of claim 1, wherein Ar⁴ is heteroaryl wherein the heteroatom of said heteroaryl is N and independently numbers 1, 2 or 3, further wherein the atoms of said heteroaryl is unsubstituted or independently substituted with halo or alkyl.

9. The method of claim 8, wherein Ar⁴ is

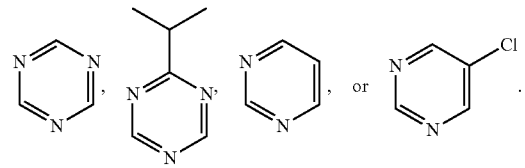

10. The method of claim 6, wherein Ar² is

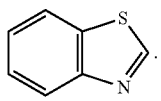

11. The method of claim 6, wherein Ar² is

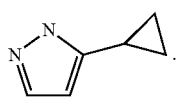

12. The method of claim 9, wherein Ar² is

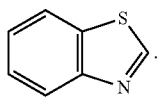

13. The method of claim 9, wherein Ar² is

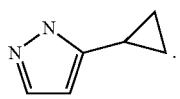

14. The method of claim 2, wherein Ar¹ is

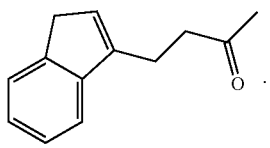

15. The method of claim 14, wherein Ar² is benzene wherein each hydrogen atom on said benzene is un-substituted or independent substituted with one or more substituents which can be the same or different and are independently selected from the group consisting of halo, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

16. The method of claim 1, wherein Ar¹ is

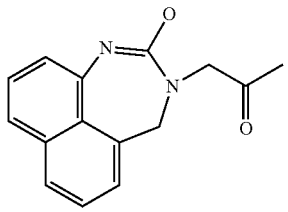

17. The method of claim 16, wherein Ar² is benzene wherein each hydrogen atom on said benzene is un-substituted or independent substituted with one or more substituents which can be the same or different and are independently selected from the group consisting of halo, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, and -heterocycloalkyl.

18. The method of claim 1, wherein the mammal is human.

19. The method of claim 1, wherein the abnormal cell growth is mediated at least in part, by a ROS tyrosine kinase or a fusion gene of the ROS tyrosine kinase with another sequence.

20. The method of claim 1, wherein the abnormal cell growth is cancer.

21. The method of claim 20, wherein said cancer is selected from the group consisting of gastric cancer, glioblastoma, cholangiocarcinoma, ovarian cancer, uterine cancer, colon cancer, cervical cancer, lung cancer, non-small cell lung cancer (NSCLC), prostate cancer, skin cancer, and bladder cancer.

22. The method of claim 1, wherein the pharmaceutical composition further comprising at least one pharmaceutically acceptable carrier.

23. The method of claim 22, wherein the pharmaceutical composition further comprising therapeutically effective amounts of one or more additional therapeutic agents.

24. The method of claim 23, wherein said one or more additional therapeutic agents are selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib, R115777, L778,123, BMS 214662, gefitnib, erlotnib, C225, imatinib, interferon, pegylated interferon alfa-2b, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin, Pentostatine, Vinblastine, Vincristine, Vindesine, Bleomycin, Dactinomycin, Daunorubicin, Doxorubicin, Epirubicin, Idarubicin, plicamycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, Campath, leucovorin, and dexamethasone, bicalutamide, carboplatin, chlorambucil, cisplatin, letrozole, megestrol, valrubicin, and vinvlastin.

25. A method of reducing the speed of, stopping, or reversing progression of abnormal cell growth in a mammal, comprising administering to the mammal a composition comprising therapeutically effective amount of a compound selected from the group consisting

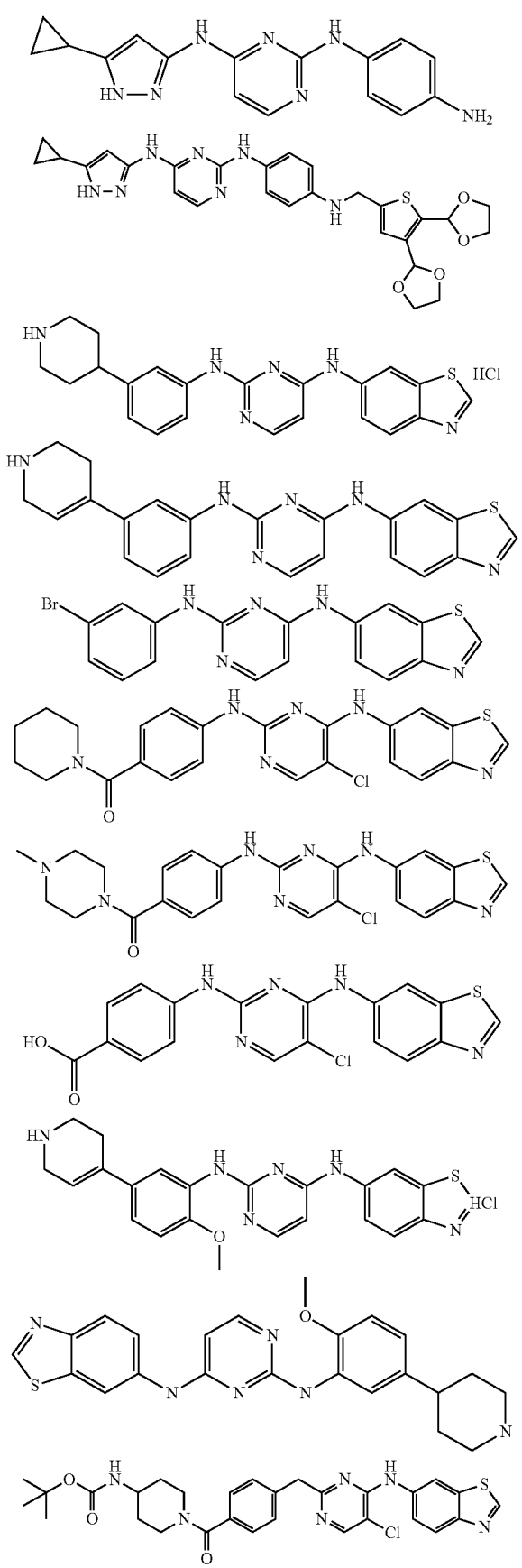
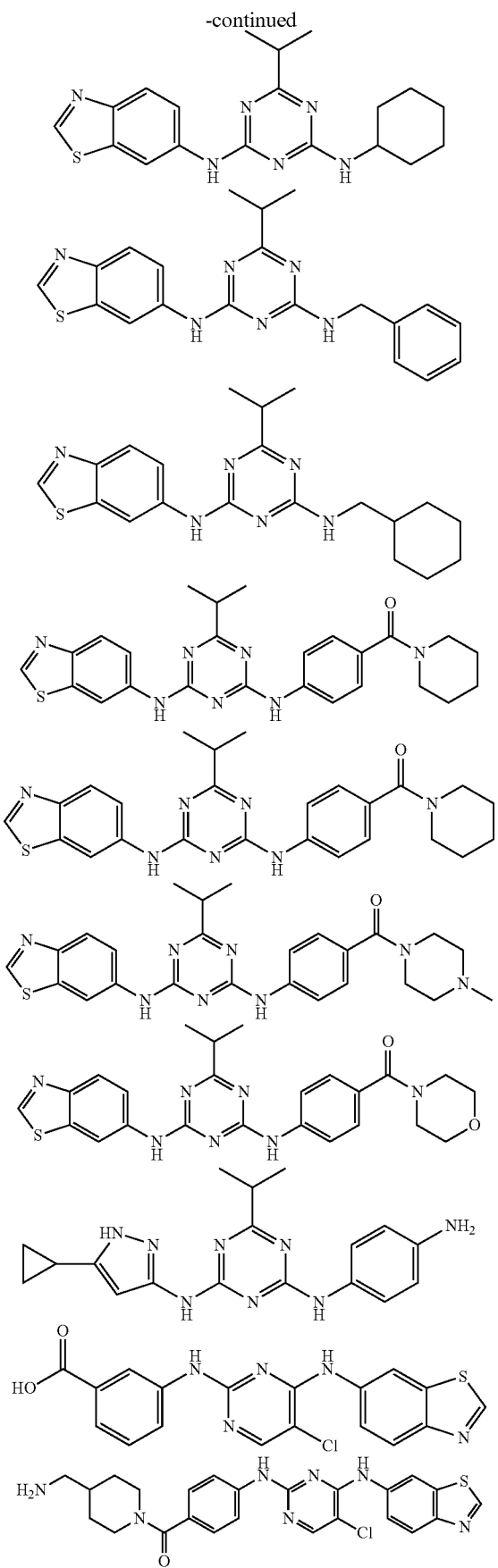
-continued

-continued
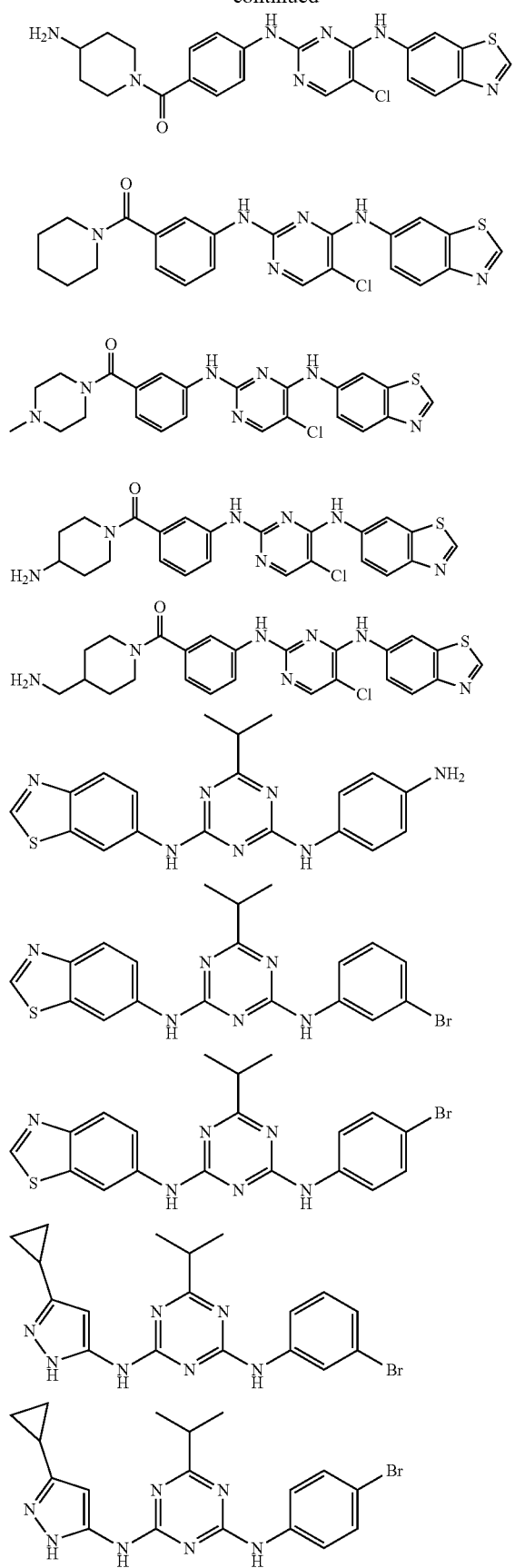
-continued
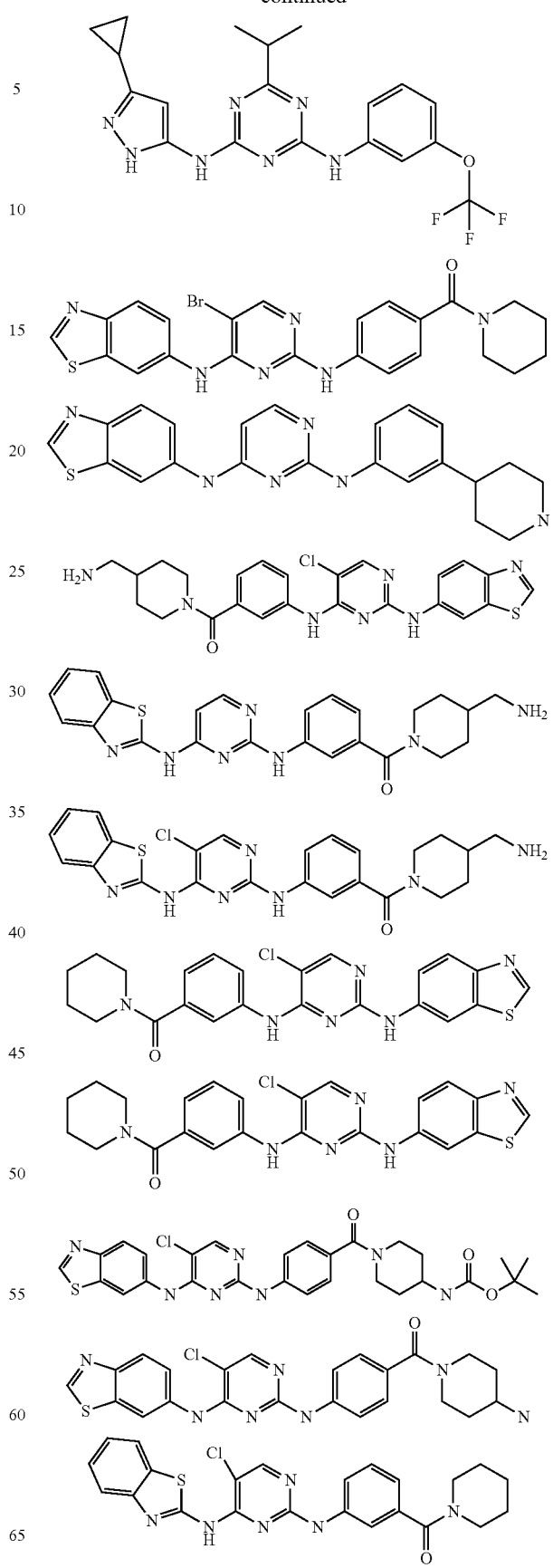

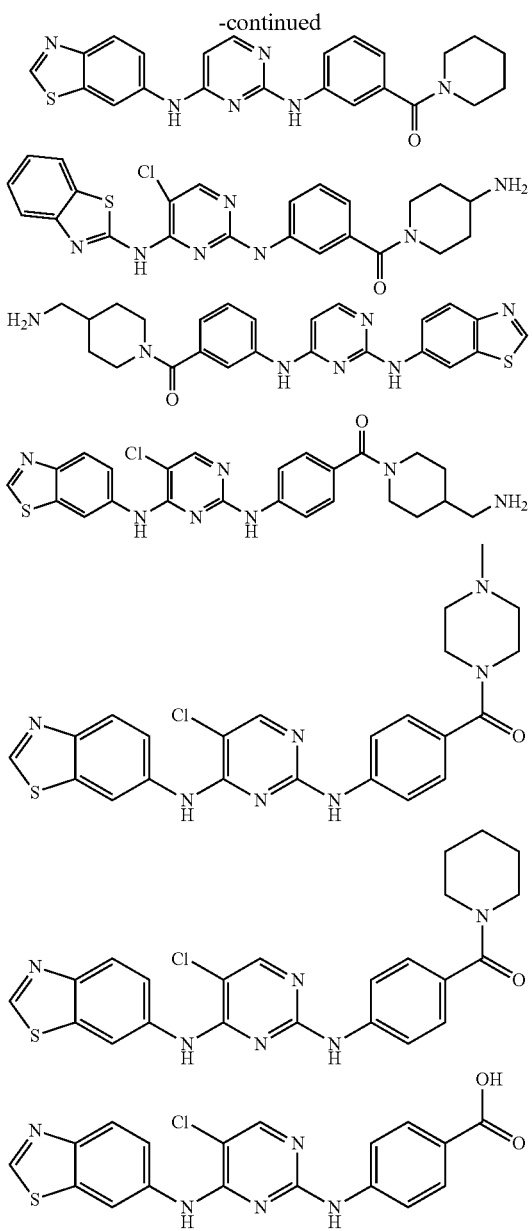

or a pharmaceutically acceptable salt thereof, and wherein said abnormal cell growth is caused by an elevated level of ROS or expression of fusion protein FIG-ROS.

26. The method of claim 25, wherein the mammal is human.

27. A method of claim 26, wherein the composition reduces the speed of, stops, or reverses progression of abnormal cell growth through the inhibition of ROS tyrosine kinase activities.

28. The method of claim 25, wherein the abnormal cell growth is cancer.

29. The method of claim 28, wherein said cancer is selected from the group consisting of gastric cancer, glioblastoma, cholangiocarcinoma, ovarian cancer, uterine cancer, colon cancer, cervical cancer, lung cancer, non-small cell lung cancer (NSCLC), prostate cancer, skin cancer, and bladder cancer.

30. The method of claim 25, wherein the pharmaceutical composition further comprising at least one pharmaceutically acceptable carrier.

31. The method of claim 30, wherein the pharmaceutical composition further comprising therapeutically effective amounts of one or more additional therapeutic agents.

32. The method of claim 31, wherein said one or more additional therapeutic agents are selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib, R115777, L778,123, BMS 214662, gefitnib, erlotnib, C225, imatinib, interferon, pegylated interferon alfa-2b, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin, Pentostatine, Vinblastine, Vincristine, Vindesine, Bleomycin, Dactinomycin, Daunorubicin, Doxorubicin, Epirubicin, Idarubicin, plicamycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, Campath, leucovorin, and dexamethasone, bicalutamide, carboplatin, chlorambucil, cisplatin, letrozole, megestrol, valrubicin, and vinvlastin.

* * * * *